US011110210B2

(12) United States Patent
Eaton et al.

(10) Patent No.: US 11,110,210 B2
(45) Date of Patent: *Sep. 7, 2021

(54) SELF-EXPANDING DEVICES AND METHODS THEREFOR

(71) Applicant: Intersect ENT, Inc., Menlo Park, CA (US)

(72) Inventors: Donald J. Eaton, Los Altos, CA (US); Bin Huang, Pleasanton, CA (US); Anthony J. Abbate, Santa Clara, CA (US); Gail M. Zaler, Milpitas, CA (US); David C. Gale, Kennesaw, GA (US)

(73) Assignee: Intersect ENT, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/075,572

(22) Filed: Oct. 20, 2020

(65) Prior Publication Data

US 2021/0030927 A1 Feb. 4, 2021

Related U.S. Application Data

(63) Continuation of application No. 16/727,345, filed on Dec. 26, 2019, which is a continuation of application
(Continued)

(51) Int. Cl.
*A61F 2/18* (2006.01)
*A61L 31/02* (2006.01)
(Continued)

(52) U.S. Cl.
CPC ............ *A61L 31/022* (2013.01); *A61B 17/24* (2013.01); *A61B 17/3468* (2013.01);
(Continued)

(58) Field of Classification Search
CPC .... A61F 2310/0096; A61F 2310/00389; A61F 2/18; A61L 31/08
(Continued)

(56) References Cited

U.S. PATENT DOCUMENTS

| 374,026 A | 11/1887 | Williams |
| 1,381,829 A | 6/1921 | Hartman |

(Continued)

FOREIGN PATENT DOCUMENTS

| AU | 2008/201495 A1 | 10/2008 |
| DE | 101 05 592 A1 | 8/2002 |
| EP | 0 423 916 A1 | 4/1991 |
| EP | 0 761 251 A1 | 3/1997 |
| EP | 0 938 880 A2 | 9/1999 |
| EP | 1 415 671 A1 | 5/2004 |
| EP | 1 870 057 A1 | 12/2007 |

(Continued)

OTHER PUBLICATIONS

Becker, D.G. (2003). "The Minimally Invasive, Endoscopic Approach to Sinus Surgery," *Journal of Long-Term Effects of Medical Implants* 13(3):207-221.
(Continued)

*Primary Examiner* — Suzette J Gherbi
(74) *Attorney, Agent, or Firm* — Cooley LLP

(57) ABSTRACT

Described here are delivery devices for delivering one or more implants to the body, and methods of using. The delivery devices may deliver implants to a variety of locations within the body, for a number of different uses. In some variations, the delivery devices have a cannula with one or more curved sections. In some variations, a pusher may be used to release one or more implants from the cannula. In some variations, one or more of the released implants may be a self-expanding device. Methods of delivering implants to one or more sinus cavities are also described here.

11 Claims, 26 Drawing Sheets

Related U.S. Application Data

No. 16/588,294, filed on Sep. 30, 2019, which is a continuation of application No. 16/021,659, filed on Jun. 28, 2018, now Pat. No. 10,471,185, which is a continuation of application No. 14/081,974, filed on Nov. 15, 2013, now Pat. No. 10,010,651, which is a continuation of application No. 12/334,373, filed on Dec. 12, 2008, now Pat. No. 8,585,730.

(60) Provisional application No. 61/058,803, filed on Jun. 4, 2008, provisional application No. 61/014,653, filed on Dec. 18, 2007.

(51) Int. Cl.

| | | |
|---|---|---|
| *A61F 2/86* | (2013.01) | |
| *A61F 2/95* | (2013.01) | |
| *A61F 5/08* | (2006.01) | |
| *A61L 31/14* | (2006.01) | |
| *A61B 17/24* | (2006.01) | |
| *A61B 17/34* | (2006.01) | |
| *A61K 9/70* | (2006.01) | |
| *A61F 2/89* | (2013.01) | |
| *A61L 31/16* | (2006.01) | |
| *A61F 2/04* | (2013.01) | |
| *A61L 31/10* | (2006.01) | |
| *A61F 2/82* | (2013.01) | |
| *A61M 29/00* | (2006.01) | |
| *A61F 2/915* | (2013.01) | |

(52) U.S. Cl.
CPC ............ *A61B 17/3478* (2013.01); *A61F 2/04* (2013.01); *A61F 2/18* (2013.01); *A61F 2/82* (2013.01); *A61F 2/86* (2013.01); *A61F 2/89* (2013.01); *A61F 2/95* (2013.01); *A61F 5/08* (2013.01); *A61K 9/70* (2013.01); *A61L 31/10* (2013.01); *A61L 31/148* (2013.01); *A61L 31/16* (2013.01); *A61M 29/00* (2013.01); *A61B 2017/3454* (2013.01); *A61F 2/186* (2013.01); *A61F 2/9522* (2020.05); *A61F 2/9524* (2020.05); *A61F 2002/048* (2013.01); *A61F 2002/91508* (2013.01); *A61F 2210/0004* (2013.01); *A61F 2210/0076* (2013.01); *A61F 2220/005* (2013.01); *A61F 2220/0058* (2013.01); *A61F 2230/0091* (2013.01); *A61F 2240/001* (2013.01); *A61F 2250/003* (2013.01); *A61F 2250/006* (2013.01); *A61F 2250/0067* (2013.01)

(58) Field of Classification Search
USPC .............................................. 623/1.46–1.48
See application file for complete search history.

(56) References Cited

U.S. PATENT DOCUMENTS

| | | |
|---|---|---|
| 1,485,126 A | 2/1924 | Schumacher |
| 1,520,908 A | 12/1924 | Meyer |
| 1,658,801 A | 2/1928 | Condren |
| 2,009,393 A | 7/1935 | Failla |
| 2,096,162 A | 10/1937 | Daley |
| 2,691,985 A | 10/1954 | Newsom |
| 3,049,125 A | 8/1962 | Kriwkowitsch |
| 3,473,165 A | 10/1969 | Gran et al. |
| 3,502,078 A | 3/1970 | Hill et al. |
| 3,570,494 A | 3/1971 | Gottschalk |
| 3,583,391 A | 6/1971 | Cox et al. |
| 3,766,924 A | 10/1973 | Pidgeon |
| 3,800,788 A | 4/1974 | White |
| 3,894,539 A | 7/1975 | Tallent |
| 3,903,893 A | 9/1975 | Scheer |
| 3,913,584 A | 10/1975 | Walchle et al. |
| 4,094,303 A | 6/1978 | Johnston |
| 4,245,652 A | 1/1981 | Kelly et al. |
| 4,389,208 A | 6/1983 | LeVeen et al. |
| 4,419,095 A | 12/1983 | Nebergall et al. |
| D276,937 S | 12/1984 | Griggs |
| 4,534,761 A | 8/1985 | Raible |
| 4,580,568 A | 4/1986 | Gianturco |
| 4,604,920 A | 8/1986 | Dupke |
| 4,627,971 A | 12/1986 | Ayer |
| 4,650,488 A | 3/1987 | Bays et al. |
| 4,655,771 A | 4/1987 | Wallsten |
| 4,704,126 A | 11/1987 | Baswell et al. |
| 4,737,141 A | 4/1988 | Spits |
| 4,744,792 A | 5/1988 | Sander et al. |
| 4,753,636 A | 6/1988 | Free |
| 4,793,351 A | 12/1988 | Landman et al. |
| 4,886,493 A | 12/1989 | Yee |
| 4,941,881 A | 7/1990 | Masters et al. |
| 4,964,850 A | 10/1990 | Bouton et al. |
| 5,000,957 A | 3/1991 | Eckenhoff et al. |
| 5,011,474 A | 4/1991 | Brennan |
| 5,035,706 A | 7/1991 | Giantureo et al. |
| 5,062,829 A | 11/1991 | Pryor et al. |
| 5,116,311 A | 5/1992 | Löfstedt |
| 5,139,502 A | 8/1992 | Berg et al. |
| 5,139,510 A | 8/1992 | Goldsmith, III et al. |
| 5,139,832 A | 8/1992 | Hayashi et al. |
| 5,167,614 A | 12/1992 | Tessmann et al. |
| 5,189,110 A | 2/1993 | Ikematu et al. |
| 5,217,484 A | 6/1993 | Marks |
| 5,246,455 A | 9/1993 | Shikani |
| 5,256,146 A | 10/1993 | Ensminger et al. |
| 5,300,119 A | 4/1994 | Blom |
| 5,312,813 A | 5/1994 | Costerton et al. |
| 5,336,163 A | 8/1994 | DeMane et al. |
| 5,342,296 A | 8/1994 | Persson et al. |
| 5,344,426 A * | 9/1994 | Lau .................... A61F 2/92 606/198 |
| 5,348,553 A | 9/1994 | Whitney |
| 5,350,580 A | 9/1994 | Muchow et al. |
| 5,360,406 A | 11/1994 | Boykin et al. |
| 5,391,179 A | 2/1995 | Mezzoli |
| 5,443,498 A | 8/1995 | Fontaine |
| 5,501,700 A | 3/1996 | Hirata |
| 5,507,210 A | 4/1996 | Paramest |
| 5,507,807 A | 4/1996 | Shippert |
| 5,512,055 A | 4/1996 | Domb et al. |
| 5,538,738 A | 7/1996 | Ritter et al. |
| 5,540,712 A | 7/1996 | Kleshinski et al. |
| 5,556,413 A | 9/1996 | Lam |
| 5,632,762 A | 5/1997 | Myler |
| 5,645,584 A | 7/1997 | Suyama |
| 5,664,567 A | 9/1997 | Linder |
| 5,672,179 A | 9/1997 | Garth et al. |
| 5,693,065 A | 12/1997 | Rains, III |
| 5,713,855 A | 2/1998 | Shippert |
| 5,746,224 A | 5/1998 | Edwards |
| 5,749,921 A | 5/1998 | Lenker et al. |
| 5,792,100 A | 8/1998 | Shantha |
| 5,800,379 A | 9/1998 | Edwards |
| 5,800,429 A | 9/1998 | Edwards |
| 5,827,224 A | 10/1998 | Shippert |
| 5,895,408 A | 4/1999 | Pagan |
| 5,899,878 A | 5/1999 | Glassman |
| 5,928,190 A | 7/1999 | Davis |
| 5,992,000 A | 11/1999 | Humphrey et al. |
| 6,033,436 A | 3/2000 | Steinke et al. |
| 6,054,122 A | 4/2000 | MacPhee et al. |
| 6,063,102 A | 5/2000 | Morales |
| 6,074,381 A | 6/2000 | Dinh et al. |
| 6,082,990 A | 7/2000 | Jackson et al. |
| 6,092,273 A | 7/2000 | Villareal |
| 6,092,528 A | 7/2000 | Edwards |
| 6,108,886 A | 8/2000 | Kimes et al. |
| 6,113,641 A | 9/2000 | Leroy et al. |
| 6,123,697 A | 9/2000 | Shippert |
| 6,149,681 A | 11/2000 | Houser et al. |

(56) References Cited

U.S. PATENT DOCUMENTS

| | | | |
|---|---|---|---|
| 6,149,944 A | 11/2000 | Jeong et al. |
| 6,152,946 A | 11/2000 | Broome et al. |
| 6,180,848 B1 | 1/2001 | Flament et al. |
| 6,190,353 B1 | 2/2001 | Makower et al. |
| 6,195,225 B1 | 2/2001 | Komatsu et al. |
| 6,200,335 B1 | 3/2001 | Igaki |
| 6,214,036 B1 * | 4/2001 | Letendre ................ A61F 2/07 623/1.11 |
| 6,224,626 B1 | 5/2001 | Steinke |
| 6,228,111 B1 | 5/2001 | Törmälä et al. |
| 6,280,413 B1 | 8/2001 | Clark et al. |
| 6,290,728 B1 | 9/2001 | Phelps et al. |
| 6,297,227 B1 | 10/2001 | Johnson |
| 6,302,875 B1 | 10/2001 | Makower et al. |
| 6,306,084 B1 | 10/2001 | Pinczower |
| 6,342,068 B1 | 1/2002 | Thompson |
| 6,347,241 B2 | 2/2002 | Burbank et al. |
| 6,350,465 B1 | 2/2002 | Jonnalagadda et al. |
| 6,352,547 B1 | 3/2002 | Brown et al. |
| 6,355,032 B1 | 3/2002 | Hovda et al. |
| 6,375,615 B1 | 4/2002 | Flaherty et al. |
| 6,386,197 B1 | 5/2002 | Miller |
| 6,398,758 B1 | 6/2002 | Jacobsen et al. |
| 6,409,750 B1 | 6/2002 | Hyodoh et al. |
| 6,447,539 B1 | 9/2002 | Nelson et al. |
| 6,491,940 B1 | 12/2002 | Levin |
| 6,524,608 B2 | 2/2003 | Ottoboni et al. |
| 6,537,294 B1 | 3/2003 | Boyle et al. |
| 6,543,452 B1 | 4/2003 | Lavigne |
| 6,544,230 B1 | 4/2003 | Flaherty et al. |
| 6,555,566 B2 | 4/2003 | Ponikau |
| 6,562,058 B2 | 5/2003 | Seguin et al. |
| 6,565,597 B1 | 5/2003 | Fearnot et al. |
| 6,589,286 B1 | 7/2003 | Litner |
| 6,605,294 B2 | 8/2003 | Sawhney |
| 6,606,995 B1 | 8/2003 | Sadek et al. |
| 6,618,921 B1 | 9/2003 | Thornton |
| 6,648,849 B2 | 11/2003 | Tenhuisen et al. |
| 6,685,648 B2 | 2/2004 | Flaherty et al. |
| 6,692,455 B2 | 2/2004 | Goode et al. |
| 6,695,856 B2 | 2/2004 | Kieturakis et al. |
| 6,709,465 B2 | 3/2004 | Mitchell et al. |
| 6,712,859 B2 | 3/2004 | Rousseau et al. |
| 6,715,485 B1 | 4/2004 | Djupesland |
| 6,719,934 B2 | 4/2004 | Stinson |
| 6,746,426 B1 | 6/2004 | Flaherty et al. |
| 6,749,617 B1 | 6/2004 | Palasis et al. |
| 6,884,260 B2 | 4/2005 | Kugler et al. |
| 6,942,690 B1 | 9/2005 | Pollock et al. |
| 6,945,992 B2 | 9/2005 | Goodson, IV et al. |
| 6,951,053 B2 | 10/2005 | Padilla et al. |
| 6,966,923 B2 | 11/2005 | Gittings |
| 7,018,401 B1 | 3/2006 | Hyodoh et al. |
| 7,072,720 B2 | 7/2006 | Puskas |
| 7,074,426 B2 | 7/2006 | Kochinke |
| 7,108,706 B2 | 9/2006 | Hogle |
| RE39,321 E | 10/2006 | MacPhee et al. |
| 7,195,016 B2 | 3/2007 | Loyd et al. |
| 7,225,518 B2 | 6/2007 | Eidenschink et al. |
| 7,235,099 B1 | 6/2007 | Duncavage et al. |
| 7,249,390 B2 | 7/2007 | Yale et al. |
| RE39,923 E | 11/2007 | Blom |
| 7,314,484 B2 | 1/2008 | Deem et al. |
| 7,316,147 B2 | 1/2008 | Perreault et al. |
| 7,361,168 B2 | 4/2008 | Makower et al. |
| 7,410,480 B2 | 8/2008 | Muni et al. |
| 7,419,497 B2 | 9/2008 | Muni et al. |
| 7,451,765 B2 | 11/2008 | Adler |
| 7,462,175 B2 | 12/2008 | Chang et al. |
| 7,500,971 B2 | 3/2009 | Chang et al. |
| 7,520,876 B2 | 4/2009 | Ressemann et al. |
| 7,544,192 B2 | 6/2009 | Eaton et al. |
| 7,559,925 B2 | 7/2009 | Goldfarb et al. |
| 7,594,928 B2 * | 9/2009 | Headley, Jr. ............... A61F 2/90 623/1.22 |
| 7,641,644 B2 | 1/2010 | Chang et al. |
| 7,641,688 B2 | 1/2010 | Lesh |
| 7,645,272 B2 | 1/2010 | Chang et al. |
| 7,651,696 B2 | 1/2010 | Bates |
| 7,654,997 B2 | 2/2010 | Makower et al. |
| 7,658,758 B2 | 2/2010 | Diaz et al. |
| 7,658,764 B2 | 2/2010 | Reitan et al. |
| 7,662,141 B2 | 2/2010 | Eaton et al. |
| 7,662,142 B2 | 2/2010 | Eaton et al. |
| 7,686,798 B2 | 3/2010 | Eaton et al. |
| 7,691,094 B2 | 4/2010 | Eaton et al. |
| 7,713,255 B2 | 5/2010 | Eaton et al. |
| 7,717,933 B2 | 5/2010 | Becker |
| 7,740,642 B2 | 6/2010 | Becker |
| 7,753,929 B2 | 7/2010 | Becker |
| 7,771,482 B1 | 8/2010 | Karmon |
| 7,951,130 B2 | 5/2011 | Eaton et al. |
| 7,951,131 B2 | 5/2011 | Eaton et al. |
| 7,951,132 B2 | 5/2011 | Eaton et al. |
| 7,951,133 B2 | 5/2011 | Eaton et al. |
| 7,951,134 B2 | 5/2011 | Eaton et al. |
| 7,951,135 B2 | 5/2011 | Eaton et al. |
| 8,025,635 B2 | 9/2011 | Eaton et al. |
| 8,088,120 B2 | 1/2012 | Worsoff |
| 8,109,918 B2 | 2/2012 | Eaton et al. |
| 8,192,450 B2 | 6/2012 | Gonzales et al. |
| 8,197,433 B2 | 6/2012 | Cohen |
| 8,303,640 B2 | 11/2012 | Hepworth et al. |
| 8,337,454 B2 | 12/2012 | Eaton et al. |
| 8,500,776 B2 | 8/2013 | Ebner |
| 8,535,707 B2 | 9/2013 | Arensdorf et al. |
| 8,585,730 B2 * | 11/2013 | Eaton ..................... A61F 5/08 606/199 |
| 8,585,731 B2 * | 11/2013 | Abbate .................. A61L 31/10 606/199 |
| 8,585,753 B2 | 11/2013 | Scanlon et al. |
| 8,721,591 B2 | 5/2014 | Chang et al. |
| 8,740,029 B2 | 6/2014 | Barnoski et al. |
| 8,740,839 B2 | 6/2014 | Eaton et al. |
| 8,740,929 B2 | 6/2014 | Gopferich et al. |
| 8,763,222 B2 * | 7/2014 | Abbate .................. B25B 27/10 29/243.56 |
| 8,802,131 B2 | 8/2014 | Arensdorf et al. |
| 8,858,974 B2 | 10/2014 | Eaton et al. |
| 8,986,341 B2 * | 3/2015 | Abbate .................. A61B 17/24 606/199 |
| 9,101,689 B2 * | 8/2015 | Hossainy ............... A61L 29/16 |
| 9,585,681 B2 | 3/2017 | Eaton et al. |
| 9,782,283 B2 * | 10/2017 | Abbate .................... A61F 2/95 |
| 10,010,651 B2 | 7/2018 | Eaton et al. |
| 10,471,185 B2 * | 11/2019 | Eaton .................... A61F 2/95 |
| 2002/0022048 A1 | 2/2002 | Bromberg et al. |
| 2002/0037919 A1 * | 3/2002 | Hunter .................. A61K 31/047 514/449 |
| 2002/0051793 A1 | 5/2002 | Drabick |
| 2002/0051845 A1 | 5/2002 | Mehta et al. |
| 2002/0055746 A1 * | 5/2002 | Burke ................... A61M 25/10 606/106 |
| 2002/0077693 A1 | 6/2002 | Barclay et al. |
| 2002/0111603 A1 | 8/2002 | Cheikh |
| 2002/0143387 A1 | 10/2002 | Soetikno et al. |
| 2002/0188344 A1 | 12/2002 | Bolea et al. |
| 2002/0198586 A1 | 12/2002 | Inoue |
| 2003/0033001 A1 | 2/2003 | Igaki |
| 2003/0040771 A1 * | 2/2003 | Hyodoh ................ D04C 1/06 606/200 |
| 2003/0040790 A1 | 2/2003 | Furst |
| 2003/0055488 A1 | 3/2003 | Igaki |
| 2003/0065346 A1 | 4/2003 | Evens et al. |
| 2003/0070682 A1 | 4/2003 | Wilson et al. |
| 2003/0105469 A1 | 6/2003 | Karmon |
| 2003/0109837 A1 | 6/2003 | McBride-Sakal |
| 2003/0125774 A1 | 7/2003 | Salo |
| 2003/0133877 A1 | 7/2003 | Levin |
| 2003/0135266 A1 | 7/2003 | Chew et al. |
| 2003/0135268 A1 | 7/2003 | Desai |
| 2003/0135970 A1 | 7/2003 | Thornton |
| 2003/0147954 A1 | 8/2003 | Yang et al. |
| 2003/0158598 A1 | 8/2003 | Ashton |

(56) References Cited

U.S. PATENT DOCUMENTS

| | | |
|---|---|---|
| 2003/0195459 A1 | 10/2003 | Shippert |
| 2003/0203030 A1 | 10/2003 | Ashton et al. |
| 2003/0206864 A1 | 11/2003 | Mangin |
| 2003/0209835 A1 | 11/2003 | Chun et al. |
| 2003/0236570 A1 | 12/2003 | Cook et al. |
| 2004/0043052 A1 | 3/2004 | Hunter et al. |
| 2004/0064083 A1 | 4/2004 | Becker |
| 2004/0064150 A1 | 4/2004 | Becker |
| 2004/0091543 A1 | 5/2004 | Bell et al. |
| 2004/0093062 A1 | 5/2004 | Glastra |
| 2004/0116958 A1 | 6/2004 | Gopferich et al. |
| 2004/0117004 A1 | 6/2004 | Osborne et al. |
| 2004/0133270 A1 | 7/2004 | Grandt |
| 2004/0176827 A1 | 9/2004 | Jacobson et al. |
| 2004/0236415 A1 | 11/2004 | Thomas |
| 2005/0038497 A1 | 2/2005 | Neuendorf et al. |
| 2005/0043783 A1 | 2/2005 | Amis et al. |
| 2005/0119725 A1 | 6/2005 | Wang et al. |
| 2005/0124560 A1 | 6/2005 | Sung et al. |
| 2005/0131460 A1 | 6/2005 | Gilford |
| 2005/0131514 A1 | 6/2005 | Hijlkema et al. |
| 2005/0131524 A1 | 6/2005 | Majercak et al. |
| 2005/0131525 A1 | 6/2005 | Hartley |
| 2005/0143817 A1 | 6/2005 | Hunter et al. |
| 2005/0163821 A1 | 7/2005 | Sung et al. |
| 2005/0165347 A1 | 7/2005 | Bardy |
| 2005/0203605 A1 | 9/2005 | Dolan |
| 2005/0229670 A1 | 10/2005 | Perreault |
| 2005/0240147 A1* | 10/2005 | Makower .......... A61B 17/3201 604/96.01 |
| 2005/0245906 A1 | 11/2005 | Makower et al. |
| 2006/0004286 A1 | 1/2006 | Chang et al. |
| 2006/0004323 A1 | 1/2006 | Chang et al. |
| 2006/0025849 A1 | 2/2006 | Kaplan et al. |
| 2006/0063973 A1 | 3/2006 | Makower et al. |
| 2006/0095066 A1 | 5/2006 | Chang et al. |
| 2006/0106361 A1 | 5/2006 | Muni et al. |
| 2006/0135981 A1 | 6/2006 | Lenker et al. |
| 2006/0142736 A1 | 6/2006 | Hissink et al. |
| 2006/0162722 A1 | 7/2006 | Boehm et al. |
| 2006/0167540 A1 | 7/2006 | Masters et al. |
| 2006/0210605 A1 | 9/2006 | Chang et al. |
| 2006/0247499 A1 | 11/2006 | Butler et al. |
| 2006/0265042 A1 | 11/2006 | Catanese, III et al. |
| 2006/0276871 A1 | 12/2006 | Lamson et al. |
| 2007/0055348 A1 | 3/2007 | Pryor |
| 2007/0079494 A1 | 4/2007 | Serrano |
| 2007/0100435 A1 | 5/2007 | Case et al. |
| 2007/0106366 A1 | 5/2007 | Delaloye et al. |
| 2007/0129751 A1 | 6/2007 | Muni et al. |
| 2007/0135789 A1 | 6/2007 | Chang et al. |
| 2007/0156211 A1 | 7/2007 | Ferren et al. |
| 2007/0156229 A1 | 7/2007 | Park |
| 2007/0162100 A1 | 7/2007 | Gabbay |
| 2007/0167682 A1 | 7/2007 | Goldfarb et al. |
| 2007/0179599 A1 | 8/2007 | Brodbeck et al. |
| 2007/0191922 A1 | 8/2007 | Hartley |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0227544 A1 | 10/2007 | Betsy et al. |
| 2007/0233225 A1 | 10/2007 | Rapacki et al. |
| 2007/0249896 A1 | 10/2007 | Goldfarb et al. |
| 2007/0250105 A1 | 10/2007 | Ressemann et al. |
| 2007/0269385 A1 | 11/2007 | Yun et al. |
| 2007/0270941 A1 | 11/2007 | Headley et al. |
| 2007/0282305 A1 | 12/2007 | Goldfarb et al. |
| 2007/0289677 A1 | 12/2007 | Ma et al. |
| 2007/0293726 A1 | 12/2007 | Goldfarb et al. |
| 2007/0293727 A1 | 12/2007 | Goldfarb et al. |
| 2007/0293946 A1 | 12/2007 | Gonzales et al. |
| 2007/0297186 A1 | 12/2007 | Hoover et al. |
| 2007/0299043 A1 | 12/2007 | Hunter et al. |
| 2008/0015540 A1 | 1/2008 | Muni et al. |
| 2008/0058295 A1 | 3/2008 | Chaudry |
| 2008/0058296 A1 | 3/2008 | Chaudry |
| 2008/0069858 A1 | 3/2008 | Weber |
| 2008/0077226 A1 | 3/2008 | Ouellette et al. |
| 2008/0077230 A1 | 3/2008 | Heaney et al. |
| 2008/0082162 A1 | 4/2008 | Boismier et al. |
| 2008/0085293 A1 | 4/2008 | Yang |
| 2008/0089952 A1 | 4/2008 | Hunter et al. |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097400 A1 | 4/2008 | Chang et al. |
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0097568 A1 | 4/2008 | Savage et al. |
| 2008/0097575 A1 | 4/2008 | Cottone |
| 2008/0097576 A1 | 4/2008 | Cottone et al. |
| 2008/0097580 A1 | 4/2008 | Dave |
| 2008/0097581 A1 | 4/2008 | Shanley |
| 2008/0097591 A1 | 4/2008 | Savage et al. |
| 2008/0103361 A1 | 5/2008 | Makower et al. |
| 2008/0103521 A1 | 5/2008 | Makower et al. |
| 2008/0103584 A1 | 5/2008 | Su et al. |
| 2008/0113000 A1 | 5/2008 | Hunter et al. |
| 2008/0119693 A1 | 5/2008 | Makower et al. |
| 2008/0125626 A1 | 5/2008 | Chang et al. |
| 2008/0125720 A1 | 5/2008 | Kim et al. |
| 2008/0132938 A1 | 6/2008 | Chang et al. |
| 2008/0145514 A1 | 6/2008 | Hunter et al. |
| 2008/0154237 A1 | 6/2008 | Chang et al. |
| 2008/0154250 A1 | 6/2008 | Makower et al. |
| 2008/0183128 A1 | 7/2008 | Morriss et al. |
| 2008/0195041 A1 | 8/2008 | Goldfarb et al. |
| 2008/0228085 A1 | 9/2008 | Jenkins et al. |
| 2008/0234720 A1 | 9/2008 | Chang et al. |
| 2008/0243140 A1 | 10/2008 | Gopferich et al. |
| 2008/0262468 A1 | 10/2008 | Clifford et al. |
| 2008/0262505 A1 | 10/2008 | Shahoian |
| 2008/0262508 A1 | 10/2008 | Clifford et al. |
| 2008/0262509 A1 | 10/2008 | Clifford et al. |
| 2008/0262510 A1 | 10/2008 | Clifford |
| 2008/0262593 A1 | 10/2008 | Ryan et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0306579 A1 | 12/2008 | Dolan et al. |
| 2008/0319424 A1 | 12/2008 | Muni et al. |
| 2009/0004272 A1 | 1/2009 | Gibson et al. |
| 2009/0004273 A1 | 1/2009 | Gibson et al. |
| 2009/0005763 A1 | 1/2009 | Makower et al. |
| 2009/0017090 A1* | 1/2009 | Arensdorf ............ A61K 9/0043 424/423 |
| 2009/0028923 A1 | 1/2009 | Muni et al. |
| 2009/0030274 A1 | 1/2009 | Goldfarb et al. |
| 2009/0035351 A1 | 2/2009 | Berglund et al. |
| 2009/0036968 A1 | 2/2009 | Hepworth et al. |
| 2009/0036974 A1 | 2/2009 | Penn et al. |
| 2009/0041824 A1 | 2/2009 | Zugates et al. |
| 2009/0056709 A1 | 3/2009 | Worsoff |
| 2009/0093823 A1 | 4/2009 | Chang et al. |
| 2009/0187098 A1 | 7/2009 | Makower et al. |
| 2009/0198179 A1 | 8/2009 | Abbate et al. |
| 2009/0198216 A1 | 8/2009 | Muni et al. |
| 2009/0240112 A1 | 9/2009 | Goldfarb et al. |
| 2009/0312745 A1 | 12/2009 | Goldfarb et al. |
| 2011/0004192 A1 | 1/2011 | Eaton et al. |
| 2011/0021986 A1 | 1/2011 | Zamboni |
| 2011/0167964 A1 | 7/2011 | Price |
| 2012/0101429 A1 | 4/2012 | Eaton et al. |
| 2013/0041463 A1 | 2/2013 | Ressemann |
| 2013/0066358 A1 | 3/2013 | Nalluri et al. |
| 2013/0231693 A1 | 9/2013 | Edgren et al. |
| 2013/0245608 A1 | 9/2013 | Muni et al. |
| 2013/0253567 A1 | 9/2013 | Edgren et al. |
| 2013/0281982 A1 | 10/2013 | Makower et al. |
| 2013/0304232 A1 | 11/2013 | Gries |
| 2014/0018839 A1 | 1/2014 | Renner et al. |
| 2014/0074065 A1 | 3/2014 | Muni et al. |
| 2014/0107615 A1 | 4/2014 | Doshi et al. |

(56) References Cited

U.S. PATENT DOCUMENTS

| | | | |
|---|---|---|---|
| 2014/0324025 | A1 | 10/2014 | Arensdorf et al. |
| 2015/0081017 | A1 | 3/2015 | Abbate et al. |
| 2016/0287854 | A1 | 10/2016 | Eaton et al. |
| 2017/0128093 | A1 | 5/2017 | Eaton et al. |
| 2019/0143087 | A1 | 5/2019 | Eaton et al. |
| 2020/0108181 | A1 | 4/2020 | Eaton et al. |
| 2020/0206391 | A1 | 7/2020 | Eaton et al. |

FOREIGN PATENT DOCUMENTS

| | | |
|---|---|---|
| JP | 2-500521 A | 2/1990 |
| JP | H04-25755 A | 2/1992 |
| JP | H-6-5800 Y2 | 2/1994 |
| JP | 6-506672 A | 7/1994 |
| JP | 6-329542 A | 11/1994 |
| JP | 8-117326 A | 5/1996 |
| JP | 2000-507630 A | 6/2000 |
| JP | 2001-506144 A | 5/2001 |
| JP | 2001-520188 A | 10/2001 |
| WO | WO-89/00839 A1 | 2/1989 |
| WO | WO-97/36949 A1 | 10/1997 |
| WO | WO-99/20261 A2 | 4/1999 |
| WO | WO-99/20261 A3 | 4/1999 |
| WO | WO-01/02024 A1 | 1/2001 |
| WO | WO-01/02024 C1 | 1/2001 |
| WO | WO-01/26658 A2 | 4/2001 |
| WO | WO-01/26658 A3 | 4/2001 |
| WO | WO-01/30411 A1 | 5/2001 |
| WO | WO-01/95834 A1 | 12/2001 |
| WO | WO-03/090818 A2 | 11/2003 |
| WO | WO-03/090818 A3 | 11/2003 |
| WO | WO-03/099359 A1 | 12/2003 |
| WO | WO-2004/016200 A1 | 2/2004 |
| WO | WO-2004/082525 A2 | 9/2004 |
| WO | WO-2004/082525 A3 | 9/2004 |
| WO | WO-2006/020180 A2 | 2/2006 |
| WO | WO-2006/020180 A3 | 2/2006 |
| WO | WO-2006/107957 A2 | 10/2006 |
| WO | WO-2006/107957 A3 | 10/2006 |
| WO | WO-2007/067451 A2 | 6/2007 |
| WO | WO-2007/067451 A3 | 6/2007 |
| WO | WO-2007/134215 A2 | 11/2007 |
| WO | WO-2007/134215 A3 | 11/2007 |
| WO | WO-2007/139668 A2 | 12/2007 |
| WO | WO-2007/139668 A3 | 12/2007 |
| WO | WO-2008/008389 A2 | 1/2008 |
| WO | WO-2008/008389 A3 | 1/2008 |
| WO | WO-2008/003533 A3 | 3/2008 |
| WO | WO-2008/033533 A2 | 3/2008 |
| WO | WO-2008/051453 A2 | 5/2008 |
| WO | WO-2008/051453 A3 | 5/2008 |
| WO | WO-2008/051881 A2 | 5/2008 |
| WO | WO-2008/051881 A3 | 5/2008 |
| WO | WO-2008/054655 A2 | 5/2008 |
| WO | WO-2008/054655 A3 | 5/2008 |
| WO | WO-2008/070996 A1 | 6/2008 |
| WO | WO-2008/154143 A2 | 12/2008 |
| WO | WO-2008/154143 A3 | 12/2008 |
| WO | WO-2009/079418 A2 | 6/2009 |
| WO | WO-2009/079418 A3 | 6/2009 |
| WO | WO-2010/014834 A1 | 2/2010 |
| WO | WO-2012/083594 A1 | 6/2012 |
| WO | WO-2012/107229 A1 | 8/2012 |
| WO | WO-2013/158337 A1 | 10/2013 |

OTHER PUBLICATIONS

Bolliger, C.T. et al. (1999). "Evaluation of a New Self-Expandable Silicone Stent in an Experimental Tracheal Stenosis," *Chest* 115:496-501.

Eberhart, R.C. et al. (2003). "Bioresorbable Polymeric Stents: Current Status and Future Promise," *J. Biomater. Sci. Polymer Edn.* 14(4):299-312.

Corrected Notice of Allowability dated May 2, 2018, for U.S. Appl. No. 14/081,974, filed Nov. 15, 2013, 2 pages.

European Search Report dated Feb. 21, 2011, for EP Patent Application No. 10 011 116.0 filed on Apr. 4, 2006, 8 pages.

European Search Report dated Feb. 21, 2011, for EP Patent Application No. 10 011 117.8 filed on Apr. 4, 2006, 8 pages.

European Search Report dated Feb. 21, 2011, for EP Patent Application No. 10 011 118.6 filed on Apr. 4, 2006, 8 pages.

Extended European Search Report dated Jun. 18, 2015, for EP Patent Application No. 08 863 327.6, filed on Jul. 16, 2010, 8 pages.

Extended European Search Report dated Jun. 26, 2015, for European Patent Application No. 09 803 604.9, filed on Jul. 30, 2009, 7 pages.

Final Office Action dated Jan. 8, 2009, for U.S. Appl. No. 10/800,162, filed Mar. 12, 2004, 5 pages.

Final Office Action dated Jul. 22, 2009, for U.S. Appl. No. 11/398,342, filed Apr. 4, 2006, 8 pages.

Final Office Action dated Jul. 8, 2010, for U.S. Appl. No. 11/398,342, filed Apr. 4, 2006, 7 pages.

Final Office Action dated Aug. 18, 2010, for U.S. Appl. No. 11/775,157, filed Jul. 9, 2007, 12 pages.

Final Office Action dated Jan. 27, 2011, for U.S. Appl. No. 12/479,794, filed Jun. 6, 2009, 6 pages.

Final Office Action dated Nov. 28, 2011, for U.S. Appl. No. 12/883,071, filed Sep. 15, 2010, 7 pages.

Final Office Action dated Mar. 1, 2012, for U.S. Appl. No. 12/270,695, filed Nov. 13, 2008, 26 pages.

Final Office Action dated Apr. 12, 2012, for U.S. Appl. No. 12/883,087, filed Sep. 15, 2010, 7 pages.

Final Office Action dated Apr. 16, 2012, for U.S. Appl. No. 12/334,373, filed Dec. 12, 2008, 7 pages.

Final Office Action dated May 29, 2012, for U.S. Appl. No. 12/334,382, filed Dec. 12, 2008, 7 pages.

Final Office Action dated Mar. 6, 2013, for U.S. Appl. No. 13/341,732, filed Dec. 30, 2011, 7 pages.

Final Office Action dated May 30, 2013, for U.S. Appl. No. 12/541,840, filed Aug. 14, 2009, 11 pages.

Final Office Action dated Sep. 10, 2013, for U.S. Appl. No. 12/334,395, filed Dec. 12, 2008, 8 pages.

Final Office Action dated May 5, 2014 for U.S. Appl. No. 12/883,087, filed Sep. 15, 2010, 10 pages.

Final Office Action dated May 19, 2014, for U.S. Appl. No. 13/341,732, filed Dec. 30, 2011, 7 pages.

Final Office Action dated Sep. 17, 2014, for U.S. Appl. No. 12/334,395, filed Dec. 12, 2008, 10 pages.

Final Office Action dated Feb. 12, 2015, for U.S. Appl. No. 13/341,732, filed Dec. 30, 2011, 8 pages.

Final Office Action dated Oct. 20, 2015, for U.S. Appl. No. 12/883,087, filed Sep. 15, 2010, 15 pages.

Final Office Action dated Feb. 8, 2016, for U.S. Appl. No. 12/334,395, filed Dec. 12, 2008, 18 pages.

Final Office Action dated Jun. 29, 2016, for U.S. Appl. No. 14/327,100, filed Jul. 9, 2014, 17 pages.

Final Office Action dated Sep. 16, 2016, for U.S. Appl. No. 14/081,974, filed Nov. 15, 2013, 12 pages.

Final Office Action dated Sep. 20, 2016, for U.S. Appl. No. 14/550,634, filed Nov. 21, 2014, 11 pages.

Final Office Action dated Nov. 30, 2017, for U.S. Appl. No. 14/081,974, filed Nov. 15, 2013, 11 pages.

Final Office Action dated Jan. 30, 2019, for U.S. Appl. No. 15/415,465, filed Jan. 25, 2017, 9 pages.

Final Office Action dated Jul. 15, 2020, for U.S. Appl. No. 15/415,465, filed Jan. 25, 2017, 15 pages.

Final Office Action dated Aug. 19, 2020, for U.S. Appl. No. 16/007,327, filed Jun. 13, 2018, 12 pages.

Hietala, E-M. et al. (2001). "Biodegradation of the Copolymeric Polylactide Stent," *Journal of Vascular Research* 38:361-369.

Hosemann, W. et al. (Mar. 2003, e-pub. Oct. 10, 2002). "Innovative Frontal Sinus Stent Acting as a Local Drug-Releasing System," *Eur. Arch. Otorhinolarynol.* 260:131-134.

Hughes, J.P. et al. (Apr. 2004). "Use of a Ureteric Pigtail Stent as a Self-Retaining Frontal Sinus Stent," *The Journal of Laryngology & Otology* 118:299-301.

(56) References Cited

OTHER PUBLICATIONS

International Search Report dated Feb. 24, 2006 for PCT Application No. PCT/US04/07828 filed Mar. 12, 2004, 1 page.
International Search Report dated Sep. 11, 2006, for PCT Patent Application No. PCT/US2006/012484 filed on Apr. 4, 2006, 6 pages.
International Search Report dated Mar. 19, 2008, for PCT Patent Application No. PCT/US2007/015813, filed on Jul. 10, 2007, 3 pages.
International Search Report dated Mar. 11, 2009, for PCT Application No. PCT/US2008/86178, filed on Dec. 12, 2008, 3 pages.
International Search Report dated Sep. 28, 2009, for PCT Application No. PCT/US2009/052287, filed on Jul. 30, 2009, 2 pages.
Laaksovirta, S. (Aug. 22, 2003). *Biodegradable, Self-Reinforced, Self-Expandable Lactic and Glycolic Acid (SR-PLGA 80/20) Copolymer Spiral Prostatic Stent: Analysis of Mechanical and Biological Properties and Clinical Results*, Academic Dissertation, Medical School of the University of Tampere, 79 pages.
Lapchenko, A.S. et al. (Jun. 1996). "Polyphosphazene Prosthesis of the Frontonasal Bypass in Surgical Treatment of Acute and Chronic Inflammation of the Frontal Sinuses," *Vestnik Otorinolarinoloaii*. 2 pages.
Lavigne, F. et al. (May 2002). "Intrasinus Administration of Topical Budesonide to Allergic Patients With Chronic Rhinosinusitis Following Surgery," *The Laryngoscope* 112, 7 pages.
Min, Y-G. et al. (1995). "Application of Polylactic Acid Polymer in the Treatment of Acute Maxillary Sinusitis in Rabbits," *Acta Otolaryngol*. 115:548-552.
Min, Y-G. et al. (Aug. 1995). "Mucociliary Activity and Histopathology of Sinus Mucosa in Experimental Maxillary Sinusitis: A Comparison of Systemic Administration of Antibiotic and Antibiotic Delivery by Polylactic Acid Polymer," *The Laryngoscope* 105:835-842.
Mirza, S. et al. (Dec. 2000). "A Simple and Effective Frontal Sinus Stent," *The Journal of Laryngology & Otology* 114:955-956.
Mitty, H. et al. (1988). "Experience with a New Ureteral Stent Made of a Biocompatible Copolymer," *Radiology* 168:557-559.
Murphy, J.G. et al. (1992). "Percutaneous Polymeric Stents in Porcine Coronary Arteries: Initial Experience With Polyethylene Terephthalate Stents," *Circulation* 86:1596-1604.
Nguyen, K.T. et al. (2004). "Biomaterials and Stent Technology," Chapter 5 in *Tissue Engineering and Novel Delivery Systems*, 24 pages.
Non-Final Office Action dated Jun. 6, 2008, for U.S. Appl. No. 10/800,162, filed Mar. 12, 2004, 5 pages.
Non-Final Office Action dated Nov. 25, 2008, for U.S. Appl. No. 11/398,342, filed Apr. 4, 2006, 10 pages.
Non-Final Office Action dated Sep. 22, 2009, for U.S. Appl. No. 12/419,927, filed Apr. 7, 2009, 4 pages.
Non-Final Office Action dated Sep. 22, 2009, for U.S. Appl. No. 12/419,943, filed Apr. 7, 2009, 5 pages.
Non-Final Office Action dated Sep. 22, 2009, for U.S. Appl. No. 12/419,930, filed Apr. 7, 2007, 4 pages.
Non-Final Office Action dated Sep. 22, 2009, for U.S. Appl. No. 12/419,937, filed Apr. 7, 2009, 4 pages.
Non-Final Office Action dated Sep. 22, 2009, for U.S. Appl. No. 12/419,925, filed Apr. 7, 2009, 4 pages.
Non-Final Office Action dated Nov. 13, 2009, for U.S. Appl. No. 11/398,342, filed Apr. 4, 2006, 9 pages.
Non-Final Office Action dated Dec. 9, 2009, for U.S. Appl. No. 11/775,157, filed Jul. 9, 2007, 12 pages.
Non-Final Office Action dated Jul. 1, 2010, for U.S. Appl. No. 12/479,794, filed Jun. 6, 2009, 5 pages.
Non-Final Office Action dated Sep. 10, 2010, for U.S. Appl. No. 12/437,374, filed May 7, 2009, 8 pages.
Non-Final Office Action dated Nov. 12, 2010, for U.S. Appl. No. 11/398,342, filed Apr. 4, 2006, 8 pages.
Non-Final Office Action dated Nov. 23, 2010, for U.S. Appl. No. 12/258,277, filed Oct. 24, 2008, 9 pages.
Non-Final Office Action dated Nov. 23, 2010, for U.S. Appl. No. 12/258,282, filed Oct. 24, 2008, 7 pages.
Non-Final Office Action dated Nov. 24, 2010, for U.S. Appl. No. 12/883,090, filed Sep. 15, 2010, 7 pages.
Non-Final Office Action dated Nov. 24, 2010, for U.S. Appl. No. 12/883,056, filed Sep. 15, 2010, 7 pages.
Non-Final Office Action dated Nov. 24, 2010, for U.S. Appl. No. 12/883,079, filed Sep. 15, 2010, 8 pages.
Non-Final Office Action dated Mar. 22, 2011, for U.S. Appl. No. 12/883,071, filed Sep. 15, 2010, 8 pages.
Non-Final Office Action dated May 13, 2011, for U.S. Appl. No. 12/883,087, filed Sep. 15, 2010, 7 pages.
Non-Final Office Action dated Jun. 14, 2011, for U.S. Appl. No. 12/437,374, filed May 7, 2009, 8 pages.
Non-Final Office Action dated Jun. 21, 2011, for U.S. Appl. No. 12/270,695, filed Nov. 13, 2008, 24 pages.
Non-Final Office Action dated Jul. 13, 2011, for U.S. Appl. No. 12/334,373, filed Dec. 12, 2008, 8 pages.
Non-Final Office Action dated Sep. 26, 2011, for U.S. Appl. No. 12/334,382, filed Dec. 12, 2008, 7 pages.
Non-Final Office Action dated May 11, 2012, for U.S. Appl. No. 12/883,071, filed Sep. 15, 2010, 7 pages.
Non-Final Office Action dated Jun. 7, 2012, for U.S. Appl. No. 12/334,395, filed Dec. 12, 2008, 7 pages.
Non-Final Office Action dated Oct. 18, 2012, for U.S. Appl. No. 12/541,840, filed Aug. 14, 2009, 10 pages.
Non-Final Office Action dated Mar. 15, 2013, for U.S. Appl. No. 12/512,855, filed Jul. 30, 2009, 10 pages.
Non-Final Office Action dated Sep. 12, 2013 for U.S. Appl. No. 13/341,732, filed Dec. 30, 2011, 5 pages.
Non-Final Office Action dated Sep. 23, 2013, for U.S. Appl. No. 12/883,087, filed Sep. 15, 2010, 7 pages.
Non-Final Office Action dated Feb. 27, 2014, for U.S. Appl. No. 12/270,695, filed Nov. 13, 2008, 7 pages.
Non-Final Office Action dated Apr. 16, 2014, for U.S. Appl. No. 12/334,395, filed Dec. 12, 2008, 9 pages.
Non-Final Office Action dated Jun. 12, 2014, for U.S. Appl. No. 14/082,010, filed Nov. 15, 2013, 6 pages.
Non-Final Office Action dated Sep. 23, 2014, for U.S. Appl. No. 13/341,732, filed Dec. 30, 2011, 8 pages.
Non-Final Office Action dated Mar. 20, 2015, for U.S. Appl. No. 12/883,087, filed Sep. 15, 2010, 11 pages.
Non-Final Office Action dated May 8, 2015, for U.S. Appl. No. 12/334,395, filed Dec. 12, 2008, 11 pages.
Non-Final Office Action dated Sep. 10, 2015, for U.S. Appl. No. 13/341,732, filed Dec. 30, 2011, 6 pages.
Non-Final Office Action dated Nov. 12, 2015, for U.S. Appl. No. 14/327,100, filed Jul. 9, 2014, 12 pages.
Non-Final Office Action dated Feb. 5, 2016, for U.S. Appl. No. 12/883,087, filed Sep. 15, 2010, 12 pages.
Non-Final Office Action dated Feb. 5, 2016, for U.S. Appl. No. 14/081,974, filed Nov. 15, 2013, 12 pages.
Non-Final Office Action dated Apr. 28, 2016, for U.S. Appl. No. 14/550,634, filed Nov. 21, 2014, 10 pages.
Non-Final Office Action dated Aug. 11, 2016, for U.S. Appl. No. 12/334,395, filed Dec. 12, 2008, 12 pages.
Non-Final Office Action dated Mar. 20, 2017, for U.S. Appl. No. 14/298,715, filed Jun. 6, 2014, 7 pages.
Non-Final Office Action dated Jun. 29, 2017, for U.S. Appl. No. 14/081,974, filed Nov. 15, 2013, 15 pages.
Non-Final Office Action dated Dec. 13, 2017, for U.S. Appl. No. 15/062,616, filed Mar. 7, 2016, 13 pages.
Non-Final Office Action dated Apr. 2, 2018, for U.S. Appl. No. 15/415,465, filed Jan. 25, 2017, 11 pages.
Non-Final Office Action dated Jul. 25, 2019, for U.S. Appl. No. 16/021,659, filed Jun. 28, 2018, 21 pages.
Non-Final Office Action dated Jan. 17, 2020, for U.S. Appl. No. 15/415,465, filed Jan. 25, 2017, 14 pages.
Non-Final Office Action dated Feb. 10, 2020, for U.S. Appl. No. 16/007,327, filed Jun. 13, 2018, 10 pages.
Notice of Allowance dated Dec. 23, 2009, for U.S. Appl. No. 12/419,925, filed Apr. 7, 2009, 2 pages.

(56) References Cited

OTHER PUBLICATIONS

Notice of Allowance dated Dec. 23, 2009, for U.S. Appl. No. 12/419,943, filed Apr. 7, 2009, 2 pages.
Notice of Allowance dated Dec. 24, 2009, for U.S. Appl. No. 12/419,927, filed Apr. 7, 2009, 2 pages.
Notice of Allowance dated Jan. 19, 2010, for U.S. Appl. No. 12/419,930, filed Apr. 7, 2009, 2 pages.
Notice of Allowance dated Feb. 2, 2010, for U.S. Appl. No. 12/419,937, filed Apr. 7, 2009, 2 pages.
Notice of Allowance dated Mar. 18, 2011, for U.S. Appl. No. 12/258,277, filed Oct. 24, 2008, 7 pages.
Notice of Allowance dated Mar. 21, 2011, for U.S. Appl. No. 12/258,282, filed Oct. 24, 2008, 8 pages.
Notice of Allowance dated Mar. 21, 2011, for U.S. Appl. No. 12/883,059, filed Sep. 15, 2010, 10 pages.
Notice of Allowance dated Mar. 23, 2011, for U.S. Appl. No. 12/883,079, filed Sep. 15, 2010, 9 pages.
Notice of Allowance dated Mar. 25, 2011 for U.S. Appl. No. 12/883,090, filed Sep. 15, 2010, 8 pages.
Notice of Allowance dated Mar. 25, 2011, for U.S. Appl. No. 12/883,056, filed Sep. 15, 2010, 8 pages.
Notice of Allowance dated Jul. 13, 2011, for U.S. Appl. No. 11/398,342, filed Apr. 4, 2006, 7 pages.
Notice of Allowance dated Nov. 9, 2011, for U.S. Appl. No. 12/479,794, filed Jun. 6, 2009, 7 pages.
Notice of Allowance dated Aug. 20, 2012, for U.S. Appl. No. 12/437,374, filed May 7, 2009, 8 pages.
Notice of Allowance dated Nov. 2, 2012, for U.S. Appl. No. 11/775,157, filed Jul. 9, 2007, 8 pages.
Notice of Allowance dated May 22, 2013, for U.S. Appl. No. 11/775,157, filed Jul. 9, 2007, 10 pages.
Notice of Allowance dated Jul. 15, 2013, for U.S. Appl. No. 12,334,382, filed Dec. 12, 2008, 9 pages.
Notice of Allowance dated Jul. 30, 2013, for U.S. Appl. No. 12/334,373, filed Dec. 12, 2008, 10 pages.
Notice of Allowance dated Sep. 19, 2013, for U.S. Appl. No. 12/883,071, filed Sep. 15, 2010, 6 pages.
Notice of Allowance dated Nov. 27, 2013, for U.S. Appl. No. 12/512,855, filed Jul. 30, 2009, 9 pages.
Notice of Allowance dated Jan. 21, 2014, for U.S. Appl. No. 12/883,071, filed Sep. 15, 2010, 6 pages.
Notice of Allowance dated Feb. 19, 2014, for U.S. Appl. No. 12/512,855, filed Jul. 30, 2009, 7 pages.
Notice of Allowance dated Apr. 8, 2014, for U.S. Appl. No. 12/541,840, filed Aug. 14, 2009, 8 pages.
Notice of Allowance (Corrected) dated May 29, 2014, for U.S. Appl. No. 12/512,855, filed Jul. 30, 2009, 4 pages.
Notice of Allowance dated Jun. 12, 2014, for U.S. Appl. No. 12/270,695, filed Nov. 13, 2008, 7 pages.
Notice of Allowance dated Nov. 12, 2014, for U.S. Appl. No. 14/082,010, filed Nov. 15, 2013, 5 pages.
Notice of Allowance dated Feb. 17, 2015, for U.S. Appl. No. 14/082,010, filed Nov. 15, 2013, 5 pages.
Notice of Allowance dated Nov. 18, 2016, for U.S. Appl. No. 14/298,715, filed Jun. 6, 2014, 8 pages.
Notice of Allowance dated Jun. 20, 2017, for U.S. Appl. No. 14/298,715, filed Jun. 6, 2014, 5 pages.
Notice of Allowance dated Apr. 6, 2018, for U.S. Appl. No. 14/081,974, filed Nov. 15, 2013, 9 pages.
Notice of Allowance dated Sep. 12, 2019, for U.S. Appl. No. 16/021,659, filed Jun. 28, 2018, 10 pages.

Nuutinen, J-P. et al. (2002). "Mechanical Properties and in vitro Degradation of Bioresorbable Knitted Stents," *J. Biomater. Sci. Polymer Edn.* 13(12):1313-1323.
Nuutinen, J-P. et al. (2003). "Theoretical and Experimental Evaluation of the Radial Force of Self-Expanding Braided Bioabsorbable Stents," *J. Biomater. Sci. Polymer Edn.* 14(7):677-687.
Parviainen, M. et al. (2000). "A New Biodegradable Stent for the Pancreaticojejunal Anastomosis After Pancreaticoduodenal Resection: in Vitro Examination and Pilot Experiences in Humans," *Pancreas* 21 (1 ):14-21.
Piskunov, S.Z. et al. (May-Jun. 1989). "Application of Drugs Based on Polymers in the Treatment of Acute and Chronic Maxillary Sinusitis," *Vestnik Otorinolaringologii* (3)33-35.
Piskunov, S. et al. (1993). "The Prolongation of Drug Action in the Treatment of Diseases of the Nose and Paranasal Sinuses," *Rhinology* 31:33-36.
Roumestan, C. et al. (2003). "Fluticasone Propionate and Mometasone Furoate Have Equivalent Transcriptional Potencies," *Clinical and Experimental Allergy* 33: 895-901.
Shikani, A.H. (Aug. 1996). "Use of Antibiotics for Expansion of the Merocel® Packing Following Endoscopic Sinus Surgery," *ENT Journal* 75(8):524-528.
Su, S-H. et al. (2003). "Expandable Bioresorbable Endovascular Stent. I. Fabrication and Properties," *Annals of Biomedical Engineering* 31:667-677.
Supplementary European Search Report dated Nov. 9, 2010, for European Patent Application No. 04 720 509.1, filed on Mar. 12, 2004, 3 pages.
Tamai, H. et al. (1999). "A Biodegradable Ploy-/-lactic Acid Coronary Stent in the Porcine Coronary Artery," *Journal of Interventional Cardiology* 12(6):443-450.
Thierry, B. et al. (Nov./Dec. 2003, e-pub. Oct. 7, 2003) "Bioactive Coatings of Endovascular Stents Based on Polyelectrolyte Multilayers," *Biomacromolecules* 4(6):1564-1571.
Third Party Submission under 37 CFR 1.290 submitted Oct. 11, 2014, against U.S. Appl. No. 14/081,974, filed Nov. 15, 2013, 8 pages.
Toffel, P.H. (Mar. 2001). "The Balanced Philosophy of Secure Multimodal Endoscopic Sinus Surgery with Adjunct Use of Middle Meatal Stenting and Middle Turbinate Modification," *Operative Techniques in Otolaryngology--Head and Neck Surgery* 12(1):40-45.
Vogt, F. et al. (2004, e-pub. Jul. 20, 2004). "Long-Term Assessment of a Novel Biodegradable Paclitaxel-Eluting Coronary Polylactide Stent," *European Heart Journal* 25:1330-1340.
Written Opinion of the International Searching Authority dated Sep. 11, 2006, for PCT Patent Application No. PCT/US2006/012484, filed on Apr. 4, 2006, 11 pages.
Written Opinion of the International Searching Authority dated Sep. 28, 2009, for PCT Application No. PCT/US2009/052287, filed on Jul. 30, 2009, 9 pages.
Written Opinion of the International Searching Authority dated Feb. 24, 2006 for PCT Application No. PCT/US04/07828, filed Mar. 12, 2004, 3 pages.
Written Opinion of the International Searching Authority dated Mar. 19, 2008, for PCT Patent Application No. PCT/US2007/015813, filed on Jul. 10, 2007, 7 pages.
Written Opinion of the International Searching Authority dated Apr. 16, 2009, for PCT Application No. PCT/US2008/86718, filed on Dec. 12, 2008, 13 pages.
Extended European Search Report dated Feb. 8, 2021, for European Patent Application No. 20 203 807.1, filed on Jul. 30, 2009, 9 pages.

\* cited by examiner

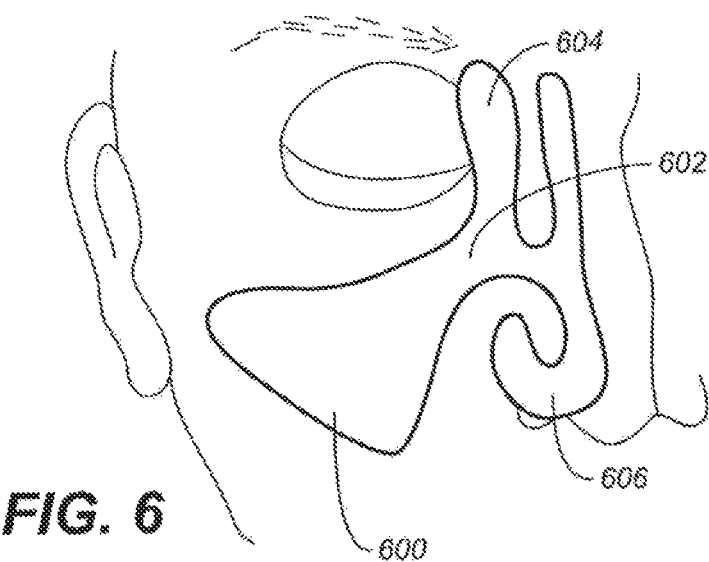
FIG. 6
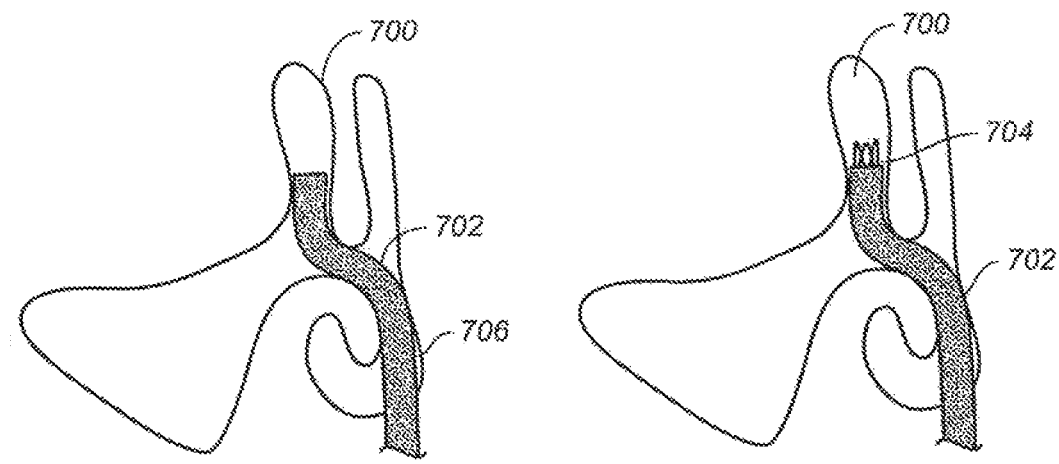
FIG. 7A  FIG. 7B
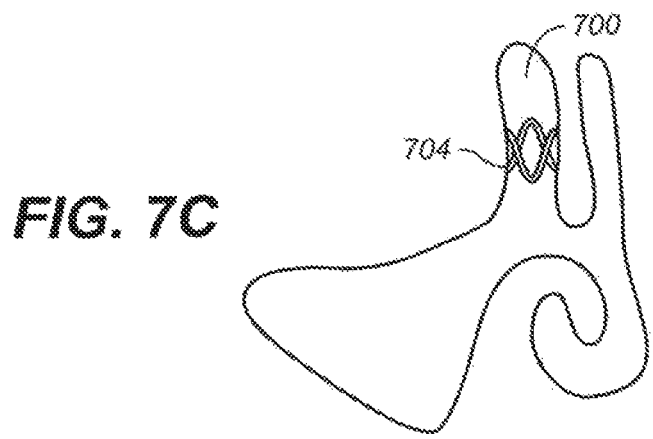
FIG. 7C

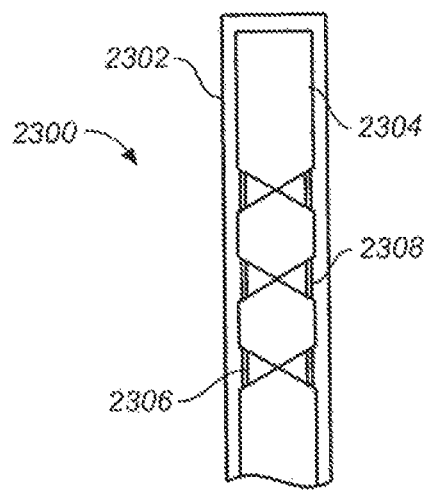
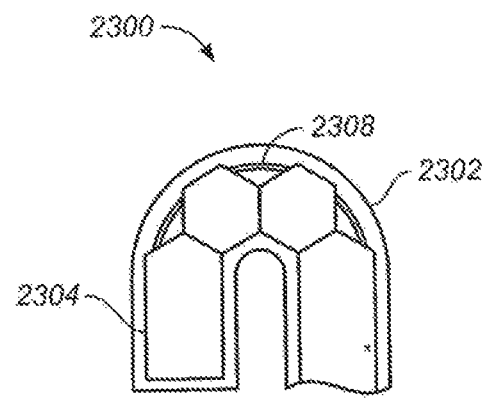
FIG. 23A     FIG. 23B
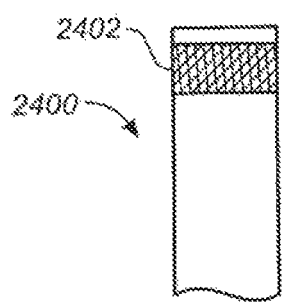
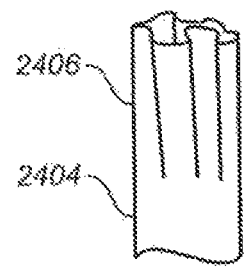
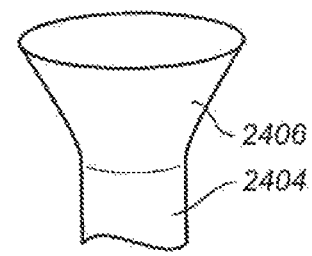
FIG. 24A     FIG. 24B     FIG. 24C
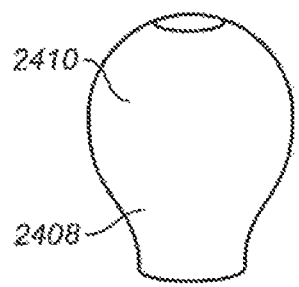
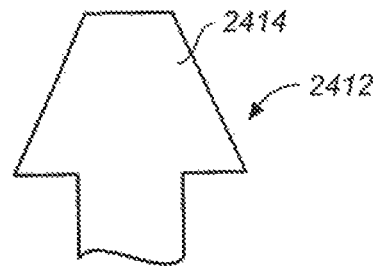
FIG. 24D     FIG. 24E

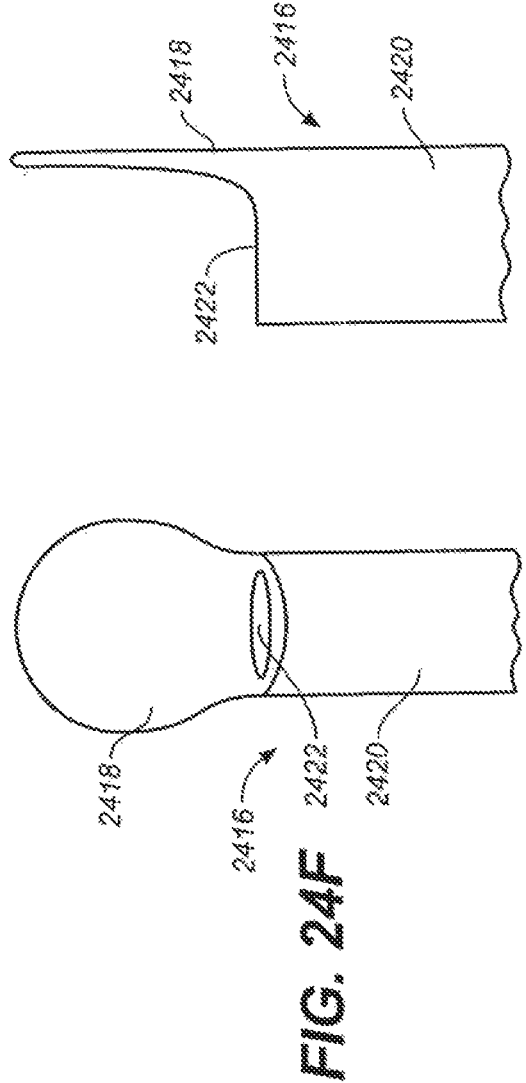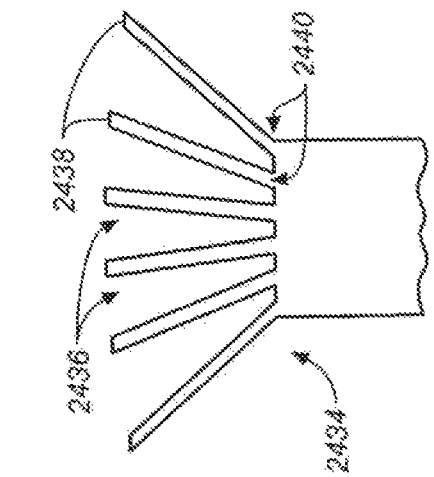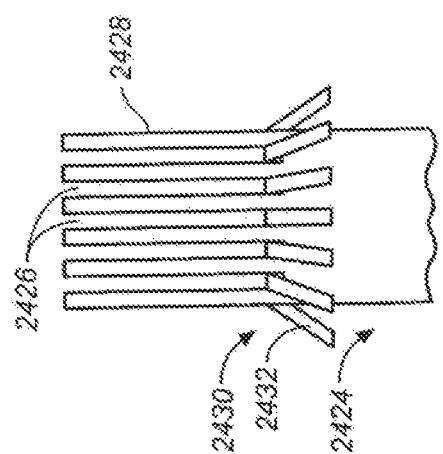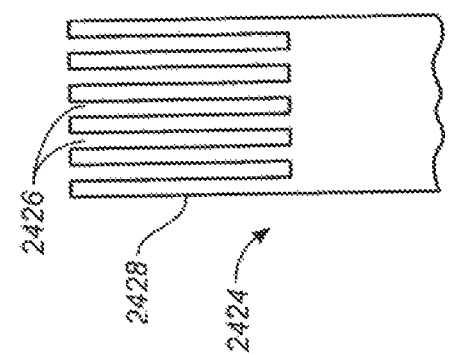
FIG. 24F  FIG. 24G  FIG. 24H  FIG. 24I  FIG. 24J

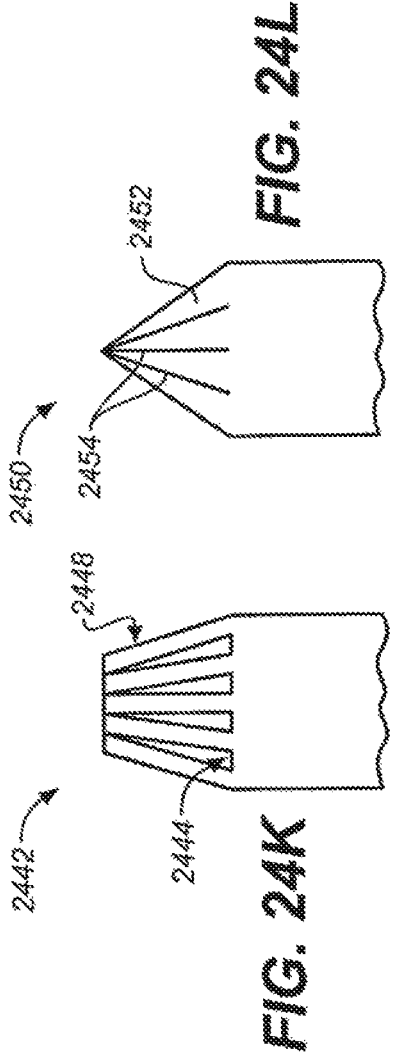
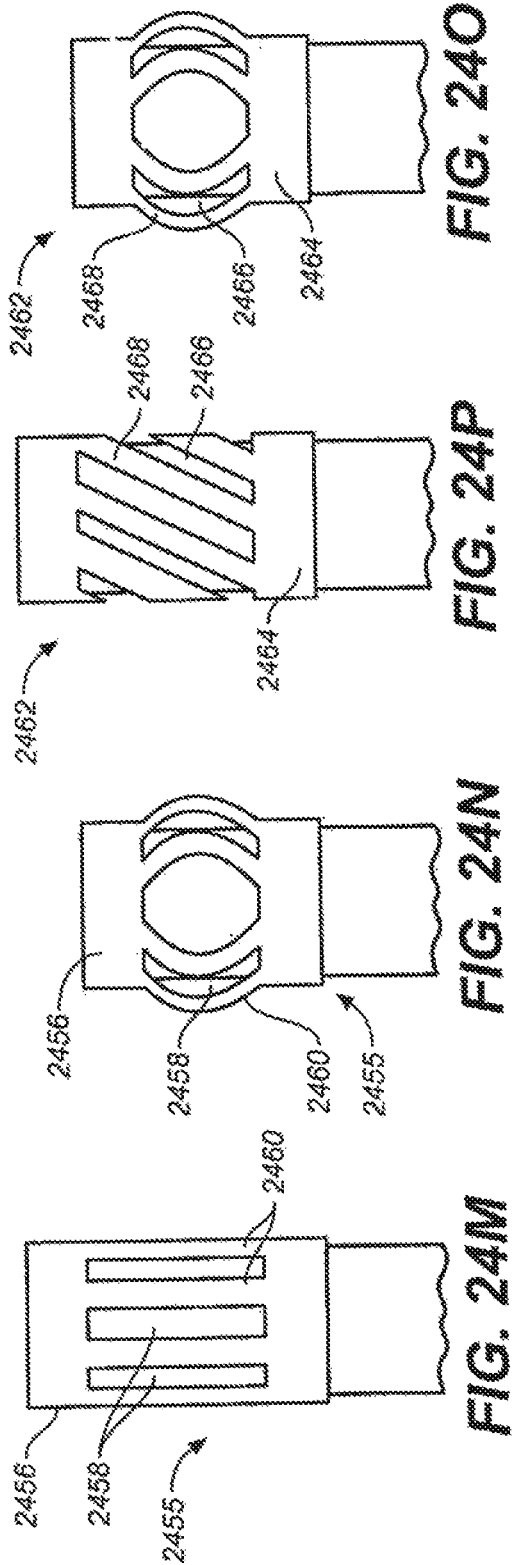

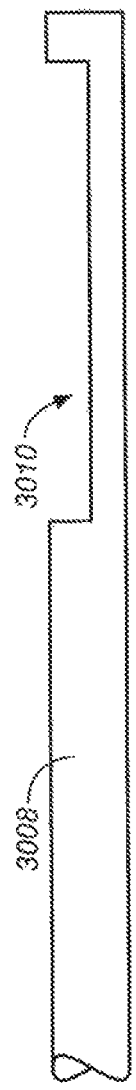
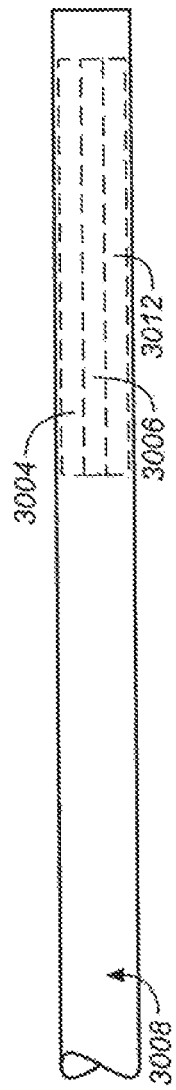
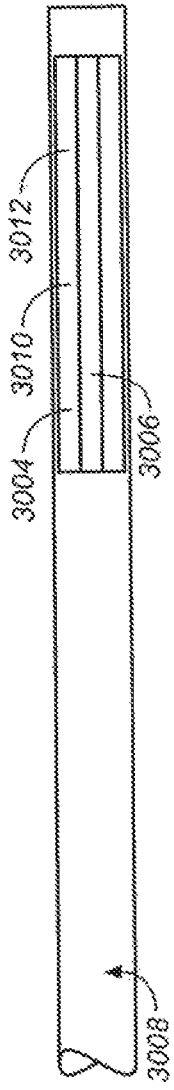
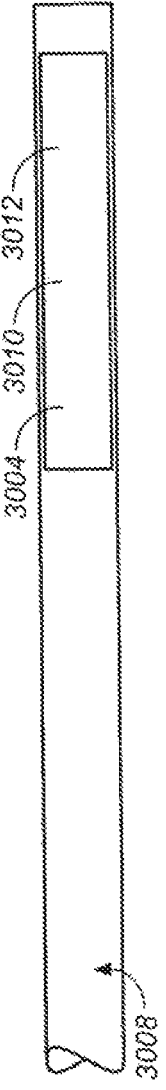
FIG. 30B
FIG. 30C
FIG. 30D
FIG. 30E
FIG. 30F

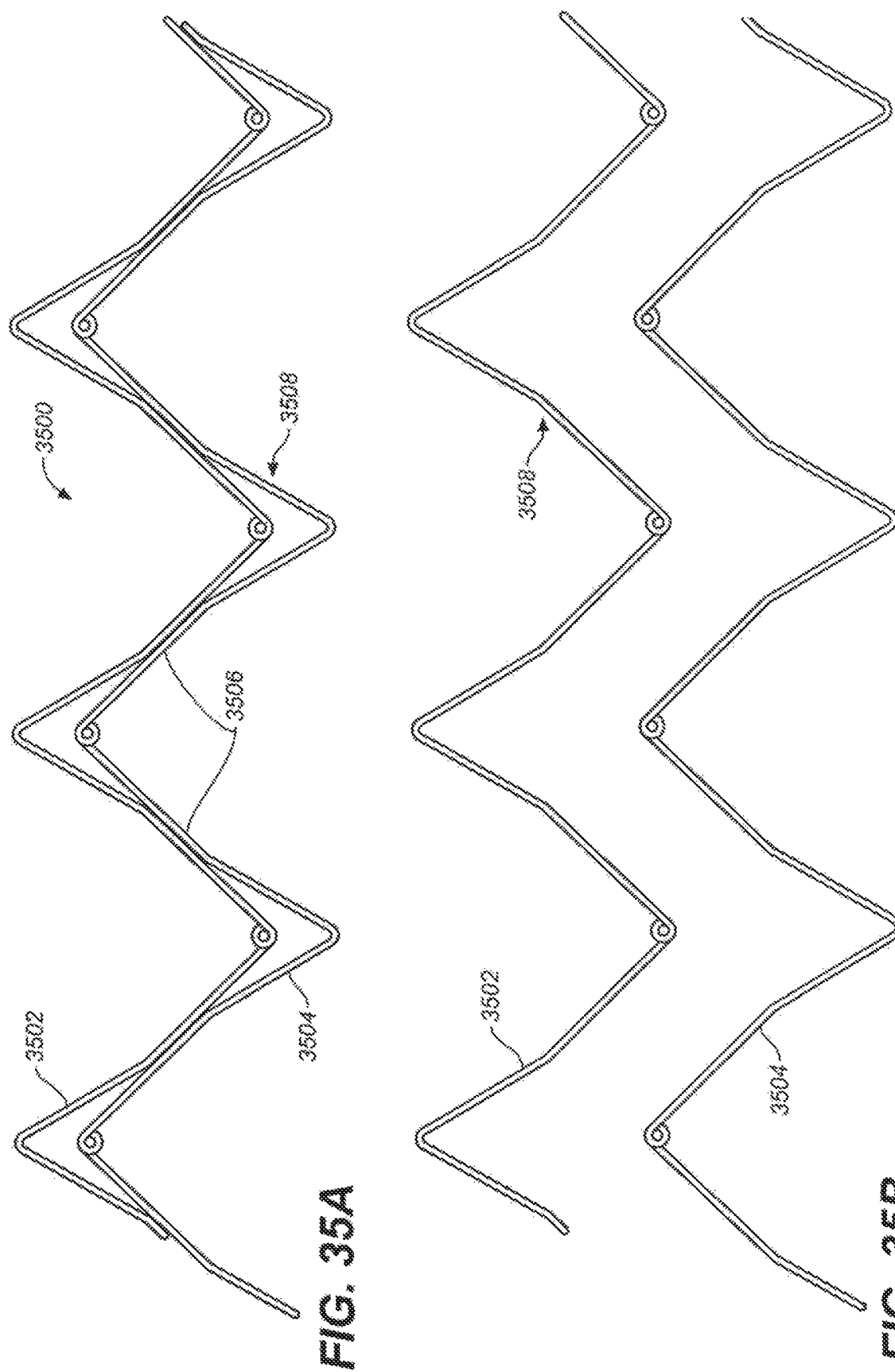

SELF-EXPANDING DEVICES AND METHODS THEREFOR

RELATED APPLICATIONS

This application is a continuation of U.S. patent application Ser. No. 16/727,345, filed on Dec.26, 2019, which is a continuation of U.S. patent application Ser. No. 16/588,294, filed on Sep. 30, 2019, which is a continuation of U.S. patent application Ser. No. 16/021,659, filed on Jun. 28, 2018, now issued as U.S. Pat. No. 10,471,185, which is a continuation of U.S. patent application Ser. No. 14/081,974, filed on Nov. 15, 2013, now issued as U.S. Pat. No. 10,010,651, which is a continuation of U.S. patent application Ser. No. 12/334,373, filed on Dec. 12, 2008, now issued as U.S. Pat. No. 8,585,730, which claims priority to U.S. Provisional Application Ser. No. 61/058,803, filed on Jun. 4, 2008, and to U.S. Provisional Application Ser. No. 61/014,653, filed on Dec. 18, 2007, each of which is hereby incorporated by reference in its entirety.

FIELD

The present invention relates generally to delivery devices for delivering one or more implants to or near a paranasal sinus. At least a portion of these implants may be self-expanding, and at least a portion of the implants may be biodegradable and configured for drug delivery. Methods of using the delivery devices are also described here.

BACKGROUND

Self-expanding devices may be useful in maintaining, opening or dilating bodily structures such as veins, arteries, ureters, urethras, hollow-body organs, nasal passages, sinus cavities, and the like. Given the variety of benefits these devices may provide, additional self-expanding devices would be desirable. In particular, self-expanding devices that may offer advantageous physical and/or functional characteristics would be desirable. Additionally, delivery devices for delivering self-expanding devices and other implants would be desirable.

BRIEF SUMMARY

Described here are self-expanding devices, and methods of using and making them. The devices may be useful in a variety of locations within the body for a number of different uses. In some variations, the devices have a first compressed configuration enabling low profile delivery through a delivery device, a second expanded configuration for apposition against tissue, and comprise either a single continuous filament or at least two non-intersecting filaments. In other variations, the device comprises two or more filaments that are intersecting, joined, or contacting (e.g., in an overlapping, twisted, knotted, or bonded fashion). At least a portion of these devices typically comprises a polymer, e.g., a biodegradable polymer. In instances where a biodegradable polymer is used, the device (or a portion thereof) is typically capable of biodegrading over a predetermined period of time. The polymer may be any suitable or useful polymer, and the device may include or comprise any additional suitable materials. In some variations, for example, the devices comprise at least one metallic filament, at least one flexible section, or the like.

In some variations, the devices are suitable for drug delivery. In these variations, the polymer or at least a portion of the device may be coated or impregnated with a drug, be at least partially coated with a drug eluting layer, or comprise one or more drug depots. A drug may be configured to be released from the drug eluting layer or depot over a period of time, e.g., from about 5 days to about 120 days, or even longer. Any suitable drug or agent may be used, and in some variations more than one drug or agent is used. For example, multiple drugs may be configured to be released from a single drug eluting layer, or multiple drug eluting layers may be configured to release multiple drugs. The drug or agent may be an anti-inflammatory agent, an anti-allergen, an anti-cholinergic agent, an antihistamine, an anti-infective, an anti-platelet agent, an anti-coagulant, an anti-thrombic agent, an anti-scarring agent, an anti-proliferative agent, a chemotherapeutic agent, an anti-neoplastic agent, a pro-healing agent, a decongestant, a vitamin, a hypersomolar agent, an immunomodulator, an immunosuppressive agent, or combinations and mixtures thereof. In some variations, the drug is an anti-inflammatory, e.g., mometasone furoate. The drug eluting layer may be discontinuous and may comprise a release rate modifier. In some variations, the release rate modifier is a polyethylene glycol, e.g., PEG 6000.

Some of the devices described here have a size and configuration adapted for implantation within one or more sinus cavities or sinus regions, e.g., an ethmoid sinus cavity, a maxillary sinus cavity, a frontal sinus cavity, a sphenoid sinus cavity, the osteomeatal complex, the nasal passage, or combinations thereof. However, as described above, the devices may be useful within any hollow-body organ (throat, biliary duct, organ or passageway of the excretory system, etc.) or cavity or even within the vasculature.

In some variations, self-expanding devices are described having a first compressed configuration enabling low profile delivery through a delivery device, and a second expanded configuration for apposition against tissue, where at least a portion of the device comprises a biodegradable material and the device is formed into a shape having a series of peaks and valleys. In other variations, the device is formed into a shape having at least two series of peaks and/or valleys. In some variations, the shape of the device comprises a diamond-shaped, arrowhead-shaped, or rectangular pattern. Some variations further comprise junctions.

At least one of the peaks and valleys may have a loop at an end thereof. The loop may or may not be coated or impregnated with a drug or with a polymer for delivery of a drug therefrom. When a loop is used, it may be configured to provide for even distribution of bending stresses (e.g., stresses applied to the device when the device is placed in its first configuration and loaded into a delivery device). The loop may comprise or define an eyelet for passage of a suture therethrough, e.g., so that when the suture is pulled, the device collapses from its second configuration to its first configuration. The angle defined by the loop apex may be of any suitable degree, for example, it may be from about 30° to about 150° when the device is in its expanded configuration. In some variations, the angle is about 75°.

In some variations, a portion of the devices or a portion of the polymer is at least partially coated with a drug or drug eluting layer. The polymer and the drug eluting layer may comprise PLG with different molar ratios of lactide to glycolide. As with the devices described just above, any suitable drug or agent may be delivered and selection of such a drug or agent is largely determined based upon the desired use of the device. In addition, as described above, multiple drugs may be configured to be released over multiple periods of time from one or more drug eluting layers. In variations where multiple drugs are released, each drug may or may not be released simultaneously with other drugs. In some variations, the devices are useful to treat inflammation, and the drug eluting layer comprises an anti-inflammatory agent.

In other variations, devices are described here having a first compressed configuration enabling low profile delivery through a delivery device, and a second expanded configuration for apposition against a tissue wall, where the device has a geometry that facilitates its conformation against an irregular tissue wall. In these variations the device defines a lumen (having any suitable cross-sectional geometry) in its expanded configuration, which is sized to promote clearance of one or more fluids therethrough (e.g., mucus or other drainage, water, saline, or other irrigation fluid, and the like).

In still other variations, devices are described here having both unexpanded and expanded configurations, and where the device comprises at least two component pieces, or a single continuous filament that is wound upon itself. The component pieces may be separate filaments, separate devices, a combination thereof, or the like. In some of these variations the at least two component pieces are formed into a shape having a series of peaks and valleys. The component pieces may or may not be joined together, and in variations where they are joined, they may be joined using welding (e.g., heat welding, ultrasonic welding, tacking, staking, and the like), adhesives (glues, adhesive polymers, and the like), polymers (e.g., low melting-temperature polymers and the like), sutures, clamps, clips, other mechanical fasteners, chemical bonding, or some combination thereof. They may also be joined by interweaving portions of the component pieces. In some variations, the at least two component pieces comprise at least two separate expandable devices, and in this way, for example, the overall device may be modular.

In yet other variations, self-expanding biodegradable devices are described having sizes and configurations adapted for implantation within one or more sinus regions or sinus cavities or ostiums thereof, where the devices comprise one or more polymer filaments and have shapes that approximate a repeating diamond-shaped pattern. The diamond-shaped pattern is typically defined by a series of repeating peaks and valleys. In some of these variations, the device may comprise at least two component pieces (devices or filaments, etc.). In some variations the biodegradable device comprises poly(lactic acid-co-glycolic acid). As with the devices described above, the devices of these variations may comprise junctions formed in any suitable manner and having any suitable configuration.

Methods of treating one or more sinus cavities, or one or more locations where sinus cavities have been removed, are also described here. In general, these methods comprise advancing a device adjacent to a sinus cavity and delivering at least a portion of the device within the sinus cavity. The devices are typically biodegradable. In some variations the devices comprise a polymer at least partially coated with a drug or a drug eluting layer, and are formed into a shape having a series of peaks and valleys. The device may be advanced adjacent to the sinus cavity in a compressed configuration and then delivered or deployed to allow expansion at least partially within the sinus cavity in any suitable manner. The device is typically crimped prior to its advancement to enable low profile delivery, and the ratio of the device prior to crimping and after crimping may be in the range of about 1:1.1-1:20 (i.e., for 1:1.1, the diameter of the device prior to crimping is 1.1 times the diameter of the device after crimping). The devices useful for these methods may be any of those devices described just above, or other similar such devices having any of the attributes described just above. In variations where the device defines a lumen in its expanding configuration, the method may also comprise irrigating one or more sinus cavities.

Methods of making self-expanding devices are also described. In general, the methods comprise extruding a polymer filament, where the polymer filament comprises PLG having a molar percent of glycolide from about 70-100% or a molar percent of lactide from about 70-100%, coating the polymer filament with a drug eluting layer, and forming the device. The device is typically crimpable from an expanded configuration to a delivery configuration by at least 10%. The method may further comprise crimping the device, or any additional suitable step.

Also described here are delivery devices and methods for using them. The delivery devices may deliver any suitable device or implant, including the self-expanding devices described here. In some variations, the delivery device comprises a handle and a cannula. In some variations, the cannula may have one or more curved section. Each curved section may have any suitable angle. In some variations, the angle may be between about 10° and about 120°. In other variations, the angle may be between about 50° and about 120°. In still other variations, the angle may be between 10° and about 110°. In some variations the cannula may be steerable. Additionally the cannula may have any suitable number of lumens (e.g. 1, 2, 3, 4, or 5 or more lumens).

Additionally, in some variations the cannula comprises a cannula tip that has one or more markers. The markers may or may not aid in direct visualization of the cannula tip, and may or may not aid in indirect visualization of the cannula tip. Furthermore, the cannula tip may have any suitable configuration of elements. In some variations, the cannula tip may comprise slots and prongs. In some of these variations, the prongs may be directed inwardly. In some of these variations, the prongs may approximate a point. In other variations, the cannula tip may comprise a plate extension, an expandable funnel-shaped tip, a bulbous tip, a slotted tube, a wedge-shaped tip, a shapeable or deformable tip, combinations thereof and the like.

In some variations the delivery devices may comprise one or more sheaths. In some variations, the sheath is disposed around the outside of the cannula. In other variations, the sheath is disposed inside of the cannula. In some variations, the sheath is releasably attached to the cannula. The sheath may or may not be configured to release one or more drugs. Furthermore, in some variations, the delivery device may comprise one or more dilators or other implants disposed around the outside of the cannula.

Additionally, in some variations the delivery devices described here may comprise a deployment mechanism for deploying one or more implants from the cannula. In some variations, the deployment mechanism comprises a plunger. In some of these variations, the plunger may comprise one or more runners. In other variations, the deployment mechanism may comprise one or more stoppers.

Furthermore, the handle may have any suitable configuration of elements. In some variations, the handle may comprise a plunger or trigger that may be attached to a deployment mechanism. In other variations, the plunger or trigger may be attached to the cannula. In some variations, the handle may be adjustable. In some of these variations, the handle comprises one or more adjustable rings. In other variations, the handle comprises a plunger or trigger having an adjustable length.

Additionally described here are methods for delivering one or more implants using the delivery devices described here. In some variations, the methods comprise crimping a self-expanding device from an expanded configuration to a compressed configuration, wherein the self-expanding device comprises at least two polymer filaments and has a shape that approximates a repeating diamond-shaped pattern, the diamond-shaped pattern defined by a series of repeating peaks and valleys, loading the device in its compressed configuration into a delivery device comprising a cannula, wherein the cannula comprises one or more curved sections, advancing the cannula to a paranasal sinus cavity or ositum, and deploying the self-expanding device to the paranasal sinus cavity or ostium such that the self-expanding device expands to its expanded configuration. The delivery device may have any feature or combination of features as described above.

In some variations, the method comprises puncturing one or more tissues using the delivery device. In some of these variations, the one or more tissues are punctured using a slotted sheath. In other variations, the method comprises visualizing the delivery device. In some of these variations, the delivery device is visualized directly. In others of these variations, the delivery device is visualized indirectly (e.g. fluoroscopy or ultrasound). In still other variations, the methods comprise flushing or spraying the paranasal sinus cavity or ostium. In yet other variations, the methods comprise dilating one or more tissues.

Additionally, the self-expanding device may be released from the delivery device in any suitable way. In some variations, the self-expanding device may be released from the device by advancing a pusher through the cannula. In other variations, the self-expanding device may be delivered by withdrawing the cannula relative to a stopper or a sheath. In other variations, the self-expanding device may be released by rotating the cannula relative to a stopper or a sheath.

BRIEF DESCRIPTION OF THE DRAWINGS

FIG. 6 is a simplified depiction of the anatomy of the sinuses following a typical sinus surgery.

FIGS. 7A-7C depict an illustrative method of delivering a device to an ethmoid sinus cavity.

FIGS. 21A and 21C are side views of these variations in their unexpanded configurations. FIGS. 21B and 21D are side views of these variations in their expanded configurations.

FIGS. 23A and 23B show an illustrative depiction of a steerable cannula that may be used with the delivery devices described here.

FIGS. 24A-24P depict various cannula tips that may be useful with the delivery devices described here.

FIGS. 30B and 30C are side views of the stopper and cannula, respectively. FIGS. 30D-30F illustrate one manner of operating the delivery device shown in FIG. 30A.

FIGS. 35A and 35B depict side views of another variation of a suitable device having a shape that approximates overlaid crowns.

DETAILED DESCRIPTION

Described here are self-expanding devices for use within a hollow-body organ, a sinus cavity, the vasculature, or the like. Methods for treating various conditions or diseases, as well as methods for manufacturing the devices are also described. The devices may have utility in any area of the body that may benefit from the support or function the devices may provide. In some variations, the devices are used in one or more sinus cavities (either before or after a functional endoscopic sinus surgery). In other variations, the devices are used in the vasculature, to help improve vessel patentcy or to provide support or functional benefit (for example in areas of plaque or potential plaque formation, etc.). In still other variations, the devices may be used in the bladder, ureter, urethra, or the like. Additionally described here are delivery devices and methods for using the delivery devices. The delivery devices may be used to deliver one or more of the self-expanding devices described here, or may be used to deliver one or more different implants.

I. Devices

Self-Expanding Devices

In general, the devices described here are self-expanding devices, having a first compressed configuration, and a second expanded configuration. The devices may or may not be configured to conform to or against one or more tissue surfaces in their expanded configuration, and such conformation may be facilitated in certain instances by the device having a geometry or configuration that has the ability to conform to an irregular tissue surface or irregular body cavity. Indeed, the devices may have any suitable configuration. In some variations, the devices comprise either a single continuous filament or at least two non-intersecting filaments. By non-intersecting, it is generally meant that the filaments do not cross each other in a typical woven fashion. In other variations, the devices comprise two or more separate components, which may be filaments or separate devices, and the separate components may or may not be joined or intersect. The devices may be made out of any suitable material or materials, and may or may not be configured for drug delivery. Typically, at least a portion of the devices comprises a biodegradable polymer, and the devices are configured to degrade over a predetermined period of time. This is not to say that the devices may not be removed if necessary, and in some configurations, the devices are configured for easy retrieval and/or removal.

Figure 1A:
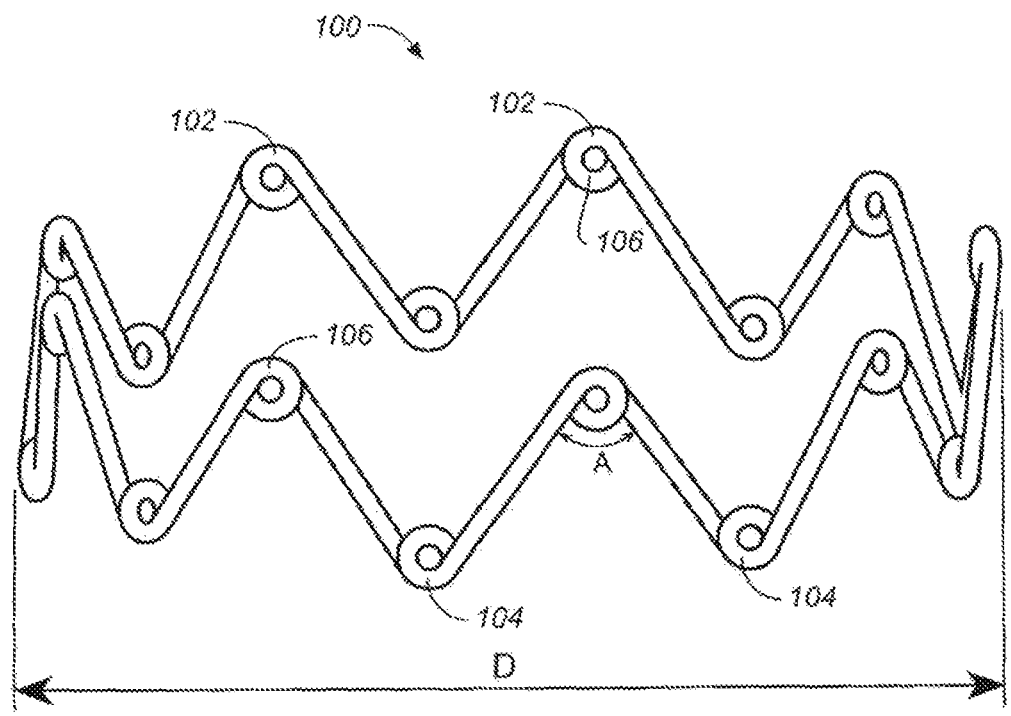
FIG. 1A is an illustrative depiction of one variation of the devices described here shown in an expanded configuration.
Figure 1B:
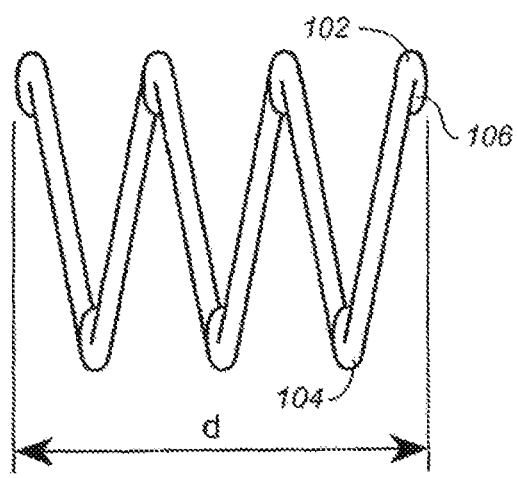
FIG. 1B is a side view of the device of FIG. 1A shown in its compressed, delivery configuration.

With specific reference to the figures now, FIGS. 1A and 1B illustrate a variation of device (100) in its expanded and compressed configurations, respectively. In this variation, the device comprises a single continuous filament and is formed into a shape having a series of peaks (102) and valleys (104). While a great many peaks and valleys are shown in the example of FIGS. 1A and 1B, it should be understood that the device may comprise any number of peaks or valleys. Additionally, it should also be understood that while the exemplary device shown in FIGS. 1A and 1B have peaks and valleys, the device need not have any peaks or valleys. Thus, the devices described here may have from zero to a great many peaks and valleys.

In the variation shown in FIGS. 1A and 1B, the device also has a series of loops (106) formed at the ends of the peaks and valleys. It should be clear that the device need not have such loops, but such loops may be desirable in certain circumstances. Any number of loops may be formed on the device, and the loops, as will be described in more detail below, may have any suitable configuration. The loops may be formed on the ends of all the peaks and valleys, some of the peaks and valleys, or none of the peaks and valleys. Similarly, the loops may be formed on all or some of the peaks, but none of the valleys, or on all or some of the valleys, but none of the peaks, and the like.

In certain instances, a loop may be desirable as it may help provide for an even distribution of the bending stresses that are applied when the device is reduced into its compressed configuration. The ability of the loop to distribute stress may also contribute to the ability of the device to self-expand upon deployment by lessening plastic deformation of the device. One or more loops may also serve as sites for drug delivery, as will be described in greater detail below. In these variations, the loops may be coated, or impregnated with a drug, or coated or impregnated with a polymer for delivery of a drug therefrom. The loops may further be useful in manufacturing of the device, as described below, by for example, serving as an aid for positioning and manipulating the device.

In some variations, the loops comprise or define eyelets for passage of a suture therethrough. The suture may be useful, for example, to help collapse the device into its compressed configuration when pulled, as will be detailed below. In other variations the suture (whether passing through an eyelet or otherwise attached to the device) may be useful in retrieving the device, either temporarily (in the event of initial misplacement, for example) or permanently (in the event the device fails to completely degrade or in the event the device needs to be prematurely withdrawn, e.g., in the event of infection, complication, or the like). The angle (A) defined by the loop apex may be of any suitable degree. For example, the angle may be between about 10° to 170°, between about 10° to 150°, between about 10° to 130°, between about 10° to 110°, between about 10° to 90°, between about 10° to 70°, between about 10° to 30°, between about 30° to 170°, between about 30° to 150°, between about 30° to 130°, between about 30° to 110°, between about 30° to 90°, between about 30° to 70°, between about 30° to 50°, between about 50° to 170°, between about 50° to 150°, between about 50° to 130°, between about 50° to 110°, between about 50° to 90°, between about 50° to 70°, between about 60° to 120°, between about 60° to 90°, between about 70° to 170°, between about 70° to 150°, between about 70° to 110°, between about 70° to 90°, between about 90° to 170°, between about 90° to 150°, between about 90° to 130°, between about 90° to 110°, between about 110° to 170°, about 110° to 150°, about 110° to 130°, about 130° to 170°, about 130° to 150°, about 150° to 170°, and the like. In some variations, the angle is about 75°. It should noted that when the device is crimped to a self-expanded device, or placed in a portion of the anatomy, the angle (A) defined by the loop apex may decrease to an angle smaller than those listed above. Indeed, angle (A) may be reduced to any suitable angle. For example, the angle may be reduced to an angle between about 0° to 30°, about 0° to 25°, about 0° to 20°, about 0° to 15°, about 0° to 10°, about 0° to 5°, about 5° to 15°, about 5° to 10°, about 1° to 5°, about 2° to 4°, and the like.

The devices described here are typically capable of self-expanding when deployed. The rate of expansion may be dependent on a number of environmental factors, for example, temperature, pH, etc., as well as certain physical characteristics of the device itself, for example, the materials used and the device configuration. As such, the device may be designed to expand at a certain rate under certain conditions. In some variations, the device, while still self-expandable, may be aided in its deployment with use of an expandable balloon, expansion device or a heated element. In some variations, a ball or other structure is pulled through the inner diameter of the device in order to aid in the device's expansion. In still other variations, the device may be deformable into its expanded configuration.

Returning back to FIGS. 1A and 1B, device (100) has an expanded diameter (D), shown in FIG. 1A, and a compressed diameter (d), shown in FIG. 1B. The ratio of the expanded diameter (D) to the compressed diameter (d), or D:d, may be representative of how effectively the device may be compressed. This ratio may be any suitable ratio. For example, the ratio may be from about 2:1 to about 20:1, from about 2:1 to about 15:1, from about 2:1 to about 12:1, from about 2:1 to about 8:1, from about 2:1 to about 5:1, from about 5:1 to about 20:1, from about 5:1 to about 15:1, from about 5:1 to about 12:1, from about 5:1 to about 8:1, from about 5:1 to about 8:1, from about 8:1 to about 20:1, from about 8:1 to about 15:1, from about 8:1 to about 12:1, from about 12:1 to about 20:1, from about 12:1 to about 15:1, from about 15:1 to about 20:1, about 10:1, and the like. The actual values of the expanded and compressed diameters will typically depend on the target site for deployment, so that appropriate tissue apposition may be effected. However, in general, the compressed configuration has a diameter suitable for low profile delivery using a delivery device. For example, the diameter (d) of the device in the compressed configuration may be from about 0.05 mm to about 5.5 mm, from about 0.05 mm to about 3 mm, from about 0.05 mm to about 1 mm, from about 1 mm to about 5.5 mm, from about 1 mm to about 3 mm, from about 3 mm to about 5.5 mm, and the like. In some variations, the diameter (d) of the device in its compressed configuration is about 4.5 mm. It should also be understood that while the device may provide support for a given area, the device need only be in physical contact with a fraction of that area, for example, about 5% of that area.

It should be understood that while shown as having a generally crown shape in FIGS. 1A and 1B, the device may be any shape capable of assuming an expanded configuration for apposition against tissue, as well as a compressed configuration for low profile delivery. For example, the device may have a generally double crown type shape, may have a generally smooth, undulating type shape, may have a generally helical type shape, or the like.

Figure 15:
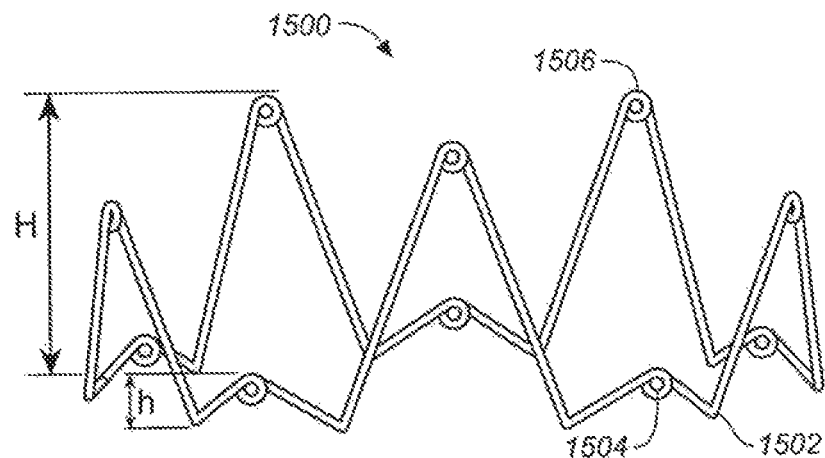
FIGS. 15-16 are illustrative depictions of suitable variations of devices described here, shown in their expanded configurations.

FIG. 15 illustrates one variation of a suitable device (1500) in its expanded configuration. This variation may find particular utility in instances where it is desirable to provide differing amounts of support to different areas of surrounding tissue. In this variation, the device comprises a single continuous filament formed into a shape having a series of valleys (1502), a series of lower peaks (1504), and a series of upper peaks (1506), which combine to form a device having a generally varying crown shape. While many upper peaks, lower peaks, and valleys are shown in FIG. 15, the device may include any number of peaks or valleys. When device (1500) is in its expanded configuration, each upper peak (1506) will have an upper peak height (H) relative to the valleys (1502), and each lower peak (1504) will have a lower peak height (h) relative to the valleys (1502). The upper (H) and lower (h) peak heights may be any suitable values, and these values may be selected or determined based on the intended manner in which the device will be used.

While the peaks of device (1500) shown in FIG. 15 alternate between upper peaks (1506) and lower peaks (1504), they may take on any suitable arrangement or pattern. In some variations, this arrangement may follow a repeating pattern, but need not. Furthermore, in some variations the number of upper peaks (1506) may be equal to the number of lower peaks (1504). Of course, in other variations, the number of upper peaks (1506) is not equal to the number of lower peaks (1504). Indeed, all but one of the peaks may be an upper peak (1506), all but one of the peaks may be a lower peak (1504), or the peaks may comprise some mixture of upper (1506) and lower (1502) peaks. Additionally, the device (1500) may have a series of loops (1508) formed at the ends of the upper peaks, lower peaks, and valleys, but need not. The loops, which were described briefly above and will be described in more detail below, may be formed on all, some, or none of the upper peaks, on all, some, or none of the lower peaks, or on all, some, or none of the valleys, or some combination thereof.

While shown in FIG. 15 as having two distinct series of peaks (upper (1506) and lower (1504)), the device (1500) may alternatively have three or more distinct series of peaks. Each series of peaks may have any number of that type of peak, and the peaks of each series may have any height relative to the valleys. Furthermore, the series of peaks may have any suitable arrangement or pattern as described above.

Figure 16:
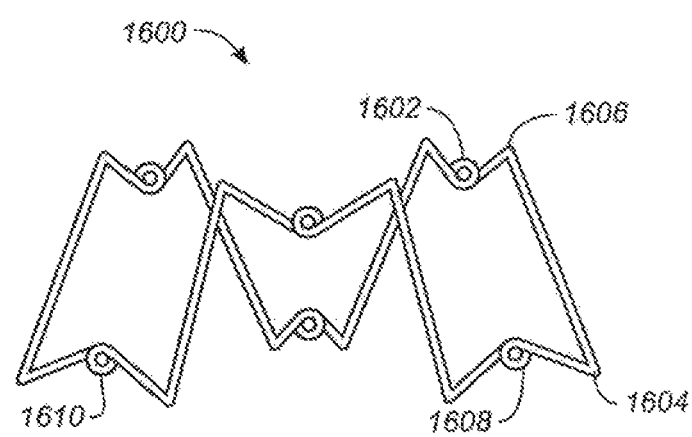

FIG. 16 shows another variation of a suitable device (1600) in its expanded configuration. In this variation, the device (1600) comprises a single continuous filament and is formed into a shape having series of upper valleys (1602), lower valleys (1604), upper peaks (1606) and lower peaks (1608). As with all devices described above and throughout, the device of this variation may have any number of peaks or valleys, and the peaks (upper or lower) may have any suitable height relative to the valleys (upper or lower). The peaks and valleys may take on any arrangement or pattern as described above in relation to the illustrative example of FIG. 15. For example, in the variation shown in FIG. 16, the upper peaks (1606) alternate with the lower peaks (1608), and the upper valleys (1602) alternate with the lower valleys (1604) to create a device having a generally quasi-crown shape. Additionally, the device (1600) may have a series of loops (1610) formed at the ends of the upper peaks, lower peaks, upper valleys, lower valleys, or some combination thereof. Of course, the device need not have any loops. Additionally, it should be understood that the loops (described hereinthroughout) may be formed on all, some, or none of the upper peaks, on all, some, or none of the lower peaks, on all, some, or none of the lower valleys, or on all, some, or none of the upper valleys, or some combination thereof.

Figure 17A:
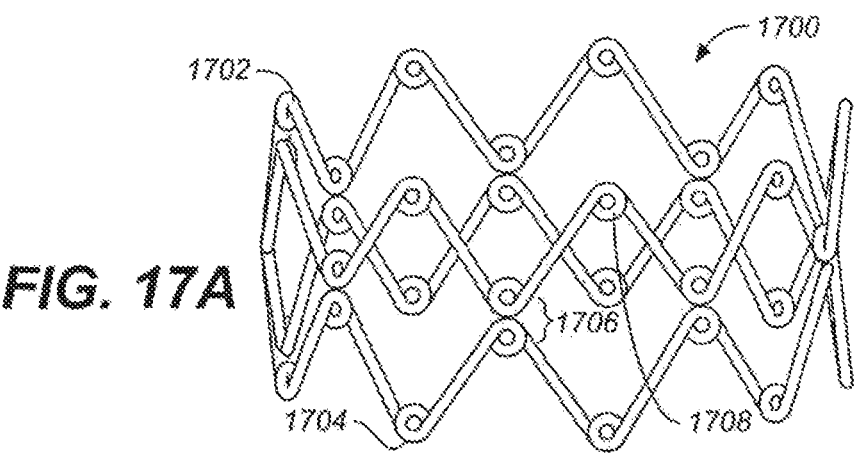
FIG. 17A is a perspective view of a suitable device, where the device has a pattern that approximates a repeating diamond pattern.

The type of device chosen (i.e., length, geometry, number of loops, etc.) may be selected based on the particular use of the device. In some instances it may be desirable to select a device having a longer length than the devices described just above, yet having sufficient radial strength to overcome forces applied to it during use. FIG. 17A illustrates one variation of device (1700) having a length longer than those described above, here shown in its expanded configuration. In this variation, the device comprises one or more filaments and is formed into a shape having a series of peaks (1702), valleys (1704), and junctions (1706). While many peaks, valleys, and junctions are shown in FIG. 17A, the device (1700) may include any suitable number of each of these elements. Furthermore, although the junctions (1706) in the illustrative device depicted in FIG. 17A are located between peaks (1702) and valleys (1704) to create a substantially diamond-shaped pattern, it should be appreciated that the device may take on any pattern. Indeed, in some variations the device may take on a substantially kite-shaped pattern, or the like.

Additionally, the device (1700) may have a series of loops (1708) at the peaks, valleys, junctions, or some combination thereof. It should be noted that the device need not have such loops, but loops may be desirable in certain circumstances as described hereinthroughout. Furthermore, any number of loops may be formed on the device, and each loop may have any suitable configuration as described below. For example, the loops may be formed on all, some, or none of the peaks, valleys, junctions, or combination thereof.

Figure 17B:
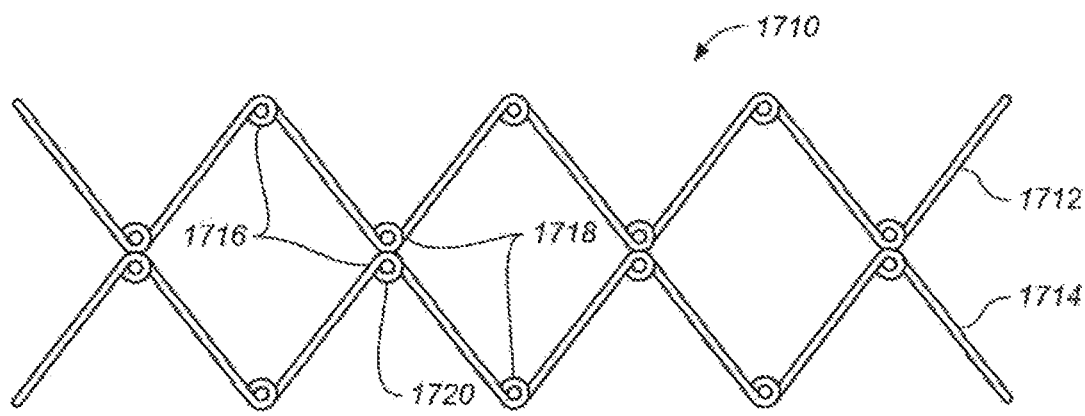
FIGS. 17B and 17C show side views of other variations of suitable devices having patterns similar to the device of FIG. 17A.

The overall structure of the device depicted in FIG. 17A may be achieved in any number of different ways. In some variations (not shown), separate filaments are joined together to form substantially diamond shapes. In others variations, as shown in FIG. 17B, the structure of device (1710) may be achieved by positioning a top crown-shaped device 1712), such as the exemplary device shown in FIG. 1A, above a bottom crown-shaped device (1714). In this way, a modular or composite device is formed. Of course the device may comprise any number of modular or separate units, to create a device having any suitable length or geometry.

In these variations, each of the top (1712) and bottom (1714) crown-shaped devices has a series of peaks (1716) and valleys (1718). As such, the peaks of the top crown-shaped device (1712) form the peaks of device (1710) while the valleys of the bottom crown-shaped portion (1714) form the valleys of device (1710). The valleys of the top crown-shaped device (1712) join with the peaks of the bottom device (1714) to form junctions (1720). In some variations, the top (1712) and bottom (1714) crown-shaped portions may have different axial lengths, and thus may have different radial strengths. While modular or composite devices are described with respect to this variation, it of course should be understood that these types of devices may also be formed from a single continuous filament.

Figure 17C:
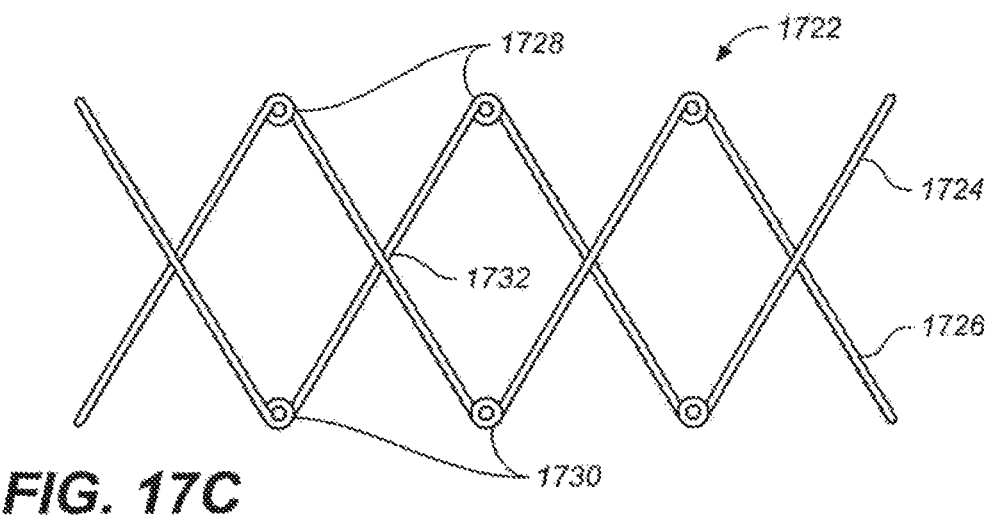

In still other variations, as shown in FIG. 17C, device (1722) may be formed by positioning first crown-shaped device (1724), such as the exemplary device shown in FIG. 1A, in a phase-shifted position relative to second crown-shaped device (1726). Both first (1724) and second (1726) crown-shaped devices have series of peaks (1728) and valleys (1730), which constitute the peaks and valleys of the device (1722). Additionally, junctions (1732) are formed by the intersection of the filaments of the two crown-shaped devices. The device (1722) may be formed from a single continuous filament, or may be formed from a combination of two separate devices. Of course, when the device is modular in nature, each individual device may be formed from a single continuous filament or from more than one filament.

Figure 18:
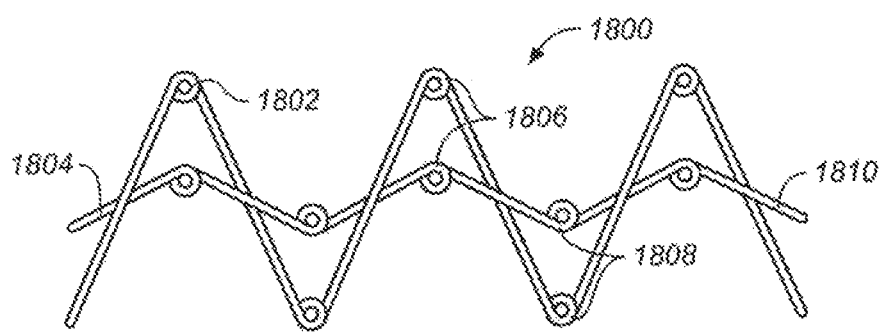
FIG. 18 depicts a side view of one variation of a suitable device having a shape that approximates overlapping crowns.

While the crown-shaped devices shown in FIG. 17C are positioned such that the peaks of one crown-shaped device are positioned above the valleys of the other crown-shaped device, the crown-shaped devices may have any relative positioning. Depending on the relative rotation (or phase shift) between the first (1724) and second (1726) crown-shaped devices, the device (1724) may cease to have the overall structure shown generally in FIGS. 17A-17C, instead taking on a rectangular-shaped, or other shaped pattern (not shown). If the phase shift between the two devices is of a large enough magnitude, as illustrated in FIG. 18, device (1800) is formed such that the peaks (1806) of the first (1802) and second (1804) crown-shaped devices are positioned substantially in alignment. In this variation, the valleys (1808) of the first (1802) and second (1804) crown-shaped devices are also positioned substantially in alignment. Although junctions (1810) may be positioned approximately equidistant between the peaks and valleys, of the first crown-shaped device (1802), as shown in FIG. 18, the first (1802) and second (1804) crown-shaped devices may alternatively be shifted axially relative to each other. For example, in some variations (not shown), the first and second crown-shaped devices are axially oriented such that the peaks of each crown-shaped device join to form junctions. In other variations, the valleys of each crown-shaped device may join to form junctions.

FIGS. 35A and 35B illustrate another modular variation of device (3500) comprising first (3502) and second (3504) crown-shaped devices. FIG. 35B shows first (3502) and second (3504) crown-shaped devices separated, while FIG. 35A shows first (3502) and second (3504) crown-shape devices connected at junctions (3506) to form device (3500). As shown in FIG. 35B, junctions (3506) may be formed by connecting filaments (3508) from each crown-shaped device such that the filaments (3508) do not overlap. These junctions (3506) may be formed in any suitable manner (e.g., bonding, welding, mechanical fastening). When the device (3500) is crimped, filaments (3508) in junction (3506) may rotate in the same direction, as opposed to rotating in different directions, which may in turn help prevent the filaments (3508) from disengaging. This may, in turn, increase the overall strength of device (3500). It should be noted, however, that each junction of device (3500) may be any suitable junction as described in more detail below.

Figure 19:
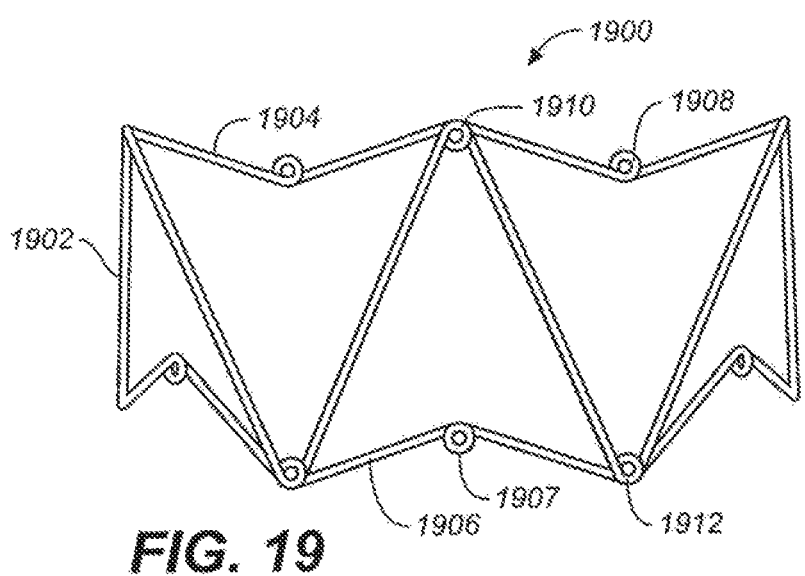
FIG. 19 is a side view of a suitable device, where the device has a pattern that approximates a repeating arrowhead pattern.

In still other variations, as shown in FIG. 19, device (1900) comprises first (1902), second (1904) and third (1904) crown-shaped devices, with each crown-shaped device having a series of peaks (1907) and valleys (1908). Device (1900) may be made from a single continuous filament, or may be made from individual crown-shaped devices in a composite fashion (e.g., where each crown-shaped device is made from a separate continuous filament). In some variations, the first (1902) and second (1904) crown-shaped devices are oriented such that the peaks of each device join to form upper junctions (1910). In some of these variations, the first (1902) and third (1906) crown-shaped devices are axially oriented such that the valleys of each device join to form lower junctions (1912). In these variations, the overall structure of device (1900) takes on a generally repeating arrowhead-shaped pattern. It should be appreciated that the overall structure of these devices may be changed either by phase-shifting one or more of the crown-shaped devices in relation to the entire device, by axially shifting one or more of the crown-shaped devices in relation to the entire device, some combination of the foregoing, and the like.

Figure 20:
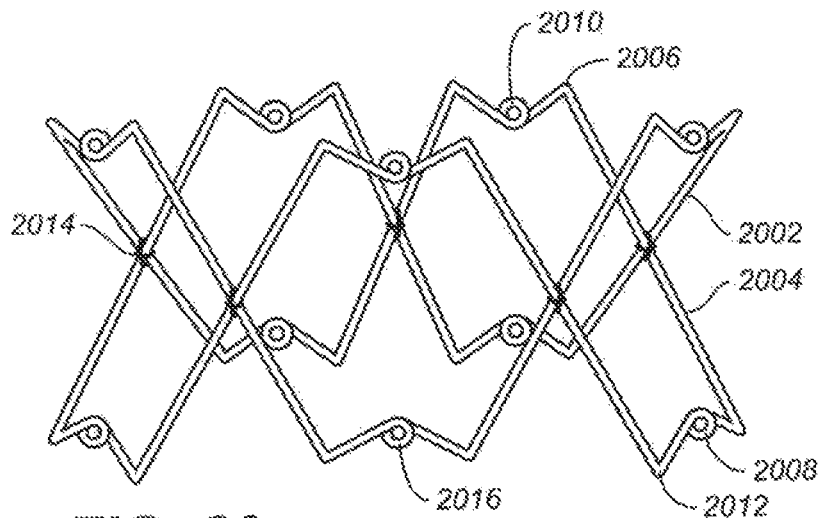
FIG. 20 is an illustrative depiction of a suitable device variation shown in its expanded configuration.

FIG. 20 shows yet another variation of device (2000) in its expanded configuration. Shown there are first (2002) and second (2004) quasi-crown-shaped devices, such as the device illustrated in FIG. 16. In these variations, the first (2002) and second (2004) quasi-crown-shaped devices have upper (2006) and lower (2008) peaks, upper (2010) and lower (2012) valleys, and junctions (2014). In some variations, one of the quasi-crown-shaped devices may be phase-shifted relative to the other, axially shifted relative to the other, combinations thereof, and the like. In other variations (not shown), one or more of the quasi-crown-shaped devices may be replaced by one or more varying-crown-shaped devices. In still other variations, one or more of the quasi-crown-shaped devices may be replaced with a crown-shaped device as described above. Additionally, some variations may contain more than two devices that are quasi-crown-shaped, crown-shaped, varying-crown-shaped, some combination thereof, and the like.

The entire device (2000) may be made of one continuous filament, or may be modular or composite in nature. The device may additionally contain a series of loops (2016), but need not. These loops may take on any suitable configuration as described below. The loops may be formed on of all of the peaks, valleys, and junctions, some of the peaks, valleys and junctions, none of the peaks, valleys, and junctions, or some combination thereof. The junctions may take on any suitable configuration as described below.

Figure 2A:
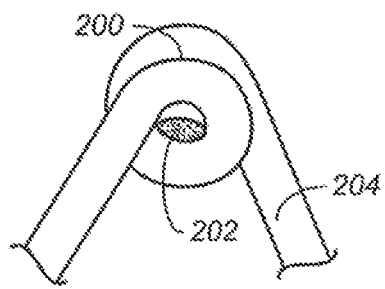
FIGS. 2A-2E depict various loop configurations that may be useful with the devices described herein.
Figure 2B:
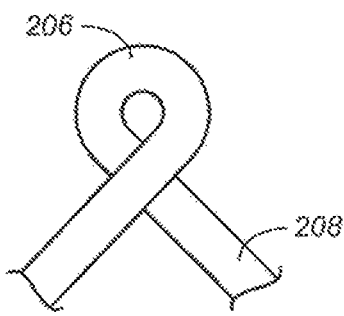
Figure 2C:
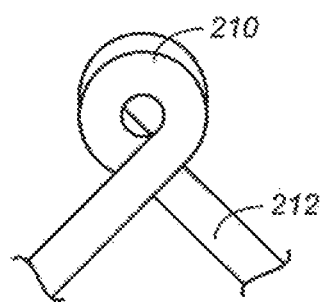
Figure 2D:
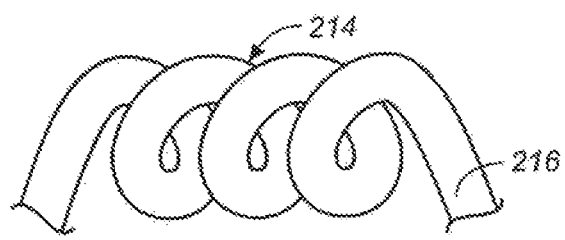
Figure 2E:
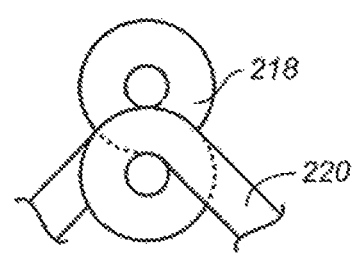

When loops are used with the devices described herein, they may have any suitable configuration. FIGS. 2A-2E provide a number of illustrative examples of suitable loop configurations for use with any of the described devices. Shown in FIG. 2A is a variation of loop (200) including drug depot (202). In this variation, device filament (204) has been curled more than about 360°, but less than about 720° to create a full loop. FIG. 2B illustrates a variation of loop (206), in which the device filament (208) has been curled less than about 360°. Shown in FIG. 2C is a variation of loop (210) in which the device filament (212) has been curled more than about 720° to create two loops. FIG. 2D depicts a loop (214) in which the device filament (216) has been curled in several full rotations in order to create a spring-like configuration. FIG. 2E depicts a loop (218) in which the device filament (220) has been rotated less than 360° in one direction to form a first loop, then rotated approximately 360° in the opposite direction to form a second loop, the two loops thus approximating the shape of a figure eight. Of course, these are just a few of the many types of loop configurations that may be used.

Although a drug depot (202) is shown only FIG. 2A, drug depots or drug delivery sites may be used in conjunction with any loop configuration when drug delivery is desirable. As described above, some, all or none of the loops of a device may contain a drug depot or drug delivery site. Additionally, drug depots may be contained on or in any portion of the devices. In some variations, the drug depot is in the form a polymer coating, and made similar to the polymeric drug eluting layers described hereinthroughout. In other variations, the drug depot (202) may come in the form of a drop or bead of drug-filled material placed within, on, or around an outer area of the loop. When the device comprises a filament that has perforations, such as slots, holes or channels, the drug depot may also (or alternatively) be contained therein. When more than one drug depot is used, the drugs for delivery therefrom may be the same or different. Similarly, drug released from a drug depot may be the same or different from a drug released from other portions of the device. The drug depot may release drug at the same rate as the rest of the device, or may release drug at a different rate.

Figure 22A:
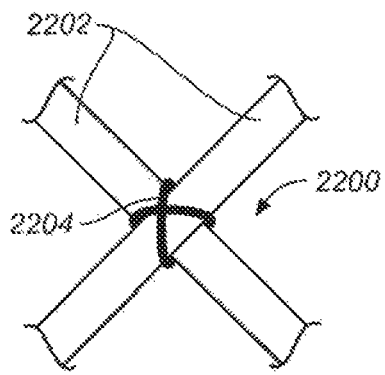
FIGS. 22A-22M depict various junction configurations that may be useful with the devices described here.
Figure 22B:
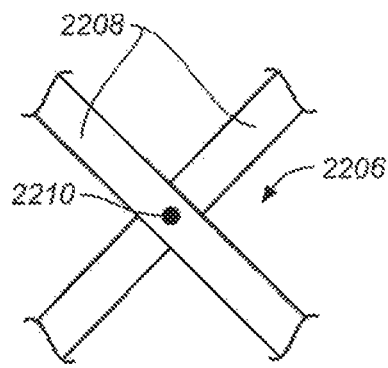

While some junctions comprise one or more loops as will be described below, it is noted that junctions are generally differentiated from loops in that junctions occur at the intersection or meeting of two or more filaments or filament sections. When junctions are used with the devices described here, they may have any suitable configuration. The configuration of a given junction may be the same as or different from other junctions within the same device. FIGS. 22A-22M provide illustrative examples of suitable junction configurations. Shown in FIG. 22A is one variation of junction (2200), including two straight filaments (2202) and suture ties (2204). While shown in FIG. 22A as including suture ties (2204), junction (2200) need not. Indeed, in some junctions the two filaments are not bound, joined, or attached in any way. In other variations, one or more elastic bands, washer rings, gaskets, clamps, sutures, clips, other mechanical fasteners, or a combination thereof may be used to join the two filaments. In still other variations, the two filaments may be joined using welding (e.g., heat welding, ultrasonic welding, tacking, staking, and the like), may be bonded using glue, adhesives, or low melting temperature polymers, or the like. In variations that utilize a polymer, the polymer may be biodegradable. Additionally the polymer may be configured to release one or more drugs over a period of time. In still other variations, as illustrated in FIG. 22B, junction (2206) includes bolt or other biocompatible, (and in some variations biodegradable) cylinder (2210) that is placed through holes or channels (not shown) formed in the filaments. (2208). In this way, the bolt (2210) may help allow for rotation between the filaments (2208), but not transverse movement therebetween. While shown in FIG. 22B as having a bolt (2210), the junction (2206) may include any suitable rod, screw, pin, peg, or cylinder (in most cases made from a biocompatible and biodegradable material). It should also be appreciated that any appropriate combination of processes and structures for joining or bonding two or more filaments, as described above, may be used in these junctions.

Figure 22C:
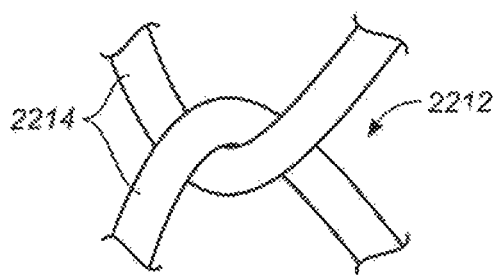
Figure 22D:
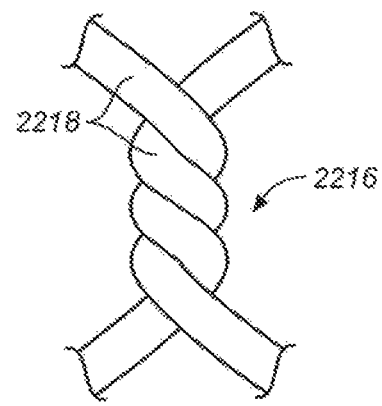
Figure 22F:
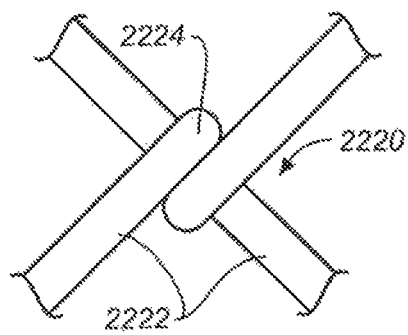
Figure 22E:
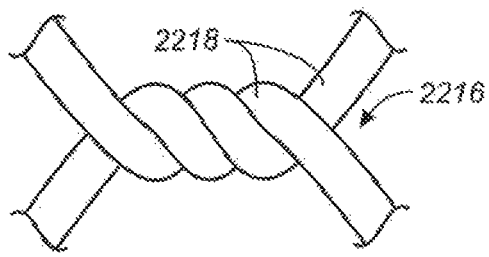
Figure 22G:
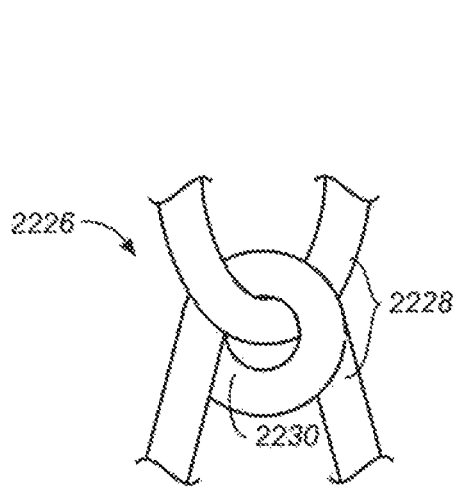

FIG. 22C shows another variation of junction (2212) in which filaments (2214) are bent around each other. The filaments (2214) may additionally be bound using any combination of processes and structures described above. While shown in FIG. 22C as being bent at approximately 90° angles, the filaments (2214) may be bent at any suitable angles. In other variations, as shown in FIG. 22D, junction (2216) may be formed by winding filaments (2218) around each other to form a generally helical structure. The helices of these variations may include any number of turns or loops. Also, while the wound filaments (2218) are configured vertically, they may alternatively be configured horizontally, as shown in FIG. 22E, or at an angle (not shown).

In some variations, one or more of the filaments form a loop at the junction. In these variations, the loops may have any configuration as described above. In variations in which more than one fiber form loops, these loops may have the same or different configurations. FIG. 22F shows one variation of junction (2220) including filaments (2222) and loop (2224). In this variation, one filament passes straight through the loop created by the other filament. In other variations, such as junction (2226) shown in FIG. 22G, a filament (2228) is passed through the loop (2230) at an angle or in a bent manner. These junctions can be formed by either winding a first filament around a second filament, or by threading a first filament through a pre-formed loop.

Figure 22H:
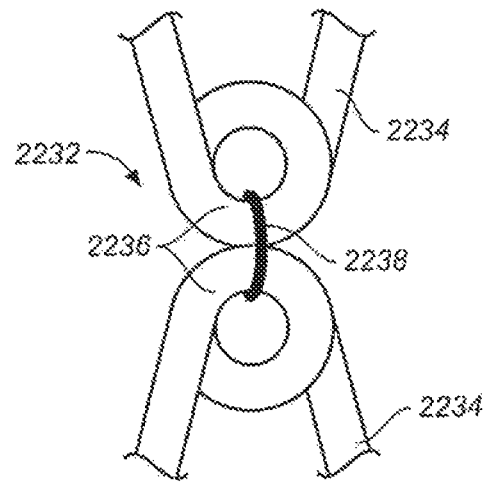
Figure 22I:
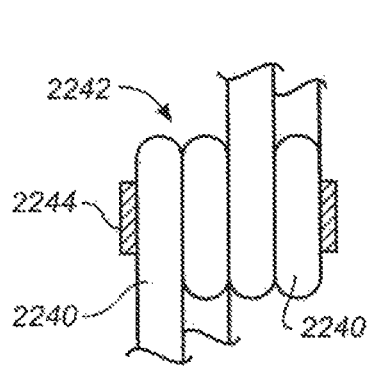
Figure 22J:
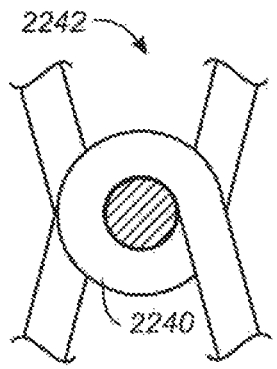

In other variations, the junction comprises at least two loops formed from at least two fibers. FIG. 22H shows one such variation of junction (2232), including filaments (2234), loops (2236), and suture tie (2238). In the illustrative example shown in FIG. 22H, the two loops (2236) are bound to each other using a suture tie (2238). However, it should be appreciated that any combination of structures or processes as described above may be used to join the loops. Additionally, in some variations, one loop has a certain orientation relative to another. For example, FIGS. 22I and 22J show a side and front view respectively of one variation of junction (2242). Shown there are loops (2240) which are joined using barbell-shaped structure (2244) such that the loop apertures (not shown) are in alignment. The barbell-shaped structure (2244) generally allows the loops (2240) to rotate with respect to each other, but not to move laterally with respect to each other. In some variations (not shown), the barbell-shaped structure has a channel into which a drug depot may be placed, or through which a suture may be passed. While shown in FIGS. 22I and 22J as having a barbell-shaped structure (2244), and suitable structure may be used. For example, a screw may be threaded through the apertures defined by the loops.

Figure 22K:
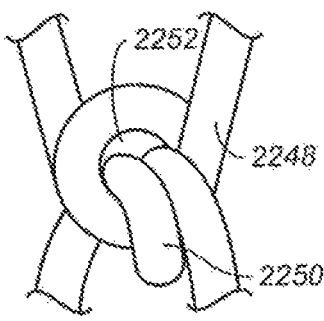

FIG. 22K shows another variation of junction (2246) including filaments (2248) and loops (2250). For each loop, the filament creating that loop is wound through the aperture (2252) defined by the other loop. In some variations, this allows for relative rotation between the loops. This junction (2246) may be formed by winding a filament around a pre-formed loop, or by simultaneously winding two filaments. It should also be appreciated that the loops may be further bound or joined using any of the processes or structures as described above.

Figure 22M:
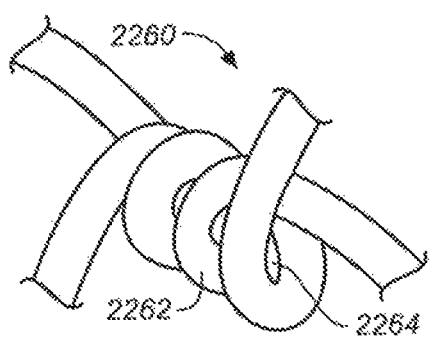
Figure 22L:
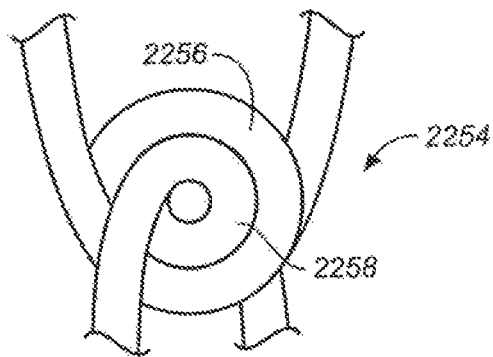

In other variations, such as that shown in FIG. 22L, junction (2254) comprises outer loop (2256) which is wound around the exterior of inner loop (2258). The apertures defined by the two loops may be concentric. In some of these variations, a drug depot may be placed within the aperture defined by the inner loop (2258) or a suture may be threaded therethrough. In some of these variations, the inner loop (2258) may be able to rotate relative to the outer loop (2256). FIG. 22M shows still another variation of junction (2260), comprising loops (2262) that are helically wound. The aperture (2264) defined by the helically wound loops (2262) may hold one or more drug depots therein, or may have a suture passed therethrough. It should also be appreciated that the junctions of these variations may be further bound using any combination of the structures and process described above. Of course, the variations described here are just a few of the many types of junction configurations that may be used with the devices described herein.

Figure 21A:
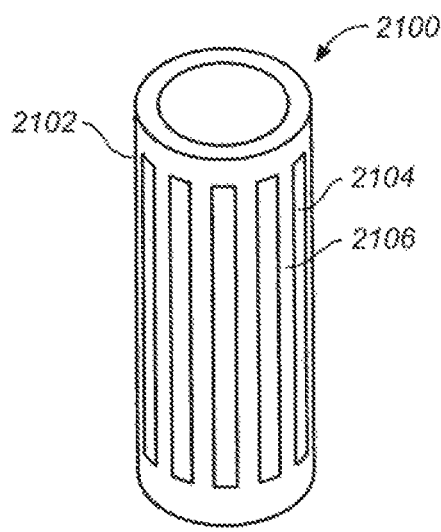
FIGS. 21A-21C show an illustrative depiction of a variation in which the devices comprise slotted tubes.
Figure 21B:
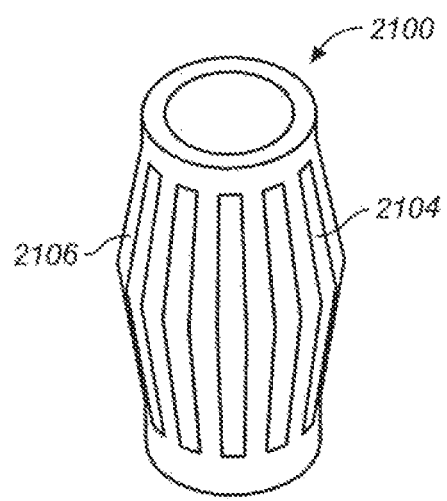
Figure 21C:
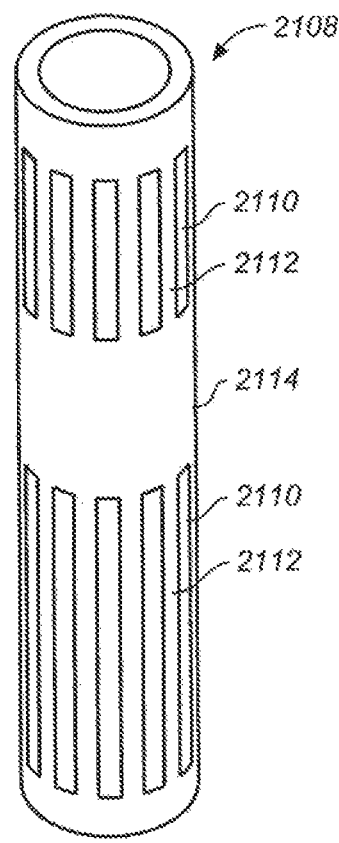
Figure 21D:
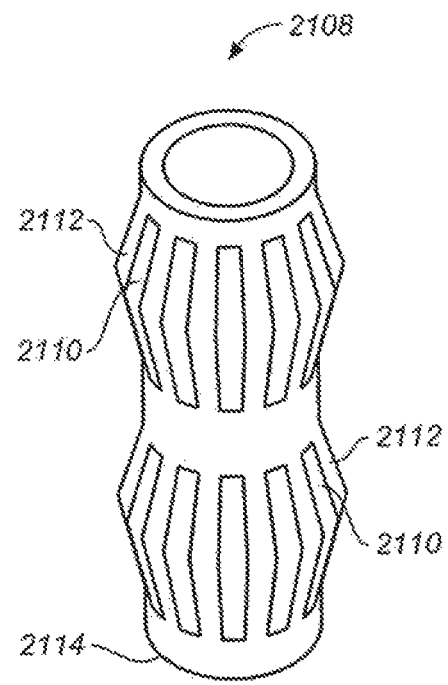

In many variations of the devices described here, the devices are formed from one or more individual filaments, however the devices need not be formed in such fashion. For example, FIGS. 21A and 21B show a variation of a suitable device (2100) in its unexpanded and expanded configurations, respectively. In this variation, the device (2100) comprises a slotted tube (2102). The tube may in turn comprise a series of alternating slots (2104) and struts (2106). While a great many slots (2104) and struts (2106) are shown in FIGS. 21A and 21B, any suitable number of slots and struts may be included. When device (2100) is in its unexpanded configuration, the struts (2106) lay substantially in line with tube (2102). When device (2100) is in its expanded configuration, the struts (2106) bend, flex, or deform away from the body of tube (2102). This expansion decreases the length of tube (2102) while increasing the radius of portions of tube (2102). While shown in FIGS. 21A and 21B as having one set of alternating slots (2104) and struts (2106), the device may have any number of sets of slots and struts. For example, as shown in FIGS. 21C and 21D in its unexpanded and expanded configurations respectively, device (2108) has two sets of alternating slots (2110) and struts (2112) located within tube (2114). While shown in FIGS. 21A-21D as being approximately rectangular in shape, the slots and tubes may take on any suitable shapes or configurations. Of course, the struts (2112) themselves may be made from one or more filaments as described herein.

Figure 3A:
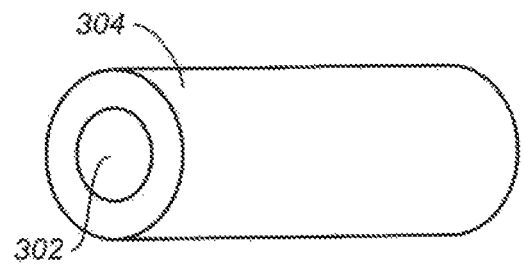
FIG. 3A is a side view of an illustrative filament that may be useful with the devices and methods described here.
Figure 3B:
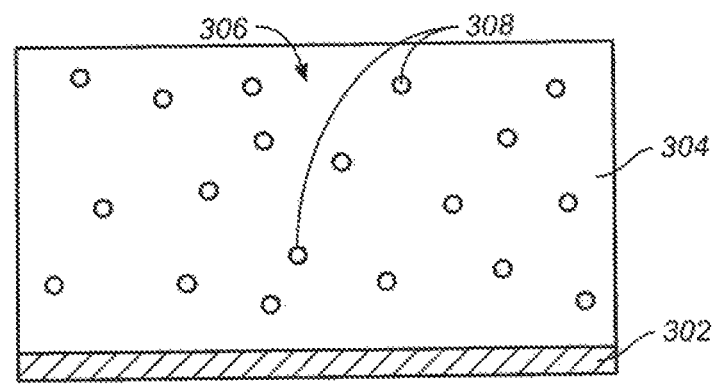
FIG. 3B is a cross-sectional view of the filament of FIG. 3A.

FIGS. 3A and 3B provide illustrative depictions of a suitable filament for use with any of the devices described here. FIG. 3A depicts a side view of a filament, and FIG. 3B depicts a cross-sectional view of the filament of FIG. 3A. Shown in these figures is filament (302) and drug eluting layer (304). Filament (302) may be made from any suitable biocompatible material. Typically, this filament (302) comprises a biodegradable polymer that is capable of degrading over a predetermined period of time. The polymer may be semi-crystalline, crystalline, or amorphous in nature. Suitable polymers for use with the devices will be described in detail below.

Although depicted in FIGS. 3A and 3B as being completely solid, the filament (302) may include features that promote flow of mucous or other bodily fluids around them (e.g., one or more porous beads, or the like). The filament (302) may also include features that increase the surface area upon which drug eluting layer (304) may be deposited. In some variations, the filament (302) may be formed as a perforated structure, including holes, slots, channels or the like. It should be understood that while the filament depicted in FIGS. 3A and 3B include a drug eluting layer (304), the devices described here need not have such a layer. It should also be understood that while the drug eluting layer (304) is shown as generally continuous in nature, in need not be. Indeed, the layer may be discontinuous, covering only a portion, or selected portions of the polymer filament. Similarly, while the filament is shown in FIG. 3A as having a generally cylindrical cross-section, the cross-section may be of any suitable geometry. Also, while the drug eluting layer (304) is shown as having a greater thickness than the filament (302) it surrounds, it should be understood that the respective thicknesses of these components may be selected based upon the final use of the device. These figures are merely illustrative and any number of additional configurations may be used as desirable.

While shown in FIG. 3B as comprising a polymer (306) containing drug particles (308) therein, drug eluting layer (304) may be made of any suitable biocompatible material that is capable of releasing a drug over a period of time, and may be configured in any suitable way. This drug delivery period may vary as desirable, and the drug eluting layer (304) may, accordingly be configured to release drug over a predetermined period of time. In some variations, this period of time is configured to be as long as is required for the filament (302) to biodegrade. In other variations, this period of time may be on the order of hours, on the order of days, on the order of weeks, or on the order of months. The period of drug delivery will likely be determined with consideration of the use of the device. For example, when the device is used for treating one or more conditions of the sinuses, the period may be between about 1 day to about 10 days, between about 1 to about 8 days, between about 1 to about 5 days, between about 1 to about 3 days, between about 5 to about 120 days, between about 5 to about 90 days, between about 5 to about 60 days, between about 5 to about 45 days, between about 5 to about 20 days, between about 20 to about 90 days, between about 20 to about 60 days, between about 20 to about 45 days, between about 45 to about 90 days, between about 45 to about 60 days, or about 30 days. In some variations, as described below, the rate of drug delivery may not be constant over the period of time.

As described above, the drug eluting layer may comprise a polymer (although need not). In some variations, the drug eluting comprises a biodegradable polymer, e.g., poly(DL-lactide-co-glycolide) (i.e., PLG), poly(lactide), poly(glycolide), trymethylated chitosan, or any of the biodegradable polymers described below. In variations using PLG, any suitable molar ratio of lactide to glycolide may be used. For example, the molar percent of lactide or the molar percent of glycolide may be any suitable amount, for example, between about 0% and about 100%, between about 30% and about 100%, between about 50% and about 100%, between about 70% and about 100%, between about 0% and about 70%, between about 30% and about 70%, between about 50% and about 70%, between about 0% and about 50%, between about 30% and about 50%, between about 0% and about 50% and the like. In some variations, the molar ratio of lactide to glycolide is about 70:30.

In a similar manner, the filament (302) may comprise a polymer, for example, a biodegradable polymer e.g., PLG, poly(lactide), poly(glycolide), or any of the biodegradable polymers described below. In variations using PLG, any suitable molar ratio of lactide to glycolide may be used. For example, the molar percent of lactide or the molar percent of glycolide may be between about 70% and 100%. In some variations, the molar ratio of lactide to glycolide is about 10:90. In other variations, the filament does not comprise a polymer, but is still capable of degrading over a period of time. For example, the filament may comprise polytyrosine carbonate, tephaflex, hyaluronic acid, collagen, mixtures thereof, or the like.

The filament may additionally include one or more metallic regions. This may be desirable, for example, to help control the rate of degradation of the device, to provide radio-opacity to the device, to increase the mechanical integrity of the device, or the like. In some variations, the metallic region may include struts with a cylindrical or substantially cylindrical cross-section. Alternatively, the struts may have square, rectangular, oval, or other cross-sectional shapes. In other variations, the metallic region may include metallic particles that are mixed throughout a portion of the filament material. The metallic region may be capable of degrading when exposed to bodily fluids, and may be surrounded by any suitable polymer or other material. The metallic region may also have one or more pores that are configured to include drug particles. Examples of suitable metallic materials include, but are not limited to, zinc, magnesium, and iron.

In variations that include a metallic region, the device filament may be configured to degrade more slowly than the metallic region when exposed to bodily fluids. In some of these variations, the filament may be configured to delay, inhibit, or prevent degradation of the metallic region in a manner that allows the metallic region to provide additional mechanical support to the device filament over a selected period of time. This may occur by the filament shielding the metallic region from bodily fluids over a selected time period. A metallic region may start to degrade when the filament material is only partially degraded or may start to degrade when the filament material is completely degraded. In some variations, the metallic region may be configured to completely or almost completely degrade before the filament material completely degrades. In other variations, the filament material may be configured to completely or almost completely degrade before the metallic region completely degrades.

The devices may also comprise one or more flexible sections. The flexible sections may be selectively positioned to inhibit or prevent fracturing in the device when subjected to applied stresses during use. For example, the flexible sections may be placed within or near loops, in device variations having them. This may be helpful because stresses applied during use such as crimping, delivery, deployment, and the like, may cause deformation or strain in the structural elements of a device and may be greater in elements that are configured to bend (such as the loops). In some variations, the flexible section comprises a region having a cavity formed within the device including, but not limited to, a loop. Such a cavity may be formed by laser cutting, and may or may not be filled with a polymer or a polymer-solvent mixture.

When used, the flexible section(s) may have any suitable cross-sectional shape, including but not limited to, rectangular, circular, and oval. In some variations, the cross-section of the flexible section can vary through the thickness of the device. For example, the width of the flexible section along the length of a loop may be directly proportional to the magnitude of the strain along the loop when the device is under stress. In these variations, a flexible section may be widest at or proximate to the center of a bending portion of the loop and decrease in either direction along a length of the loop. Any number of flexible sections may be used, and in some variations, an individual loop may have two or more flexible sections. Multiple cavities may allow for reduction in strain in a high strain region without reducing the structural integrity of the device.

In device variations in which the filament comprises one or more polymers, the device may additionally contain one or more plasticizing agents. Plasticizing agents, may for example, be useful in increasing the total strain that can be experienced by a device filament before it fails (e.g., when the device no longer properly holds open and, if desired, expands a passageway or cavity, or when the device cracks and/or breaks in a high-strain regions). Cracks may be caused by crimping of the device prior to delivery, or by deployment of the device, and a plasticizing agent may help prevent the formation of such cracks. The plasticizing agent may leach out of the device after deployment at a target location, thus potentially aiding in the device rigidity, and potentially, mechanical integrity. The leaching of the plasticizing agent may be timed. For example, it may be timed to leach out as stress is placed on the device, thus potentially adding mechanical integrity when it needs it most.

It should be understood that the terms "plasticizer" and "plasticizing agent" are used interchangeably herein throughout. A plasticizing agent may include any agent or combination of agents that can be added to modify the mechanical properties of a polymeric composition or a product formed from a polymeric composition. In some variations, the plasticizing agent can be combined with a water-containing solvent or a lipid-containing solvent at temperatures that range from about room temperature to about body temperature to form a liquid or semi-solid. In other variations, the plasticizing agents can dissolve in a limited amount of water and leach from a polymeric material. In other variations, the plasticizing agent can dissolve in a bodily fluid.

Without intending to be bound by any theory or mechanism of action, it is thought that plasticizers may help reduce crystallinity, lower the glass-transition temperature ($T_g$), or reduce the intermolecular forces between polymers, creating or enhancing a flow between polymers in the composition. The mechanical properties that may be modified include, but are not limited to, Young's modulus, tensile strength, impact strength, tear strength, and strain-to-failure. The plasticizer can be monomeric, polymeric, co-polymeric, or a combination thereof, and can be added to a polymeric composition with or without covalent bonding.

Examples of classes of plasticizing agents include, but are not limited to, low molecular weight polymers such as, for example, single-block polymers, multi-block polymers, and copolymers; oligomers such as, for example, lactic acid oligomers including, but not limited to, ethyl-terminated oligomers of lactic acid; dimers of cyclic lactic acid and glycolic acid; small organic molecules; hydrogen bond forming organic compounds with and without hydroxyl groups; polyols such as low molecular weight polyols having aliphatic hydroxyls; alkanols such as butanols, pentanols and hexanols; sugar alcohols and anhydrides of sugar alcohols; polyethers such as poly(alkylene glycols); esters such as citrates, phthalates, sebacates and adipates; polyesters; aliphatic acids; saturated and unsaturated fatty acids; fatty alcohols; cholesterol; steroids; phospholipids such as, for example, lecithin; proteins such as animal proteins and vegetable proteins; oils such as, for example, the vegetable oils and animal oils; silicones; acetylated monoglycerides; diglycerides; triglycerides; amides; acetamides; sulfoxides; sulfones; pyrrolidones; oxa acids; diglycolic acids; and any analogs, derivatives, copolymers and combinations thereof.

In some variations, the plasticizers include, but are not limited to polyols such as, for example, caprolactone diol, caprolactone triol, sorbitol, erythritol, glucidol, mannitol, sorbitol, sucrose, and trimethylol propane. In other variations, the plasticizers include, but are not limited to, glycols such as, for example, ethylene glycol, diethylene glycol, triethylene glycol, tetraethylene glycol, propylene glycol, butylene glycol, 1,2-butylene glycol, 2,3-butylene glycol, styrene glycol, pentamethylene glycol, hexamethylene glycol; glycol-ethers such as, for example, monopropylene glycol monoisopropyl ether, propylene glycol monoethyl ether, ethylene glycol monoethyl ether, and diethylene glycol monoethyl ether; and any analogs, derivatives, copolymers and combinations thereof.

In still other variations, the plasticizers include, but are not limited to esters such as glycol esters such as, for example, diethylene glycol dibenzoate, dipropylene glycol dibenzoate, triethylene glycol caprate-caprylate; monostearates such as, for example, glycerol monostearate; citrate esters; organic acid esters; aromatic carboxylic esters; aliphatic dicarboxylic esters; fatty acid esters such as, for example, stearic, oleic, myristic, palmitic, and sebacic acid esters; triacetin; poly(esters) such as, for example, phthalate polyesters, adipate polyesters, glutate polyesters, phthalates such as, for example, dialkyl phthalates, dimethyl phthalate, diethyl phthalate, isopropyl phthalate, dibutyl phthalate, dihexyl phthalate, dioctyl phthalate, diisononyl phthalate, and diisodecyl phthalate; sebacates such as, for example, alkyl sebacates, dimethyl sebacate, dibutyl sebacate; hydroxyl-esters such as, for example, lactate, alkyl lactates, ethyl lactate, butyl lactate, allyl glycolate, ethyl glycolate, and glycerol monostearate; citrates such as, for example, alkyl acetyl citrates, triethyl acetyl citrate, tributyl acetyl citrate, trihexyl acetyl citrate, alkyl citrates, triethyl citrate, and tributyl citrate; esters of castor oil such as, for example, methyl ricinolate; aromatic carboxylic esters such as, for example, trimellitic esters, benzoic esters, and terephthalic esters; aliphatic dicarboxylic esters such as, for example, dialkyl adipates, alkyl allylether diester adipates, dibutoxyethoxyethyl adipate, diisobutyl adipate, sebacic esters, azelaic esters, citric esters, and tartaric esters; and fatty acid esters such as, for example, glycerol, mono- di- or triacetate, and sodium diethyl sulfosuccinate; and any analogs, derivatives, copolymers and combinations thereof.

In other variations, the plasticizers include, but are not limited to ethers and polyethers such as, for example, poly(alkylene glycols) such as poly(ethylene glycols) (PEG), poly(propylene glycols), and poly(ethylene/propylene glycols); PEG derivatives such as, for example, methoxy poly(ethylene glycol) (mPEG); and ester-ethers such as, for example, diethylene glycol dibenzoate, dipropylene glycol dibenzoate, and triethylene glycol caprate-caprylate; and any analogs, derivatives, copolymers and combinations thereof.

In other variations, the plasticizers include, but are not limited to, amides such as, for example, oleic amide, erucic amide, and palmitic amide; alkyl acetamides such as, for example, dimethyl acetamide; sulfoxides such as for example, dimethyl sulfoxide; pyrrolidones such as, for example, n-methyl pyrrolidone; sulfones such as, for example, tetramethylene sulfone; acids such as, for example, oxa monoacids, oxa diacids such as 3,6,9-trioxaundecanedioic acid, polyoxa diacids, ethyl ester of acetylated citric acid, butyl ester of acetylated citric acid, capryl ester of acetylated citric acid, and diglycolic acids such as dimethylol propionic acid; and any analogs, derivatives, copolymers and combinations thereof.

In other variations, the plasticizers include, but are not limited to vegetable oils including, but not limited to, epoxidized soybean oil; linseed oil; castor oil; coconut oil; fractionated coconut oil; epoxidized tallates; and esters of fatty acids such as stearic, oleic, myristic, palmitic, and sebacic acid; essential oils including, but not limited to, angelica oil, anise oil, arnica oil, aurantii aetheroleum, valerian oil, basilici aetheroleum, bergamot oil, savory oil, bucco aetheroleum, camphor, cardamomi aetheroleum, cassia oil, chenopodium oil, chrysanthemum oil, cinae aetheroleum, citronella oil, lemon oil, citrus oil, costus oil, curcuma oil, carlina oil, elemi oil, tarragon oil, eucalyptus oil, fennel oil, pine needle oil, pine oil, filicis, aetheroleum, galbanum oil, gaultheriae aetheroleum, geranium oil, guaiac wood oil, hazelwort oil, iris oil, hypericum oil, calamus oil, camomile oil, fir needle oil, garlic oil, coriander oil, carraway oil, lauri aetheroleum, lavender oil, lemon grass oil, lovage oil, bay oil, lupuli strobuli aetheroleum, mace oil, marjoram oil, mandarine oil, melissa oil, menthol, millefolii aetheroleum, mint oil, clary oil, nutmeg oil, spikenard oil, clove oil, neroli oil, niaouli, olibanum oil, ononidis aetheroleum, opopranax oil, orange oil, oregano oil, orthosiphon oil, patchouli oil, parsley oil, petit-grain oil, peppermint oil, tansy oil, rosewood oil, rose oil, rosemary oil, rue oil, sabinae aetheroleum, saffron oil, sage oil, sandalwood oil, sassafras oil, celery oil, mustard oil, serphylli aetheroleum, immortelle oil, fir oil, teatree oil, terpentine oil, thyme oil, juniper oil, frankincense oil, hyssop oil, cedar wood oil, cinnamon oil, and cypress oil; and other oils such as, for example, fish oil; and, any analogs, derivatives, copolymers and combinations thereof.

It should be appreciated that, in some variations, one of skill in the art may select one or more particular plasticizing agents in order to exclude any one or any combination of the above-described plasticizing agents. In some variations, the plasticizing agent can include a component that is water-soluble. In other variations, the plasticizing agent can be modified to be water-soluble. In some variations, the plasticizing agent can include a component that is lipid-soluble. In other variations, the plasticizing agent can be modified to be lipid-soluble. Any functional group can be added to modify the plasticizer's behavior in a solvent such as, for example, body fluids that are present in vivo. Any other suitable functional group may be used.

In some variations, the device contains one or more movable pieces, or one or more locking or interlocking pieces. For example, interlocking pieces may be desirable to help minimize inadvertent collapse of the device in use, from its expanded configuration, back to its compressed configuration, or to some fraction of its expanded configuration having less utility. Any number of locking or interlocking pieces may be used. For example, the device may be made completely from interlocking pieces, and these interlocking pieces may be fabricated from a single unitary material. The interlocking pieces may be made to operate in any suitable manner. In some variations, the interlocking pieces slide and lock into place, such as those pieces described in U.S. Pat. Nos. 6,033,436, 6,224,626, and 6,951,053, the disclosures of such features, are herein incorporated by reference in their entirety.

In variations in which the device has a crown shape, quasi-crown shape, diamond shape, or any of the other shapes described above, locking or interlocking pieces may be placed at locations between the peaks and the valleys (although they may indeed be placed at any suitable location or locations along the device). These pieces may be formed during device manufacture, or may be later attached to the device (e.g., when the device is in its compressed configuration). When the device is expanded, the locking pieces engage, preventing inadvertent, undesirable, or premature collapse of the device.

Illustrative Polymers

As described above, one or more components of the device may be made from a biodegradable polymer. The rate of biodegradation of the device components may be affected by a number of factors including, but not limited to, the type of material from which it is formed, the shape of the device, and the deployment conditions. Additionally, altering the cross-sectional area or cross-sectional shape of the polymer filament may affect degradation time. For example, a hollow filament will likely have a different degradation time than a solid filament of comparable size. As a result, choices of polymer filament materials and geometry may be varied depending on the location and treatment desired.

Examples of biodegradable polymers that may be suitable for use with the methods and devices describe here include, but are not limited to, aliginate, cellulose and ester, dextran, elastin, fibrin, hyaluronic acid, polyacetals, polyarylates (L-tyrosine-derived or free acid),poly($\alpha$-hydroxy-esters), poly($\beta$-hydroxy-esters), polyamides, poly(amino acid), polyalkanotes, polyalkylene alkylates, polyalkylene oxylates, polyalkylene succinates, polyanhydrides, polyanhydride esters, polyaspartimic acid, polybutylene diglycolate, poly(caprolactone), poly(caprolactone)/poly(ethylene glycol) copolymers, poly(carbonate), L-tyrosine-derived polycarbonates, polycyanoacrylates, polydihidropyrans, poly(dioxanone), poly-p-dioxanone, poly(epsilon-caprolactone), poly(epsilon-caprolactone-dimethyltrimethylene carbonate), poly(esteramide), poly(esters), aliphatic polyesters, poly(etherester), poly(ethylene glycol)/poly(orthoester) copolymers, poly(glutarunic acid), poly(glycolic acid), poly (glycolide), poly(glycolide)/poly(ethylene glycol) copolymers, poly(glycolide-trimethylene carbonate), poly(hydroxyalkanoates), poly(hydroxybutyrate), poly (hydroxybutyrate-co-valerate), poly(imino carbonates), polyketals, poly(lactic acid), poly(lactic acid-co-glycolic acid), poly(lactic acid-co-glycolic acid)/poly(ethylene glycol) copolymers, poly(lactide), poly(lactide-co-caprolactone), poly(DL-lactide-co-glycolide), poly(lactide-co-glycolide)/poly(ethylene glycol) copolymers, poly(lactide)/poly(ethylene glycol) copolymers, poly(lactide)/poly (glycolide) copolymers, polyorthoesters, poly(oxyethylene)/poly(oxypropylene) copolymers, polypeptides, polyphosphazenes, polyphosphoesters, polyphosphoester urethanes, poly(propylene fumarate-co-ethylene glycol), poly(trimethylene carbonate), polytyrosine carbonate, polyurethane, PorLastin or silk-ealastin polymers, spider silk, tephaflex, terpolymer(copolymers of glycolide,lactide or dimethyltrimethylene carbonate), and combinations, mixtures or copolymers thereof.

Drug Delivery

When the devices are configured for drug delivery, the amount of drug released from the device will depend on the desired dosage. Each drug should be released at a rate that provides a patient with a healthy, safe, and effective dosage and should be administered at a dosage that is also healthy, safe, and effective. In some variations, for example when the devices are used to treat one or more conditions of the sinuses, the devices may be configured to deliver mometasone furoate at a daily dosage of about 500 µg or less per day. In other variations, the devices are configured to deliver mometasone furoate at a daily dosage of about 200 µg, between about 5 µg to about 100 µg, between about 5 µg to about 60 µg, between about 5 µg to about 40 µg, between about 5 µg to about 20 µg, between about 5 µg to about 10 µg, between about 10 µg to about 100 µg, between about 10 µg to about 60 µg, between about 10 µg to about 40 µg, between about 10 µg to about 20 µg, between about 20 µg to about 100 µg, between about 20 µg to about 60 µg, between about 20 µg to about 40 µg, between about 40 µg to about 100 µg, between about 40 µg to about 60 µg, between about 60 µg to about 100 µg, and the like.

Drugs may be released at a constant rate from the device, but need not be. Indeed, the devices may be configured with any suitable release rate profile. In some variations, the daily amount of drug released may decrease over time. For example, a device may release a certain amount of drug (e.g. between about 40 µg and about 60 µg) for a first period of time (e.g. one week), then may release a second amount of drug (e.g. between about 20 µg and about 40 µg) for a second period of time. Similarly, the amount of drug delivered may change any number of times during a span of time. Furthermore, multiple drug eluting layers may be used, and each layer may be configured to have a different and specific release profile. Of course, it should be understood that each layer may comprise, contain, include, or be configured to release one or more than one drug or agent therefrom. When multiple layers are used each layer may comprise, contain, include, or be configured to release the same or a different drug or agent therefrom. Similarly, a filament comprising drug particles may be used to provide a different release profile from that of the drug eluting layer. Additionally, as described below, drug depots may be used to achieve a varied release profile.

In still further variations, the device may comprise one or more barrier layers. These layers may or may not release one or more drugs, and may delay the release of one or more drugs from one or more drug releasing layers. The barrier layer may or may not be a bulk-eroding polymer, or may or may not be a surface-eroding polymer. In some variations, the barrier layer may prevent the passage of drug therethrough. In these variations, the barrier layer may provide a time during which no drug is released from at least a portion of a drug releasing layer. Once the barrier layer has sufficiently degraded or otherwise eroded, drug release may resume. In other variations, the barrier layer may allow some amount drug to pass therethrough. In some of these variations, the amount of drug that passes through barrier layer may be less than that which would be released from the drug releasing layer in the absence of the barrier layer. The barrier layer thus may provide a period during which a smaller amount of drug is released from at least a portion of the drug releasing layer. Once the barrier layer has sufficiently degraded or otherwise eroded, the amount of drug released from the device may increase.

These variations, and combinations thereof, may allow the device to provide a variable drug release profile, or provide bursts, either initial or delayed, in addition to the device's baseline release profile. Additionally, these variations may allow the device to provide different drug release profiles that are separated in time. For example, the device may comprise two drug releasing layers separated by a barrier layer. The outer drug releasing layer may release an initial amount of drug over an initial period of time, and may follow any suitable drug release profile. The barrier layer may then degrade or erode over a certain period of time, during which some or no drug is released from a second drug releasing layer. Once this degradation has occurred, the second drug releasing layer may then release a second amount of drug over a second period of time, and this release may also follow any suitable drug release profile. Each drug releasing layer may release any suitable amount of any suitable drug over any suitable amount of time, as described above.

Additionally, one or more release rate modifiers may also be used. The release rate modifier may be any suitable biocompatible material that serves to alter the rate at which a drug is released from the device. In some variations, the release rate modifier may include a hydrophilic agent. In some variations, the release rate modifier is a polyethylene glycol, e.g., a polyethylene glycol with a molecular weight of between about 3000 to about 13000, between about 3000 to about 11000, between about 3000 to about 9000, between about 3000 to about 7000, between about 3000 to about 5000, between about 5000 to about 13000, between about 5000 to about 11000, between about 5000 to about 9000, between about 5000 to about 7000, between about 7000 to about 13000, between about 7000 to about 11000, between about 7000 to about 9000, between about 9000 to ab out 13000, between about 9000 to about 11000, between about 11000 to about 13000, and the like. In some variations, the release rate modifier is a polyethylene glycol with a molecular weight of about 6000.

In some variations, the device may be configured to deliver multiple drugs, which drugs may or may not be encapsulated (e.g., in a microreservoir or other material). In some variations, multiple types of drug particles are contained within a single drug eluting layer. In other variations, the drug eluting layer is discontinuous, having different sections containing different drugs. In these variations, the different sections may have different compositions, and thus may also provide differing release rates. In still other variations, multiple drug eluting layers may be used, where each layer contains a different drug or combination of drugs. Drug depots, as described above, may also hold different drugs therein or may collectively release different drugs than those released by the drug eluting layer. In still other variations, the filament may release a different drug or combination of drugs than those drugs released by the drug eluting layer or layers. Any combination of these variations may also be used to achieve the desired drug delivery profiles.

Illustrative Agents

The device may comprise any suitable drug or agent, and the agent selected will largely be determined by the desired use of the device. It should be understood that the terms "agent" and "drug" are used interchangeably herein throughout. The device may comprise, for example, a diagnostic agent, or may comprise a therapeutic agent. Diagnostic agents may be used, for example, in diagnosing the presence, nature, and/or extent of a disease or medical condition in a subject. Thus for example, the diagnostic agent may be any agent suitable for use in connection with methods for imaging an internal region of a patient and/or diagnosing the presence or absence of a disease in a patient.

Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, fluorescence imaging, positron emission tomography (PET), radiofrequency (RF) and microwave laser. Diagnostic agents may also include any other agent useful in facilitating diagnosis of a disease or other condition in a patient, whether or not imaging methodology is employed.

Examples of specific diagnostic agents include radioopaque materials such as iodine or iodine-derivatives, for example, iohexal and iopamidol. Other diagnostic agents such as, for example, radioisotopes, are detectable by tracing radioactive emissions. Examples of agents detectable by MRI are generally paramagnetic agents including, but not limited to, gadolinium chelated compounds. An examples of an agent detectable by ultrasound includes, but is not limited to, perflexane. An example of a fluorescence agent includes, but is not limited to, indocyanine green. Examples of agents used in diagnostic PET include, but are not limited to, fluorodeoxyglucose, sodium fluoride, methionine, choline, deoxyglucose, butanol, raclopride, spiperone, bromospiperone, carfentanil, and flumazenil.

The device may also comprise any suitable therapeutic agent. Suitable classes of therapeutic agents include, for example, anti-inflammatory agents, anti-allergens, anti-cholinergic agents, antihistamines, anti-infectives, anti-platelet agents, anti-coagulants, anti-thrombic agents, anti-scarring agents, anti-proliferative agents, chemotherapeutic agents, anti-neoplastic agents, decongestants, healing promoting agents and vitamins (for example, retinoic acid, vitamin A, depaxapanthenol, vitamin B and their derivatives), hypersomolar agents, immunomodulators, immunosuppressive agents, and combinations and mixtures thereof.

Anti-infective agents generally include antibacterial agents, antifungal agents, antiparasitic agents, antiviral agents, and antiseptics. Anti-inflammatory agents generally include steroidal and nonsteroidal anti-inflammatory agents.

Examples of antiallergic agents that may suitable for use with the described methods and devices include, but are not limited to, pemirolast potassium (ALAMAST®, Santen, Inc.), and any prodrugs, metabolites, analogs, homologues, congeners, derivatives, salts and combinations thereof. Examples of antiproliferative agents include, but are not limited to, actinomycin D, actinomycin IV, actinomycin $I_1$, actinomycin $X_1$, actinomycin $C_1$, and dactinomycin (COSMEGEN®, Merck & Co., Inc.). Examples of antiplatelet, anticoagulant, antifibrin, and antithrombin agents include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibodies, recombinant hirudin, and thrombin inhibitors (ANGIOMAX®, Biogen, Inc.), and any prodrugs, metabolites, analogs, homologues, congeners, derivatives, salts and combinations thereof. Examples of pro-healing agents include, but are not limited to, sirolimus, everolimus, temsiolimus, and vitamin A.

Examples of cytostatic or antiproliferative agents that may be suitable for uses with the described methods and devices include, but are not limited to, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof.

Examples of antibacterial agents that may be suitable for use with the described methods and devices include, but are not limited to, aminoglycosides, amphenicols, ansamycins, β-lactams such as penicillins, lincosamides, macrolides, nitrofurans, quinolones, sulfonamides, sulfones, tetracyclines, vancomycin, and any of their derivatives, or combinations thereof. Examples of penecillins that may be suitable for use with the described methods and devices include, but are not limited to, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benetamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin.

Examples of antifungal agents suitable for use with the described methods and devices include, but are not limited to, allylamines, imidazoles, polyenes, thiocarbamates, triazoles, and any of their derivatives. Antiparasitic agents that may be employed include, but are not limited to, atovaquone, clindamycin, dapsone, iodoquinol, metronidazole, pentamidine, primaquine, pyrimethamine, sulfadiazine, trimethoprim/sulfamethoxazole, trimetrexate, and combinations thereof.

Examples of antiviral agents suitable for use with the described methods and devices include, but are not limited to, acyclovir, famciclovir, valacyclovir, edoxudine, ganciclovir, foscarnet, cidovir (vistide), vitrasert, formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomet-hoxy)propyl) guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxami-de), LY253963 (1,3,4-thiadiazol-2-yl-cyanamide), RD3-0028 (1,4-dihydro-2,3-Benzodithiin), CL387626 (4,4'-bis[4,6-d][3-aminophenyl-N-,N-bis(2-carbamoylethyl)-sulfonilimino]-1,3,5-triazin-2-ylamino-biphenyl-2-,2'-disulfonic acid disodium salt), BABIM (Bis[5-Amidino-2-benzimidazoly-1]-methane), NIH351, and combinations thereof.

Examples of antiseptic agents suitable for use with the described methods and devices include, but are not limited to, alcohol, chlorhexidrine, iodine, triclosan, hexachlorophene, and silver-based agents, for example, silver chloride, silver oxide, and silver nanoparticles.

Anti-inflammatory agents may include steroidal and nonsteroidal anti-inflammatory agents. Examples of suitable steroidal anti-inflammatory agents include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof.

Examples of suitable nonsteroidal anti-inflammatory agents include, but are not limited to, COX inhibitors. These COX inhibitors may include COX-1 or COX nonspecific inhibitors such as, for example, salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone. The COX inhibitors may also include selective COX-2 inhibitors such as, for example, diaryl-substituted furanones such as rofecoxib; diaryl-substituted pyrazoles such as celecoxib; indole acetic acids such as etodolac and sulfonanilides such as nimesulide).

Examples of chemotherapeutic/antineoplastic agents that may be used in the devices described here include, but are not limited to antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites or other agents that block cancer cell growth by interfering with certain cell functions, usually DNA synthesis (e.g., 6-mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin), plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase ingibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000), which is expressly incorporated herein by reference, biological response modifiers (e.g., interferon, bacillus calmette-guerin (BCG), monoclonal antibodies, interleukin 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol or paclitaxel, taxotere, azathioprine, docetaxel analogs/congeners, derivatives of such compounds, and combinations thereof.

Examples of decongestants that may be used in the devices and methods described here include, but are not limited to, epinephrine, pseudoephedrine, oxymetazoline, phenylephrine, tetrahydrozolidine, and xylometazoline. Examples of mucolytics that may be used in the devices and methods described here include, but are not limted to, acetylcysteine, dornase alpha, and guaifenesin. Anti-histamines such as azelastine, diphenhydramine, and loratidine may also be used in the methods and devices described here.

Suitable hyperosmolar agents that may be used in the devices described here include, but are not limited to, furosemide, sodium chloride gel, and other salt preparations that draw water from tissue or substances that directly or indirectly change the osmolarity of the mucous layer.

Other bioactive agents useful in the present invention include, but are not limited to, free radical scavengers; nitric oxide donors; rapamycin; methyl rapamycin; everolimus; tacrolimus; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells including, but not limited to prokaryotes and eukaryotes such as, for example, epithelial cells and genetically engineered epithelial cells; dexamethasone; and, any prodrugs, metabolites, analogs, homologues, congeners, derivatives, salts and combinations thereof.

Examples of free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (TEMPOL), 2,2',3,4,5,5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate, and any analogs, homologues, congeners, derivatives, salts and combinations thereof.

Delivery Devices

Also described here are delivery devices which may be used to deliver one or more of the self-expanding devices described above. While generally described here as being used to deliver the self-expanding devices described above, it is important to realize that the delivery devices may be used to deliver any suitable implant or implants. Indeed, the delivery devices may be used to deliver one or more self-expanding devices, non-expanding devices, expandable devices, swellable devices, shape-changing devices, a combination thereof, or the like. The implant or implants delivered may have any suitable size, shape, and configuration, and in some instances may be tailored to the anatomy into which the implant will be delivered, which may be any suitable portion of the anatomy. For example, in some variations the delivery devices may deliver one or more implants to one or more of the paranasal sinuses. In other variations, the delivery devices may be used to deliver one or more devices to other portions of the anatomy, such as the Eustachian tube, the urethra, or the tonsils.

The delivery devices typically comprise a cannula defining a lumen, aperture or other opening for retaining an implant therein. When the delivery device is used to deliver a self-expanding device, the delivery device may be configured to house the self-expanding device in a compressed or unexpanded configuration. The delivery devices may be operated single-handedly and may be ergonomically designed to help the operator deliver and deploy the device. In some variations, endoscopic guidance, or other forms of visualization, such as ultrasound or fluoroscopy, may be used to aid in delivery. The delivery device may be configured for a single use (e.g., be terminally sterilized with e-beam radiation) or may be configured for multiple uses (e.g., be capable of being sterilized multiple times). In some variations, one or more components of the delivery device may be configured for a single use while one or more components may be configured for multiple uses.

Figure 5A:
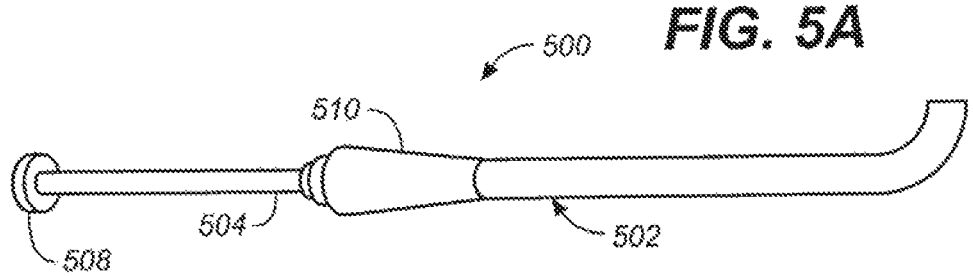
FIGS. 5A and 5B provide illustrative examples of various delivery devices that may be useful with the devices and methods described here.

FIG. 5A depicts one variation of a suitable delivery device. As shown there, delivery device (500) comprises a cannula (502) defining a lumen (not shown), inside which one or more implants may be housed. Also shown there is pusher (504) which is connected to plunger (508) and is slidably disposed within handle body (510). While the deployment actuation shown here is in the form of a push rod mechanism, any suitable actuation mechanism may be used, as will be described in more detail below. In the variation shown in FIG. 5A, pusher (504) is slidable within the lumen of the cannula (502), so that as plunger (508) is moved distally relative to handle body (510), pusher (504) is advanced distally and may force an implant from the cannula's distal end.

Figure 5B:
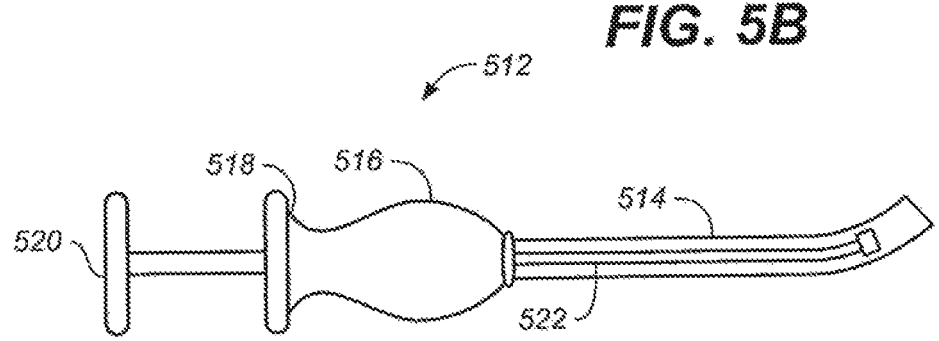

In the variation shown in FIG. 5A, the proximal end of the cannula (502) is connected to handle body (510). In some variations, this connection may be reversible or releasable such that the cannula (502) may be disengaged from handle body (510). The handle body (510) may help enable single-handed use, and provide for an intuitive and ergonomic user interface. For example, the handle body (510) shown in FIG. 5A is designed so that the operator will grip it in a "pen-like" fashion, while actuating the plunger (508) to deliver the implant as described above. FIG. 5B depicts another variation of delivery device (512) having a similar configuration of elements, but designed to be held in a "syringe-like" fashion. Shown there is cannula (514), handle body (516) comprising grips (518), and plunger (520) attached to pusher (522). In these variations, an operator may use one or more fingers to grasp grips (518), and may apply pressure to plunger (520) (e.g., with one's thumb) to advance pusher (522).

Cannula

Figure 5C:
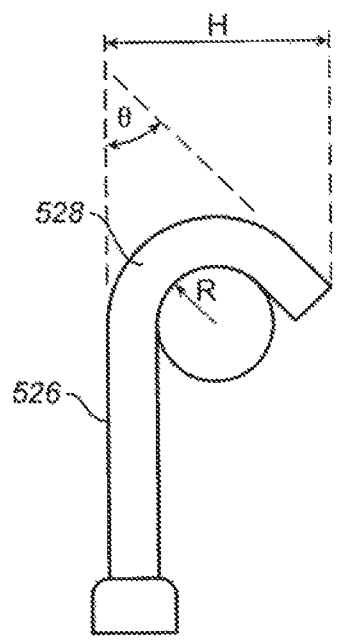
FIG. 5C highlights various dimensions associated with the delivery devices described here.

While shown in FIGS. 5A and 5B as having a single curve at the distal portion thereof, the cannula may be shaped in any manner and may have any number of shaped curves. In some variations, the cannula may be pre-shaped. In other variations, the shape of the cannula may be set or changed during delivery. In variations that include one or more shaped curves, the shaped curves may have any suitable dimensions. Indeed, FIG. 5C illustrates a curved cannula (526), and highlights some of the relevant dimensions that may be associated with the shaped curve. Shown there is cannula (526) having a curve (528) with a radius of curvature (R), an angle (θ), and a curve height (H). These dimensions may be of any suitable value or range, depending on the intended use of the device and the size of the intended implant.

For example, when delivering implants to the frontal sinuses or the maxillary sinuses, curve (528) may have any suitable angle (θ). Suitable angles (θ) include, but are not limited to, about 50°, about 60°, about 70°, about, 80°, about 90°, about 100°, about 110°, and about 120°. In some variations the angle (θ) may between about 50° and about 120°, between about 60° and about 120°, between about 70° and about 120°, between about 80° and about 120°, between about 90° and about 120°, between about 100° and about 120°, between about 110° and about 120°, between about 50° and about 110°, between about 60° and about 110°, between about 70° and about 110°, between about 80° and about 110°, between about 90° and about 110°, between about 100° and 110°, between about 50° and about 100°, between about 60° and about 100°, between about 70° and about 100°, between about 80° and about 100°, between about 90° and about 100°, between about 50° and about 90°, between about 60° and about 90°, between about 70° and about 90°, between about 80° and about 90°, between about 50° and about 80°, between about 60° and about 80°, between about 70° and about 80°, between about 50° and about 70°, between about 50° and about 70°, or between about 60° and about 70°. Furthermore, suitable radii of curvature (R) for delivery to the frontal sinuses include, but are not limited to about 6 mm, about 7 mm, about 8 mm, about 9 mm, about 10 mm, about 11 mm and about 12 mm. In some variations the radius of curvature (R) may be between about 6 mm and about 12 mm, between about 7 mm and about 12 mm, between about 8 mm and about 12 mm, between about 8 mm and about 12 mm, between about 9 mm and about 12 mm, between about 10 mm and about 12 mm, between about 11 mm and about 12 mm, between about 6 mm and about 11 mm, between about 7 mm and about 11 mm, between about 8 mm and about 11 mm, between about 9 mm and about 11 mm, between about 10 mm and about 11 mm, between about 6 mm and about 10 mm, between about 7 mm and about 10 mm, between about 8 mm and about 10 mm, between about 9 mm and about 10 mm, between about 6 mm and about 9 mm, between about 7 mm and about 9 mm, between about 8 mm and about 9 mm, between about 6 mm and about 8 mm, between about 7 mm and about 8 mm, or between about 6 mm and about 7 mm. Suitable heights (H) for delivery to the frontal or maxillary sinuses include, but are not limited to, about 23 mm, about 25 mm, about 28 mm, and about 30 mm. Additionally, in some variations height (H) may be between about 23 mm and about 30 mm, between about 25 mm and about 30 mm, between about 28 mm and about 30 mm, between about 23 mm and about 28 mm, between about 25 mm and about 28 mm, or between about 23 mm and about 25 mm.

Similarly, when delivering implants to the ethmoid sinuses, suitable angles (θ) include, but are not limited to, about 10°, about 20°, about 30°, about 40°, about 50°, about 60°, about 70°, about 80°, about 90°, about 100°, and about 110°. In some variations, the angle (θ) may be between about 10° and about 110°, between about 30° and about 110°, between about 50° and about 110°, between about 70° and about 110°, between about 90° and about 110°, between about 10° and about 90°, between about 30° and about 90°, between about 50° and about 90°, between about 70° and about 90°, between about 10° and about 70°, between about 30° and about 70°, between about 50° and about 70°, between about 10° and about 50°, between about 30° and about 50°, or between about 10° and about 30°. Examples of suitable radii of curvature (R) for delivery to the ethmoid sinuses include, but are not limited to about 17 mm, about 19 mm, about 21 mm, about 23 mm, about 25 mm, and about 27 mm. In some variations, the radius of curvature (R) may be between about 17 mm and about 27 mm, between about 19 mm and about 27 mm, between about 21 mm and about 27 mm, between about 23 mm and about 27 mm, between about 25 mm and about 27 mm, between about 17 mm and about 25 mm, between about 19 mm and about 25 mm, between about 21 mm and about 25 mm, between about 23 mm and about 25 mm, between about 17 mm and about 23 mm, between about 19 mm and about 23 mm, between about 21 mm and about 23 mm, between about 17 mm and about 21 mm, between about 19 mm and about 21 mm, or between about 17 mm and about 19 mm. Suitable heights (H) for delivery to the frontal or maxillary sinuses include, but are not limited to, about 23 mm, about 25 mm, about 28 mm, and about 30 mm. Additionally, in some variations height (H) may be between about 23 mm and about 30 mm, between about 25 mm and about 30 mm, between about 28 mm and about 30 mm, between about 23 mm and about 28 mm, between about 25 mm and about 28 mm, or between about 23 mm and about 25 mm.

Additionally, the cannula may define an inner diameter that may house implants of any number of sizes. The inner diameter of the cannula may or may not be constant along the length of the cannula. Indeed, in some variations the inner diameter of the cannula may vary throughout the length of the cannula, or the cannula may be made of a material that may stretch or deform when holding an implant therein. In some of these variations, the inner diameter of the cannula may be substantially smaller than one or more implants to be delivered, but may stretch to accommodate the one or more implants. By allowing the cannula to have a smaller profile while still being able to hold the same-sized implant, an operator is given additional space in the body into which other devices, such as an endoscope, may be placed.

Examples of suitable inner diameters of the cannula include, but are not limited to, about 0.05 mm, about 1 mm, about 2 mm, about 3 mm, about 4 mm, about 5 mm, about 6 mm, or greater than about 7 mm. In some variation the inner diameter may be between about 0.05 mm and about 6 mm, between about 1 mm and about 6 mm, between about 2 mm and about 6 mm, between about 3 mm and about 6 mm, between about 3 mm and about 6 mm, between about 4 mm and about 6 mm, between about 5 mm and about 6 mm, between about 0.05 mm and about 5 mm, between about 1 mm and about 5 mm, between about 2 mm and about 5 mm, between about 3 mm and about 5 mm, between about 4 mm and about 5 mm, between about 0.05 mm and about 4 mm, between about 1 mm and about 4 mm, between about 2 mm and about 4 mm, between about 3 mm and about 4 mm, between about 0.05 mm and about 3 mm, between about 1 mm and about 3 mm, between about 2 mm and about 3 mm, between about 0.05 mm and about 2 mm, between about 1 mm and about 2 mm, or between about 0.05 mm and about 1 mm.

As mentioned above, in some variations the shape of the cannula may be set or changed during operation of the device. Indeed, while one or more portions of the cannula may be preset in shape, one or more portions of the cannula may be flexible, bendable, or otherwise lacking in a set shape. In some of these variations, one or more inserts may be placed into the cannula to give any flexible portions a set shape. These inserts may be any size, shape, or configuration. In some variations, the insert may be a rigid tube. In other variations, the insert may be a rigid wire. These variations may find particular utility in instances when the cannula has two or more lumens, as will be described in more detail below.

In other variations, the cannula may be steerable or have one or more features that may lock an otherwise flexible cannula into a set shape. The cannula may or may not be configured for remote or robotic operation, and may or may not have one or more articulated or articulable segments. FIGS. 23A and 23B illustrate one variation of a steerable and lockable delivery device (2300). Shown there is flexible cannula (2302), skeleton (2304), and left (2306) and right (2308) control lines for controlling cannula (2302). Skeleton (2304) may be configured to freely flex between a straight configuration, as shown in FIG. 23A, a left-curved configuration, as shown in FIG. 23B, and a right-curved configuration (not shown). This free movement may be constrained by placing tension on one or both of left (2306) and right (2308) control lines. More specifically, if equal tension is placed on both left (2306) and right (2308) control lines, then the cannula (2302) may be held in the straight configuration shown in FIG. 23A. If greater tension is placed on left control line (2306), then cannula (2302) may bend to the left. Conversely, if greater tension is placed on right control line (2308), cannula (2302) may bend to the right. Depending on the amount of tension placed on left (2306) and right (2308) control lines, cannula (2302) may be held in a certain configuration despite externally applied forces. In some variations the delivery device is configured such that the device naturally places left (2306) and right (2308) control lines under a predetermined amount of tension, and the user may temporarily release the tension to allow cannula (2302) to become flexible. It is important to note that although delivery device (2300) is shown in FIGS. 23A and 23B as having two control lines and a cannula (2302) that is able to bend in two directions, delivery device (2300) may have any number of control lines and cannula (2302) may able to bend in any corresponding number of directions. Indeed, cannula (2300) may have one, two, three, or four or more control lines, and may have a skeleton (2304) that may bend cannula (2302) in one, two, three, or four or more directions.

The cannula may be made of any suitable or desirable material. Examples of suitable cannula materials include, but are not limited to, polyvinyl chloride, Pebax®, polyethylene, silicone rubber, polyurethane, and any analogs, homologs, congeners, derivatives, copolymers, and mixtures thereof. In some variations, the cannula may comprise one or more metals or metal alloys, such as, but not limited to, magnesium, nickel-cobalt alloys, nickel-titanium alloys, copper-aluminum-nickel alloys, copper-zinc-aluminum-nickel alloys, combinations thereof and the like. The cannula may be made of one material, or may be made from a mixture or combination of different materials. In some variations, one portion of the cannula may be made of one or more materials, while another portion of the cannula may be made from a different material or combination of materials. In other variations, one or more portions of the cannula may be braided to increase the strength or rigidity of the cannula. Additionally, the cannula may or may not be made of translucent or transparent materials. Transparent or translucent materials may allow an operator to directly visualize an implant's positioning while the implant is housed within the cannula.

The distal end, or tip, of the cannula may have any suitable dimensions or configuration. For example, the cannula tip may or may not have the same diameter as the rest of the cannula. Similarly, the cannula tip may or may not be made of the same material or materials as the rest of the cannula. In some variations the cannula tip is made of a soft, atraumatic material, in order to minimize damage during delivery and deployment. Additionally, the shape of the cannula or cannula tip may help minimize damage during delivery and deployment. For example, the edges of the cannula tip may be rounded or beveled to further minimize tissue trauma. In some of these variations, the cannula tip may be deformable. In these variations, an operator may deform a cannula tip either before or after one or more implants have been placed within the cannula. For example, an operator may use one or more tools to compress a cannula tip having a circular cross-sectional shape, which may deform the tip to take on an oval cross-sectional shape. This may allow the tip to more easily pass through adjoining tissues. Additionally, the tip may again be deformed when the one or more implants is ejected from the cannula.

In some variations, the cannula tip may include one or more features or components that may aid in advancement of the delivery device or delivery/deployment of one or more implants. FIGS. 24A-24P illustrate different variations of suitable cannula tips. It is important to note that the tip features or components described here may or may not be integral to the cannula tip. Indeed, any of the cannula tips described here may be formed separately from, and later attached to, the delivery device. These attachable tips may be configured to attach to the standard, cylindrical cannula tip, as shown in FIGS. 5A and 5B, or may be configured to attach to any one of the cannula tips described below. Attachable tips may provide a user considerable leeway in choosing a cannula tip that is appropriate for a given set of circumstances without needing to replace the entire cannula or delivery device. These attachable tips may be attached in any suitable manner, including, but not limited to, press fitting, welding (e.g. heat welding, ultrasonic welding, tacking, staking, and the like), chemical bonding, mechanical attachment (sutures, clamps, clips or other mechanical fasteners), or attachment using adhesives (glues, adhesive polymers and the like) or other materials (sugars, low melting-temperature polymers and the like), or some combination thereof. The attachable tips may or may not permanently attach to the cannula. Indeed, in some variations the attachable tips may be releasably attached to the cannula. When releasable, the attachable tips may be released within the body, or may be released outside of the body. When released in a body, an attachable tip may or may not be biodegradable, and may or may not be removed by aspiration or another suitable manner. Additionally, the attachable tips may serve an additional function in the body such as drug delivery, stenting, or acting as a marker.

In some variations, the cannula tip may comprise one or more markers that may aid in visualization of the cannula. FIG. 24A depicts one such variation of cannula tip (2400) having marker (2402). In some variations, marker (2402) may be configured to aid in direct visualization of the cannula. Indeed, when the cannula is substantially transparent, the marker may be opaque or otherwise non-transparent, which may in turn allow an operator to identity and differentiate the cannula tip from the cannula body. Similarly, the marker may be of a different color from the cannula body, or may reflect different amounts of light than the cannula body. Marker (2402) may or may not be a radiographic or ultrasonic marker, and may or may not aid in indirect visualization of the cannula through methods such as ultrasound and fluoroscopy. In still other variations, marker (2402) is configured to emit one or more signals that may be detected by one or more visualization devices. Cannula tip (2400) may additionally have any number or combination of markers as described above.

FIGS. 24B and 24C show another variation of cannula tip (2404) comprising an expandable funnel-shaped tip (2406). Funnel-shaped tip (2406) may or may not be collapsible to a low profile configuration, as shown in FIG. 24B. Funnel-shaped tip (2406) may be held in a low profile configuration by a sheath or other restraining device (not shown) and when expanded may aid an operator in positioning the cannula tip (2404) relative to an opening, such as a sinus ostium. Once cannula tip (2404) has been passed through the opening, the sheath or restraining device may be removed, and funnel-shaped tip (2406) may expand to an expanded configuration, as shown in FIG. 24C. Funnel-shaped tip (2406) may or may not self-expand to its expanded configuration, and may or may not be configured to expand in response to one or more stimuli. Additionally, while shown in FIG. 24C as being frustoconical in shape, funnel-shaped tip may have any cross-sectional profile. Once funnel-shaped tip (2406) is expanded, the cannula may be withdrawn proximally relative to the opening. The increasing diameter of funnel-shaped tip (2406) may resist passage through the opening, which may provide a user with tactile feedback of the cannula tip's positioning relative to the opening. Once the one or more implants have been delivered, the funnel-shaped tip (2406) may or may not be withdrawn into the restraining device to resume its low-profile configuration.

A funnel-shaped tip (2406) may also aid in controlled delivery of one or more self-expanding devices. For example, funnel-shaped tip (2406) may be used to help ensure implant placement adjacent to a tissue wall. Once expanded, funnel-shaped tip (2406) may be placed against a tissue wall, and the self-expanding device may be advanced into funnel-shaped tip (2406) where the self-expanding device may at least partially expand. Funnel-shaped tip (2406) may then be withdrawn away from the tissue wall to leave the implant in place.

Additionally, in some variations cannula tip may have one or more protrusions. FIG. 24D shows one such variation of cannula tip (2408) comprising olive tip (2410). Olive tip (2410) may aid in dilation of a passage opening and may temporarily or permanently displace one or more obstructions such as a nasal polyp. Furthermore, due to its rounded nature, olive tip (2410) may reduce the risk of tissue damage that may be sustained in dilation or displacement. Additionally, depending on the dimensions of olive tip (2410), olive tip (2410) may have a sealing function when it engages an opening. This may allow a user to introduce a fluid through the cannula without the fluid passing through the opening, which may provide particular utility in instances where it is desirable to flush or fill a sinus with a liquid or gas without that liquid or gas leaving the sinus cavity through the sinus ostium.

While shown in FIG. 24D as being olive-shaped, cannula tip (2408) may have a protrusion of any suitable shape, dimensions or configuration of elements, which may be located anywhere along the length of cannula tip (2408). Indeed, the protrusion may be wedge-shaped, frustoconical, oval, or have any three-dimensional shape of regular or irregular geometry. In some of these variations, the protrusion may provide or more additional functions. For example, FIG. 24E depicts cannula tip (2412) comprising a wedge-shaped protrusion (2414). In addition to the potential dilating, displacing, or sealing functions described above, a wedge-shaped tip may provide a structure that allows an attachable tip may be removed from the cannula. The wedge-shaped protrusion (2414) may be passed through an opening (not shown), potentially temporarily dilating that opening in the process. If the widest diameter of the wedge shaped portion (2414) is wider than the diameter of the opening, the opening may resist a return trip of the cannula tip (2412) through the opening. Assuming wedge-shaped portion (2414) is a part of an attachable tip, this resistance may provide a force sufficient to release the attachable tip from the cannula.

FIGS. 24F and 24G show a frontal view and a side view, respectively, of another variation of cannula tip (2416) having a plate extension (2418). Plate extension (2418) may be substantially flat, or may have one or more curves. Generally speaking, plate extension (2418) provides a lower profile portion that may allow cannula tip (2416) to maneuver between adjoining tissues. Because the plate extension (2418) is thinner than the body (2420) of cannula tip (2416) along one plane, as illustrated in FIG. 24G, plate extension (2418) may be better able to wedge between two touching tissues (not shown). Once the plate extension (2418) has been placed within two tissues, the cannula tip (2416) may or may not be rotated to separate the two tissues. In some variations, the plate extension (2418) increases in thickness or curves to join with body (2420).

Additionally, plate extension (2418) may allow for directional delivery of one or more implants. For example, when a self-expanding device is passed out of the aperture (2422) of cannula tip (2416), plate extension (2418) may limit the directions in which the self-expanding device may expand relative to cannula tip (2416). For instance, if cannula tip (2416) is positioned as shown in FIG. 24G, a self-expanding device, when released from aperture (2422), may expand toward the left. This directional expansion may allow a user to control the placement and expansion of a self-expanding member. For example, a user may position cannula tip (2416) and plate extension (2418) next to a tissue wall (not shown). As a self-expanding device is released from aperture (2422), its expansion may be constrained by the tissue wall on one side and the plate extension (2418) on the other. A user may then move cannula tip (2416) away from the tissue wall to allow the self-expanding device to continue expanding.

Still other cannula tips may comprise one or more slots or prongs. Indeed, FIGS. 24H and 24I illustrate a variation of cannula tip (2424) comprising slots (2426) and prongs (2428). The cannula tip (2424) may comprise any suitable number of slots (2426) and prongs (2428) (e.g., one, two, three, four, five six, seven, eight, or nine or more), although generally the number of slots (2426) and prongs (2428) will be the same. Additionally, each slot (2426) and prong (2428) may have any suitable size, shape, and configuration, and each slot (2426) and prong (2428) may or may not have the same size, shape, or configuration. Indeed, slots (2426) and prongs (2428) may be rectangular, triangular, curved, sinusoidal, or may have one or more shapes with irregular geometry. It is important to note, however, that the size and shape of each slot (2426) will be determined by the shape and relative positioning of the prongs (2428) on either side of it. Furthermore, while shown in FIGS. 24H and 24I as being oriented parallel to the cannula's longitudinal axis, slots (2426) and prongs (2428) may be angled relative to the cannula's longitudinal axis.

Additionally, a cannula tip (2424) comprising slots (2426) and prongs (2428) may aid in the delivery of one or more implants. In some instances, an implant (2430) may comprise one or more protrusions (2432) that may project through one or more slots (2426) when the implant (2430) is housed within the cannula, as shown in FIG. 24I. When the delivery device is withdrawn proximally, one or more of the protrusions (2432) may engage surrounding tissue. As the delivery device continues to be withdrawn, the implant (2430) may be held in place by this engagement and may be pulled out of the cannula. Additionally, the protrusions (2432) may be configured to help minimize damage done by protrusions (2432) to tissue when the delivery device is advanced through the body. For example, protrusions (2432) may be angled away toward the distal end of the cannula, or may have one-way flexibility that allows the protrusions (2432) to be pressed against the body of the cannula.

The prongs may or may not be substantially rigid, and may or may not be able to bend, flex, or deform in response to one or more forces or stimuli. In variations where the prongs are able to bend, flex, or deform in response to a force or stimulus, prongs may aid in the controlled release of self-expanding device. Depending on the size, shape, and configuration of the self-expanding device, in some instances the self-expanding device may have a tendency to "spring" from a cannula tip, and moveable prongs may be able to otherwise prevent this springing by allowing for controlled expansion. FIG. 24J depicts one such variation of cannula tip (2434) comprising slots (2436) and prongs (2438), with prongs (2438) bent away from cannula tip (2434). In the variation shown in FIG. 24J, prongs (2438) may be substantially rigid, but may be able to bend away from cannula tip (2434) at attachment points (2440). In other variations, one or more of the prongs (2438) may or may not be made from a fabric such as felt or another material that readily deforms.

In some instances, the expansion force provided by a self-expanding member may be sufficient to cause the prongs to bend, flex, or deform. In these variations, a device may be released from the cannula tip in any suitable fashion. In some variations, the self-expanding device may be held within the prongs, and the prongs may in turn be held by the sheath or holder. Once the sheath or holder is withdrawn relative to the prongs, the prongs may bend, flex, or deform in response to the expansion of the self-expanding device. In other variations, a self-expanding device may be advanced from the body of the cannula into the tip to cause the prongs to bend, flex, or deform.

In still other variations, the prongs may be configured to naturally bend, flex, or deform away from the cannula tip. These variations may provide particular utility where it is desirable to position the cannula tip relative to an opening such as a sinus ostium. In these variations, the prongs may be held in an unexpanded configuration by a sheath or holder, and the cannula tip may be advanced through an opening. Once through the opening, the sheath or holder may be withdrawn to release the prongs and thereby allow them to naturally bend, flex, or deform away from the cannula tip. The released prongs may resist being withdrawn through the opening, and thus may provide a user with tactile feedback that indicates to the user that the cannula tip is in contact with the opening.

In some variations where the cannula tip comprises slots and prongs, the slots may be directed inward toward the center of the cannula tip. FIG. 24K depicts one such variation of cannula tip (2442) comprising slots (2444) and inwardly directed prongs (2448). Because this configuration reduces the profile of the cannula tip (2442), the inwardly directed prongs (2448) may provide particular utility in navigating through narrow spaces or separating adjoining tissues. Additionally, cannula tip (2442) may be configured to move the inwardly directed prongs (2448) in order to allow one or more implants to be delivered from the end of cannula tip (2442). In some instances, merely advancing one or more implants through the cannula tip (2442) may provide sufficient force to separate the prongs. In other variations, the prongs (2448) may be configured to bend or flex away from their low profile configuration upon application of one or more stimuli to the cannula tip (2442). In still other variations, a balloon or other expandable member (not shown) disposed within cannula tip (2442) may be expanded to separate the prongs (2448). The balloon or other expandable member may or may not define a lumen or aperture through which one or more implants may pass. Additionally, when the prongs (2448) are separated, they may aid in positioning cannula tip (2442) relative to an opening, as described above.

Inwardly directed prongs may also be configured to puncture one or more tissues such as an ethmoid bulla. FIG. 24L shows a suitable variation of cannula tip (2450) having prongs (2452) and slots (2454). As shown in FIG. 24L, prongs (2452) may be shaped such that they approximate a point when directed inward toward the center of the cannula tip (2450). This point may or may not be sufficiently sharp to allow cannula tip (2450) to puncture tissue. Additionally, in some instances it may desirable for any tissue puncture to be substantially rounded and free of tissue fragments. As such, it may be desirable for the cannula tip (2450) to be free of any gaps from slots (2454). Thus, as shown in FIG. 24L, prongs (2452) may be configured such that slots (2454) are essentially eliminated when the prongs (2452) are directed inward. While shown in FIG. 24L as approximating a point, prongs (2452) may be joined to approximate any suitable shape that is capable of cutting or puncturing tissue. In some variations, the prongs (2452) may approximate a shape that functions as a blade.

Additionally, cannula tip (2450) may comprise one or more materials that may form a coating over and/or inside of cannula tip (2450). This coating may serve multiple functions. In some instances, the coating may cover any gaps formed between prongs (2452). In other instances, the coating may reinforce prongs (2452), allowing them to withstand greater forces applied thereto. In some variations, the coating may be dissolved or weakened when contacted by one or more liquids or gasses. In practice, the coating may be dissolved or weakened once the cannula tip (2450) has served its puncturing function, which may allow the prongs (2452) to be separated and one or more implants to be deployed through the cannula tip (2450). Examples of suitable coating materials include, but are not limited to, polyethylene glycol, one or more sugars, chitosan, polycaprolactone, or the like.

In yet other variations, the cannula tip may comprise one or more slotted tubes. FIGS. 24M and 24N illustrate one variation of cannula tip (2455) comprising slotted tube (2456) having slots (2458) and prongs (2460). Generally, a first end of the slotted tube (2456) may be fixed relative to the cannula tip (2455), while the second end may be movable relative to the first end. When the second end is moved relative to the first end, one or more prongs (2460) may bend, flex, or deform away from cannula tip (2455), as shown in FIG. 24N. In some instances, this expansion of the slotted tube (2456) may be able to dilate, temporarily or permanently, one or more tissues or openings. In other situations, an expanded slotted tube (2456) may be useful in positioning the cannula tip (2455) relative to an opening, as described above.

The shape of the expanded slotted tube (2456) may be dependent on the size, shape, and orientation of the slots (2458) and prongs (2460), as well as the manner in which the first end of the slotted tube (2456) is moved in relation to the second end. As such, slots (2458) and prongs (2460) may have any suitable size shape or orientation. Additionally, while the first and second ends of slotted tube (2456) may be moved toward or away from each other, they may alternatively be rotated in order to expand the slotted tube (2456). Indeed, FIGS. 24P and FIG. 24O illustrate one such variation of cannula tip (2462) comprising a slotted tube (2464) having angled slots (2466) and prongs (2468). In this variation, rotation of a first end of the slotted tube (2464) relative to its second end causes the angled prongs (2468) to expand away from the slotted tube (2464), as depicted in FIG. 24O.

Figure 25A:
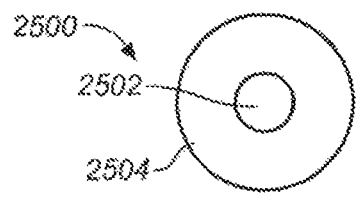
FIGS. 25A-25G show various illustrative depictions of multi-lumen cannulas.

Although generally depicted above as having one cannula defining only one lumen or aperture, the delivery devices described here may comprise any number of cannulas and each cannula may comprise any number of lumens or other apertures. Indeed, in some variations, the delivery devices described here comprise two or more cannulas. These cannulas may or may not be attached to each other. Additionally, the different cannulas may or may not have the same dimensions, may or may not be made of the same material, and may or may not have the same number of lumens or other apertures. Any number of cannulas may be steerable, and each cannula may or may not be independently steerable. Furthermore, the different cannulas may serve the same functions, or may serve different functions. For example, each cannula may be used to deliver one or more implants, carry a punch or other tissue piercing device, carry a visualization device or light source, deliver one or more drugs, liquids, gases or a combination thereof, provide suction, carry one or more steering or shaping elements as described above, carry a dilator or other tissue-expanding device, carry a guide wire, carry a tissue biopsy device or a tissue ablator, carry one or more devices for lateralizing the middle turbinate, or a combination thereof.

Where an individual cannula has more than one lumen or aperture, the lumens may have any size shape or configuration. Indeed, FIGS. 25A-25G illustrate numerous variations of suitable multi-lumen cannulas. In some variations, one or more lumens may be disposed within one or more additional lumens. For example, FIG. 25A depicts a distal end of one variation of cannula (2500) comprising a first lumen (2502) disposed within second lumen (2504). While both first (2502) an second (2504) lumen are shown in FIG. 25A to be circular, each lumen may have any suitable shape, dimensions, or configuration. Additionally, while shown in FIG. 25A to be concentrically disposed within second lumen (2504), first lumen (2502) may have any suitable location relative to second lumen (2504).

Figure 25B:
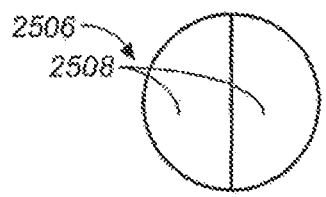
Figure 25C:
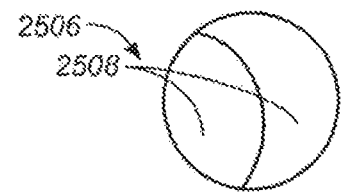
Figure 25D:
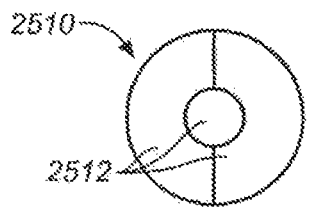
Figure 25E:
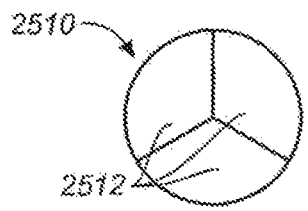
Figure 25F:
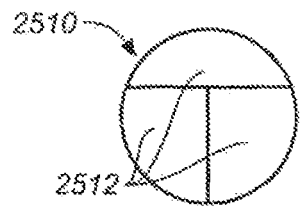
Figure 25G:
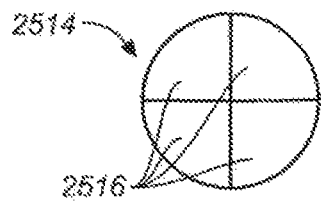

In other variations, one or more walls may divide a lumen into two or more separate lumens. FIGS. 25B-25G illustrate several variations of cannulas that are divided into multiple lumens. FIGS. 25B and 25C depict two additional variations where the cannula (2506) is divided into two lumens (2508). Similarly, FIGS. 25D-25F illustrate three variations in which the cannula (2510) is divided into three lumens (2512), and FIG. 24G depicts a variation of cannula (2514) that has been divided into four lumens (2516). Each lumen may or may not have the same size, and may or may not have the same shape. Additionally, each lumen may serve one or more functions, as described above. It is important to note that the variations of cannulas shown here are merely illustrative variations, and any suitable number of lumens having any suitable configuration and dimensions may be used without departing from the intended scope of these devices.

The delivery devices described here may have one or more additional features that may aid in the operation of the delivery device. For example, one or more cannulas of a delivery device may be configured to release one or more drugs or may comprise one or more coatings that are configured to release one or more drugs. Any suitable drug or combination of drugs as described hereinthroughout may be used. In some instances, one or more drugs having anesthetic or numbing action may provide particular utility in minimizing any pain or discomfort associated with device delivery. In other instances, one or more antibiotics, antibacterial agents, antifungal agents, antiviral agents, antiseptics or a combination thereof may or may not be useful in preventing infection that may be associated with device delivery. In still other variations, the delivery device may comprise one or more agents that may help maintain homeostasis.

In some variations, the delivery device may comprise one or more dilators attached to or otherwise engaging a cannula. For example, in some variations a balloon or other expandable member may be disposed along at least a portion of the outer surface of the cannula. Generally, at least a portion of the balloon or expandable member may be expanded away from the cannula to displace, either permanently or temporarily, one or more tissues near the cannula. The dilator may or may not surround the cannula, and may or may not be expanded to displace tissue in multiple directions. Additionally, the dilator may be detachable from the cannula. This may provide particular utility when it is desirable to keep a certain pathway open for the duration of the procedure. For example, in some instances, the middle turbinate in the sinus anatomy may press against the lateral nasal wall. In order to deliver a device into the ethmoid sinuses, it may be useful to move the middle turbinate away from the lateral nasal wall. Thus, once a cannula has passed between the middle turbinate and the lateral nasal wall, a dilator may be expanded to further move the middle turbinate away from the nasal wall. Once expanded, the dilator may be disengaged from the cannula. The dilator may maintain the passage between the middle turbinate and the nasal wall, thereby allowing an operator to remove the delivery device from the nasal passages and reinsert the delivery device without needing to move the middle turbinate each time. The dilator may or may not be configured to degrade inside the body, and may or may not be removed following delivery of the one or more implants.

Similarly, the delivery device may comprise one or more implants that may be disposed along or otherwise engage an outer surface of a cannula. In some instances, the implant may be an expandable device. In some of these variations, the implant may be a self-expanding device, such as those described above. In others of these variations, the implant may be expandable as a result of external force applied to the implant. Additionally, the implant may be disposed along or attached to the cannula in any suitable manner. In some variations, a sheath or holder may hold the implant in place against the cannula. In other variations, one or more coatings may hold the implant in place. In variations where the implant is balloon expandable, the implant may be releasably bonded to a balloon. Generally speaking, the implant may be released from the cannula to provide support to one or more tissues. In some variations, the implant may temporarily or permanently dilate one or more tissues, as described just above. The implants may or may not be biodegradable, may or may not be configured to deliver one or more drugs, and may or may not be removed from the body following the delivery of the one or more implants.

Additionally, any of the delivery devices described here may comprise one or more sheaths that may be attached to or otherwise engage one or more cannulas. These sheaths may be made of any suitable material or combination of materials, and may or may not include any of the cannula tips or features as described above. For example, the cannula may comprise a funnel-shaped tip, an olive tip, a wedge tip, a slotted tip, a leaf tip, a slotted tube, one or more markers, one or more dilators, one or more stents, or a combination thereof. The one or more sheaths may be attached to or may engage one or more cannulas in any suitable manner. For example, in some variations the one or more sheaths may be disposed along an exterior surface of a cannula. In other variations, the sheath may be disposed inside of one or more cannula lumens.

Figure 26B:
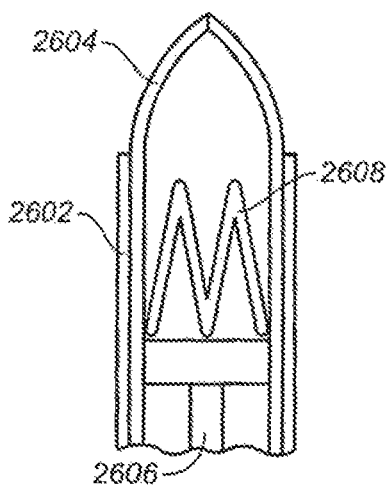
FIGS. 26A and 26B are a side view and a cross-sectional view, respectively, of the distal end of one variation of a delivery device comprising a pusher, a cannula, and a sheath.
Figure 26A:
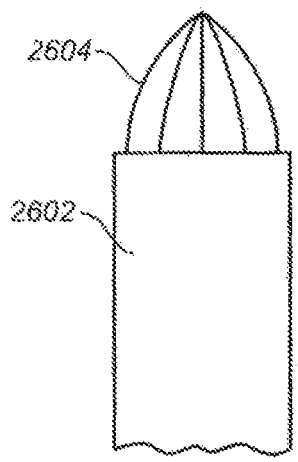

FIGS. 26A and 26B illustrate a side view and a cross-sectional side view respectively of the distal end of one variation of delivery device (2600) comprising a cannula (2602), sheath (2604), and pusher (2606), and which is housing an implant (2608) therein. As shown in FIG. 26, sheath (2604) is configured to have prongs forming a tissue-piercing tip, as described above. In practice, cannula (2602) may be advanced throughout a portion of the anatomy to a delivery location, and sheath (2604) may penetrate tissue as necessary in advancing delivery device (2600). Once cannula (2602) is in place at the delivery location, sheath (2604) may be withdrawn proximally relative to cannula (2602), and the prongs may open to allow the implant (2608) to pass through the distal end of sheath (2604). The opening of the prongs may or may not be caused by engagement between the sheath (2604) and the pusher (2606). Note that although sheath (2604) is shown in FIG. 26 to reside between cannula (2602) and pusher (2606), sheath (2604) may instead be disposed around the outside of cannula (2602).

In some variations, the delivery device may be configured to release the sheath. In some of these variations, the sheath may be released inside of the body. In some instances, the sheath may be configured to be held in one or more portions of the body. For example, in variations where the sheath comprises a slotted tip, the prongs of the slotted tip may be expanded inside of the body. Once expanded, the prongs may resist movement through an opening such as a sinus ostium, and the sheath may be held substantially in place. The sheath may or may not be configured to degrade, and may or may not be configured to release one or more drugs. Additionally, in some instances the sheath may be used as a tube through which one or more liquids or gases may be passed into the body.

Pusher

Figure 27:
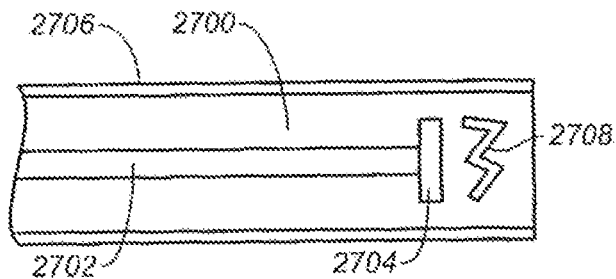
FIGS. 27 and 28A-28B depict illustrative variations of delivery devices comprising pushers.

In variations of the delivery devices described here that comprise a pusher, such as those shown in FIGS. 5A and 5B, the pusher may have any suitable size, shape, and configuration. Additionally, the delivery device may comprise any number of pushers. Each cannula or cannula lumen may comprise one or more pushers slidably disposed therein. Additionally, each pusher may or may not comprise one or more lumens therethrough, and may or may allow a liquid or gas to pass therethrough. FIG. 27 shows one variation of pusher (2700) comprising body (2702) and head (2704), and disposed within cannula (2706). Generally, pusher (2700) may be advanced relative to cannula (2706), and head (2704) may engage one or more implants (2708) to push the one or more implants (2708) out of the distal end of the cannula (2706). Body (2702) and head (2704) may or may not be made of the same material, and may or may not have the same width. In some instances, it may be desirable to maintain a certain ratio between the diameter of the cannula (c) and the diameter of the pusher (p). For example, the ratio of the diameter of the cannula to that of the pusher, or c:p, may be about 10:1, about 9:1, about 8:1, about 7:1, about 6:1, about 5:1, about 4:1, about 3:1, about 2:1, and the like. Indeed, certain ratios may allow delivery device to have a substantially rigid pusher body (2702) and a curved cannula (2706) without the pusher body (2702) substantially affecting the shape of the cannula (2706).

Figure 28A:
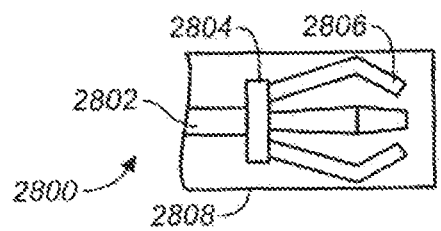
Figure 28B:
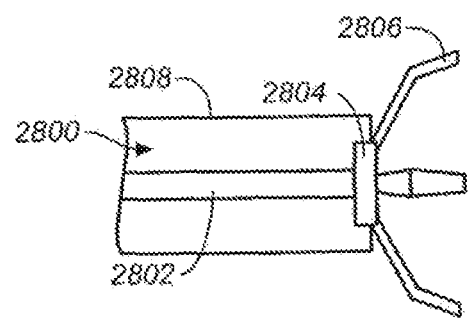

In some variations, the pusher may comprise one or more features that may aid in loading one or more implants into a cannula. FIGS. 28A and 28B illustrate one such variation of pusher (2800) comprising body (2802) and head (2804) including runners (2806). Generally, head (2804) and runners (2806) may fit within cannula (2808), as shown in FIG. 28A. When pusher (2800) is advanced and runners (2806) exit cannula (2808), the runners (2806) may or may not bend, flex, or rotate away from each other, as shown in FIG. 28B. To help load an implant into the cannula (2808), pusher (2800) may first be advanced such that runners (2806) exit cannula (2808), the implant may be positioned inside the aperture defined by runners (2806), and the pusher (2800) may be withdrawn into the cannula (2808). As the runners are pulled back into the cannula (2808), the cannula (2808) may cause the runners (2806) to return to their original positions, and may thereby grasp or grab the implant. As the pusher (2800) continues to be proximally withdrawn, the runners (2806) may pull the implant inside of cannula (2808).

Figure 29A:
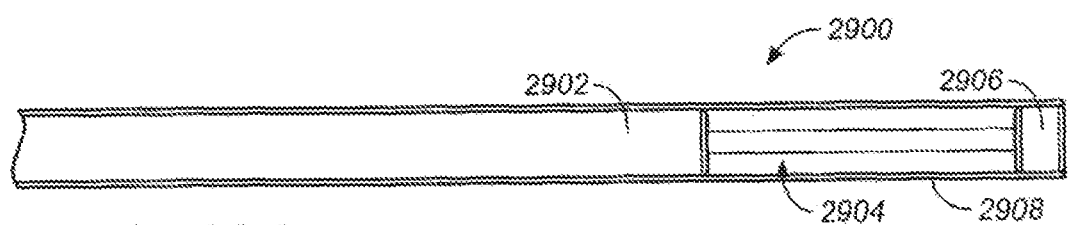
FIGS. 29A and 29B show one variation of a delivery device comprising a stopper.
Figure 29B:
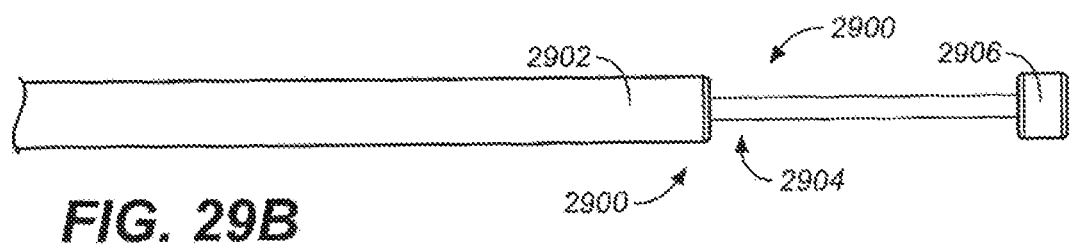

While described above as comprising a pusher, the delivery devices described here need not have a pusher. Indeed any suitable actuation mechanism may be used. For example, delivery may be actuated by the introduction of one or more gasses or liquids to the cannula (e.g. pressurized air, inert gases, water, saline, or the like). In other variations, a stopper may be used to help release one or more implants. FIGS. 29A and 29B illustrate one variation of delivery device (2900) comprising stopper (2902). Shown in FIG. 29A is stopper (2902) comprising holding segment (2904) and head (2906), and disposed within cannula (2908). Generally, one or more implants (not shown) are housed within cannula (2908) in the holding segment (2904) or stopper (2902), and head (2906) prevents the one or more implants from being prematurely released from the cannula (2908). Indeed, to release the one or more implants, cannula (2908) may be withdrawn relative to stopper (2902) or stopper (2902) may be advanced relative to cannula (2908) to expose holding segment (2904) and the one or more implants, as shown in FIG. 29B.

While shown in FIGS. 29A and 29B as having a narrower diameter than the rest of stopper (2902), holding segment (2904) may have any suitable size, shape or configuration. Indeed, in some variations holding segment (2904) may comprise one or more channels passing at least partially through the stopper (2902). Additionally, the one or more implants may or may not be releasably attached to the stopper (2902).

Generally, delivery devices comprising a stopper may provide the user greater leeway in controlling the placement of the one or more implants. Indeed, in variations where an implant is pushed out the distal end of a device, it may be difficult to ensure proper placement relative to one or more structures. In variations with a stopper, the distal end of the delivery device may be placed in approximation with one or more tissue structures. By withdrawing the cannula relative to the stopper, the holding structure may be exposed to release the one or more implants. This may provide utility in allowing a user to place an implant in proximity with one or more tissue structures.

Figure 30A:
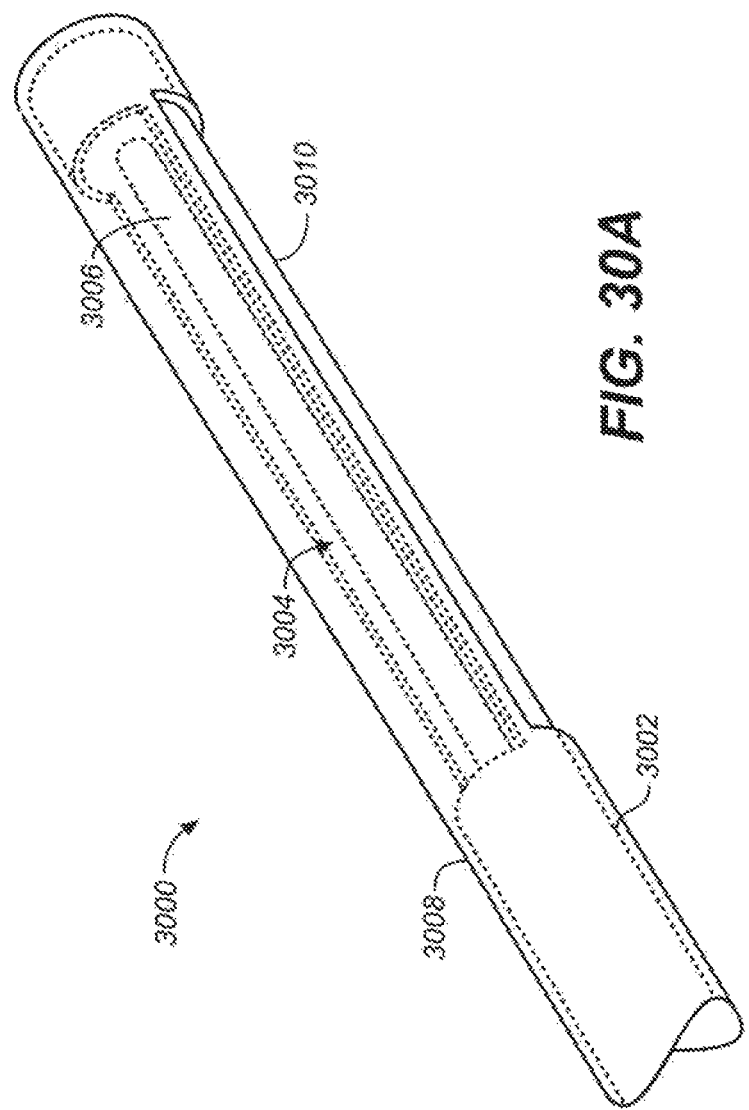
FIG. 30A is a perspective view of a variation of a delivery device comprising a stopper and a cannula.

FIGS. 30A-30F show another variation of delivery device (3000) comprising a stopper (3002). FIG. 30A depicts a perspective view of delivery device (3000). Also shown there is stopper (3002) comprising holding portion (3004) and restraining member (3006), and cannula (3008) comprising cannula aperture (3010). FIG. 30B shows a side view of stopper (3002), and FIG. 30C shows a side view of cannula (3008). Generally, stopper (3002) is configured to house one or more implants in holding portion (3004), which defines stopper aperture (3012), and may release the one or more implants therethrough. Additionally, restraining member (3006) may or may not be slidably disposed within stopper (3002), and may or may not be able to releasably connect one or more implants to stopper (3002). For example, in variations where delivery device (3000) is used to deliver an implant that defines a lumen or aperture, restraining member (3006) may be passed through this lumen or aperture, thereby preventing the implant from being disengaged from the delivery device (3002). It is important to note that while shown in FIGS. 30A-30F as having a restraining member (3006), stopper (3002) need not.

In practice, one or more implants may be placed in holding portion (3004), and stopper (3002) may be placed within cannula (3008). Stopper (3002) may or may not be configured to rotate within cannula (3008). In variations where stopper (3002) is able to rotate within cannula (3008), rotation of the stopper (3002) or cannula (3008) may be used to release the one or more implants. When the stopper (3002) is placed within cannula (3008), the delivery device may have an open configuration and a closed configuration, depending on whether cannula (3010) and stopper (3012) apertures are aligned. When the apertures are not aligned, delivery device (3000) is "closed" as the stopper aperture (3012) is covered by the body of cannula (3008), as shown in a top view in FIG. 30D. To open the device, a user may rotate the cannula (3008) or stopper (3002) to align the apertures. At this point, one or more implants may be released from the delivery device (3000) through the apertures.

In variations that include a restraining member (3006), however, the release of the one or more implants may require an additional step. Assuming that the restraining member (3006) has been configured to releasably attach the implant to the delivery device (3000), the restraining member (3006) may need to be withdrawn, as shown in a top view in FIG. 30F, before the implant may be released. A restraining member (3006) may provide a user with additional control in properly placing a self-expanding device (not shown), such as those described above. When a delivery device (3000) holding a self-expanding device is moved from a closed to an open configuration, the self-expanding device may have a tendency to expand through the cannula aperture (3010), but is still at least partially attached to the delivery device (3000) by restraining member (3006). Were it not for this attachment, the self-expanding device may be completely released from the device, thereby making it difficult to reposition the self-expanding device once it has already been expanded. Instead, the attachment may allow a user to reposition the expanded self-expanding device as necessary. Once the self-expanding device has been properly placed, a user may retract the restraining member (3006) to release the self-expanding device.

While shown in FIG. 30C as having cannula aperture (3010), cannula (3008) need not. Indeed, in some variations the same effect may be achieved by withdrawing cannula (3008) relative to stopper (3002) or by advancing stopper (3002) relative to cannula (3008). In these variations, as cannula (3008) is withdrawn or stopper (3002) is advanced such that stopper aperture (3012) is exposed, the delivery device (3000) may release one or more implants. As mentioned above, the restraining member (3006) may limit or control the release of the one or more implants.

Figure 31A:
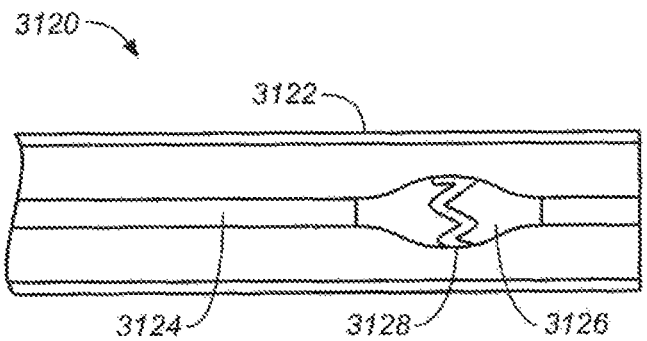
FIGS. 31A-31C and 32A-32B provide illustrative examples of the distal ends of various delivery devices described here.
Figure 31B:
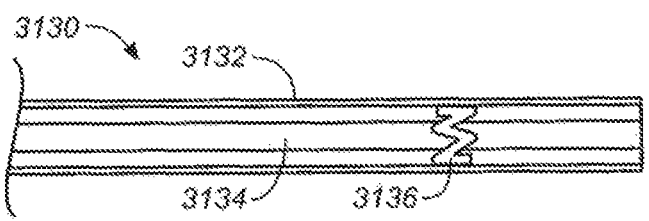
Figure 31C:
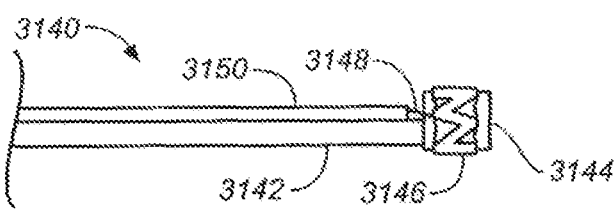

FIGS. 31A-31C depict cross-sections of additional illustrative distal portions of delivery device configurations. FIG. 31A provides a cross-sectional representation of one variation of the distal end of suitable delivery device (3120). Shown in this variation is cannula (3122), guide wire or guide element (3124), and expandable balloon (3126). In this variation, device (3128) is placed in its compressed configuration around expandable balloon (3126). Once the delivery device has been advanced to the desirable target location, the cannula (3122) may be withdrawn proximally, or the guide wire (3124) may be advanced distally, to expose the balloon (3126) and device (3128) to the target tissue. The balloon may then be expanded to help the device better appose the target tissue. In some variations, the balloon may be heated to aid in device expansion or deformation. Once device (3128) has been deployed, expandable balloon (3126) may be deflated and delivery device (3120) may be withdrawn, leaving the expanded device (3128) at the target location.

Of course, while shown in FIG. 31A as an expandable balloon (3126), it should be understood that any expandable structure may be used. The expandable structure may be made from any suitable material, such as, for example, latex, polyamide, nylon, polyethylene, low-density polyethylene, Duralyn®, Duramax®, Pebax®, polyurethane, and any analogs, homologues, congeners, derivatives, salts, copolymers, and mixtures thereof.

FIG. 31B shows another variation of the distal end of delivery device (3130). This variation is similar to the variation described just above with reference to FIG. 31A, except that no balloon is used. Shown in this variation, is cannula (3132), guide wire or guide element (3134), and device (3136) disposed about guide wire (3134). In use, once the delivery device is advanced to or adjacent to the target location, the cannula (3132) may be proximally withdrawn, or the guide wire (3134) may be advanced distally to position device (3136) at the desired location. The guide wire (3134) may then be withdrawn, leaving device (3136) to self-expand.

FIG. 31C depicts yet another variation of the distal end of a delivery device (3140). In this variation the delivery device (3140) comprises a guide wire (3142) having a distal tip (3144), around which device (3146) is disposed. The device (3146) is releasably attached to a suture (3148) or other similar such material, the ends of which, are run through a suture sheath (3150). In this variation, the delivery device (3140) may be advanced to a target location and suture (3148) withdrawn proximally through the suture sheath (3150), thus releasing the device (3146) and allowing it to self-expand. It should be understood that the above described variations, are but a few of the many possible variations that may be suitable for the delivery devices described here.

Figure 32A:
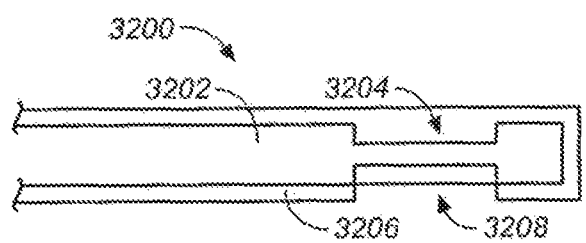
Figure 32B:
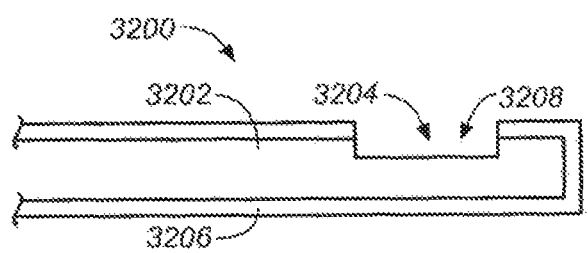

FIGS. 32A and 32B illustrate still another variation of delivery device (3200) comprising cannula (3202) having cannula aperture (3204) and sheath (3206) comprising sheath aperture (3208). While shown in FIG. 32A as being disposed on cannula (3202), sheath (3206) may be located within cannula (3202), and may be configured in any way with any feature or combination of features as described above. Cannula (3202) and sheath (3206) may or may not be able to rotate relative to one another, or may or may not be able to slide relative to one another. The delivery device (3200) may have an open configuration and a closed configuration. In the closed configuration, the cannula aperture (3204) is covered by a portion of the sheath (3206), and the sheath aperture (3208) is blocked by a portion of the cannula (3202), as shown in a side view in FIG. 32A. To release one or more implants from delivery device (3200), cannula (3202) and sheath (3206) may be moved, whether through rotation or sliding actuation, such that at least a portion of cannula aperture (3204) and sheath aperture (3204) overlap, as shown in a side view in FIG. 32B. When the cannula (3204) and sheath (3208) apertures overlap, a device may pass through the apertures to exit delivery device (3200).

Handle

The delivery device's handle may have any suitable dimensions or configuration of elements, and may include any suitable manner of actuating the device. Indeed, each handle may have any suitable number of buttons, knobs, triggers, cranks, levers or other actuating components for actuating one or more of the features of the delivery devices, as described above. Each actuating component may control one or more feature of the device, or may control multiple features simultaneously. For example, in variations where the device comprises two control lines for steering a cannula, each control line may be controlled by a separate actuating component, or both may be controlled by the same actuating component. For example, the handle may comprise a knob that affects the amount of tension placed on each control line. When the knob is rotated in one direction, the tension may be increased in a first line and decreased in second line, and vice versa when the knob is rotated in the other direction.

Figure 33:
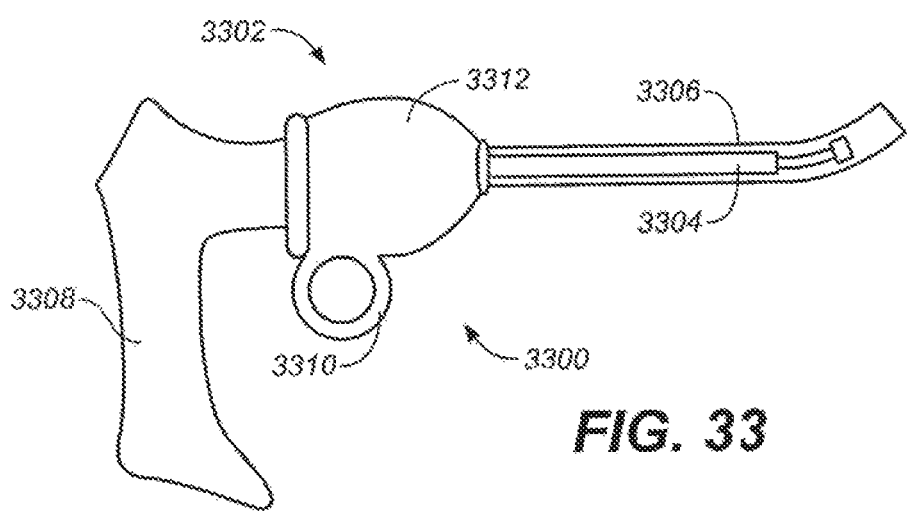
FIG. 33 depicts an illustrative example of a delivery device described here.

In variations where the handle comprises a pusher or a stopper as described above, the handle may be configured to actuate the pusher or stopper in any suitable manner. In some variations, the handle may be configured to advance a pusher or stopper relative to the cannula. For example, in the variation shown in FIG. 5B above, handle body (516) is attached to cannula (514), while plunger (520) is attached to pusher (522). Thus, when the plunger (520) is pushed relative to handle body (516), pusher (522) is advanced relative to cannula (514). In other variations, the handle may be configured to retract a cannula relative to a pusher or stopper. FIG. 33 shows a variation of delivery device (3300) comprising handle (3302), stopper (3304) and cannula (3306). As shown in FIG. 33, handle (3304) comprises grip (3308) and trigger (3310) attached to body (3312). In this variation, cannula (3306) may be connected, permanently or releasably, to body (3312), and stopper (3304) may be attached to grip (3308). To release an implant from delivery device (3300), an operator may hold grip (3308) and pull trigger (3310) proximally relative to grip (3308). As the trigger (3310) moves proximally, cannula (3306) moves proximally, thereby withdrawing cannula (3306) relative to stopper (3304).

Figure 34A:
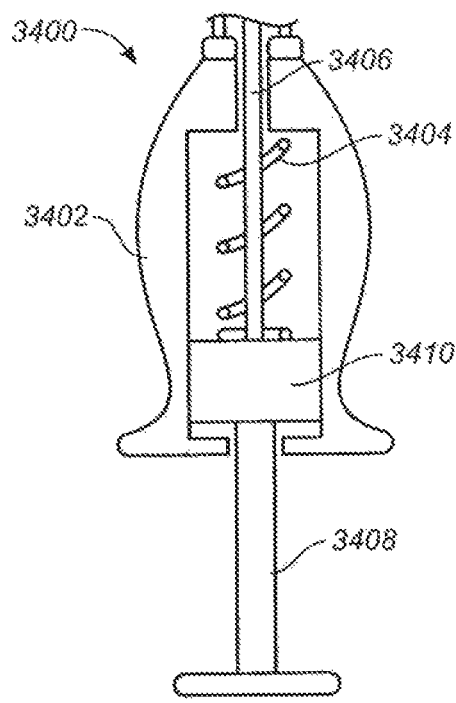
FIG. 34A is a cross-sectional side view of a handle for use with the delivery devices described here.
Figure 34B:
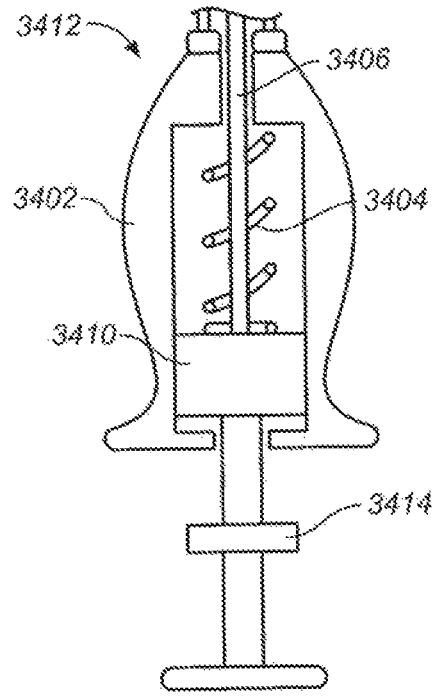
FIGS. 34B-34D are illustrative examples of adjustable handles suitable for use with the delivery devices described here.
Figure 34C:
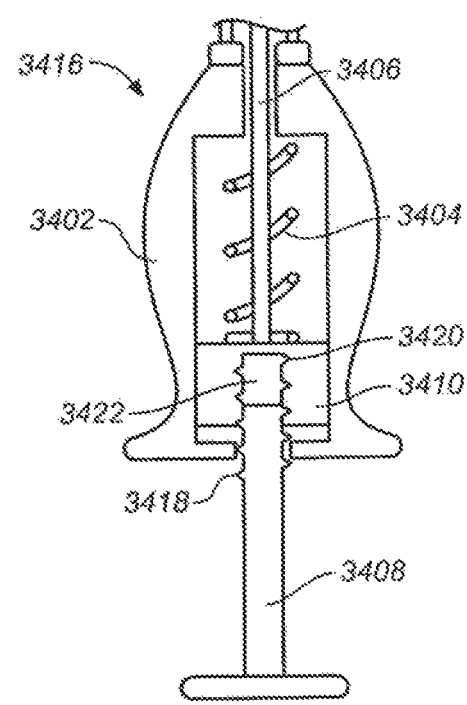
Figure 34D:
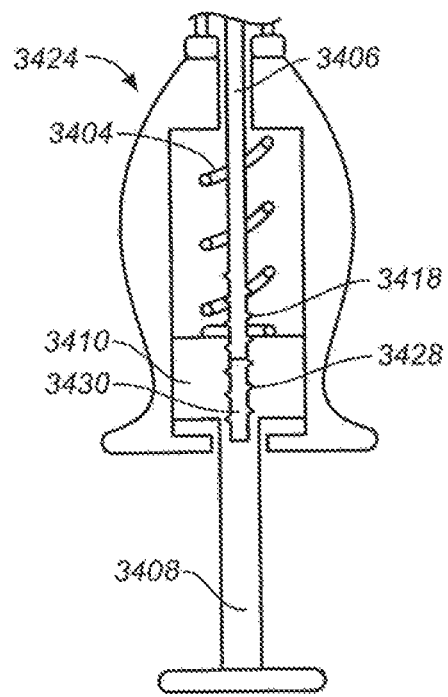

In variations that include a pusher or a stopper, the handle may be adjustable to control the amount of movement of the pusher, stopper, or cannula when a trigger is activated. FIG. 34A shows a cross sectional view of one variation of handle (3400), while FIGS. 34B-34D illustrate suitable variations of adjustable handles. Shown in FIG. 34A is handle (3400) comprising handle body (3402), spring (3404), pusher (3406), plunger (3408) and connector (3410). Generally, handle body (3402) houses spring (3404) and connector (3410), such that spring (3404) biases connector (3410) away from the proximal end of the handle body (3402). Additionally, connector (3410) may connect plunger (3408) and pusher (3406). To activate the device, a user may depress plunger (3408), advancing pusher (3406) and compressing spring (3404). When the plunger (3408) is no longer being depressed, spring (3404) may press against connector (3410) to return the handle to its pre-activation configuration.

FIG. 34B illustrates one variation of handle (3412) comprising an adjustable ring (3414). The remaining components of handle (3412) are otherwise the same as shown in FIG. 34B and are labeled as such. Adjustable ring (3414) may be releasably attached to a portion of plunger (3408), and may limit the amount that plunger (3408) may be depressed. This may find particular utility when cannulas of different lengths are used with the same handle (3412). For each cannula, an operator may adjust the adjustable ring (3414) to provide the proper ranger of movement for plunger (3408) and pusher (3406).

FIGS. 34C and 34D illustrate variations of adjustable handles in which one or more components may have threading. FIG. 34C illustrates a variation of delivery device (3416) in which trigger (3408) has threading (3418) that corresponds to tracks (3420) within a hollow portion (3422) of connector (3410). To adjust the length of trigger (3408) and thereby the amount that trigger (3408) may be depressed, trigger (3408) may be rotated to screw a portion of trigger (3408) into the hollow portion (3422) of connector (3410). Similarly, 34D illustrates a variation of delivery device (3424) in which pusher (3406) comprises threading (3426) that may be screwed into tracks (3428) in hollow portion (3430) of connector (3410). This may adjust the relative length of pusher (3406).

II. Methods of Use

Both the self-expanding devices and the delivery devices described here may be useful in a variety of locations within the body, for a number of different purposes. For example, the self-expanding devices may help provide support to or dilate tissue, or may be useful in treating various conditions or diseases. The self-expanding devices may indeed be used in any area of the body that may benefit from their structural and functional features.

For example, the devices may be delivered to one or more tonsils, sinus cavities, arteries, veins, one or more openings or cavities, e.g., the middle ear or tympanic cavity, hollow-body organs such as the ureter, fallopian tubes, biliary ducts;

pulmonary organs such as tracheas, bronchi and bronchioles; and gastrointestinal organs such as the esophagus, stomach, intestines, and colon, and the like. In the case of sinuses, the devices may be used before or after surgery. In some variations, the devices described here are used in the sinus cavities of pediatric patients. This may be particularly advantageous compared to traditional treatment options for pediatric patients in that in using the described devices and methods the risk of poor patient compliance is reduced.

The devices can further be used to treat and/or ameliorate one or more symptoms of a variety of diseases that include, but are not limited to, urinary incontinence, atherosclerosis, benign prostatic hypertrophy, recoiling lesions after percutaneous transluminal angioplasty and in dissections, chronic occlusions, anastamotic hyperplasia in vein grafts and synthetic vascular grafts, vulnerable plaque, aneurysms of the aorta and large arteries, arteriovenous fistulae and traumatic leaks, malignant stenosis of the gastrointestinal tract, acute ileus in colorectal cancer, biliary closure from cholangiocarcinoma or other hepatic cancers, benign compression of the trachea and malignant tracheobronchial obstructions, one or more diseases or conditions of the sinuses, and the like.

The devices may be delivered and deployed in any suitable manner. In some variations, the devices are deployed in an open surgical fashion. In other variations, the devices are deployed in a less invasive fashion (for example, laproscopically, endoscopically, or intravascularly through the use of catheters). In instances where the devices are delivered in a generally minimally invasive fashion, the devices are delivered in their compressed configurations. The devices may be preloaded in a delivery device, but need not be. For example, in instances where the device has a limited ability to fully expand after remaining in its compressed state for extended periods of time (i.e., relaxation of the device may occur over time, resulting in a loss of shape memory, for example), it may be more desirable to crimp and load the device into a delivery device just prior to delivery and deployment. The device may be crimped straight into a delivery device.

Figure 4A:
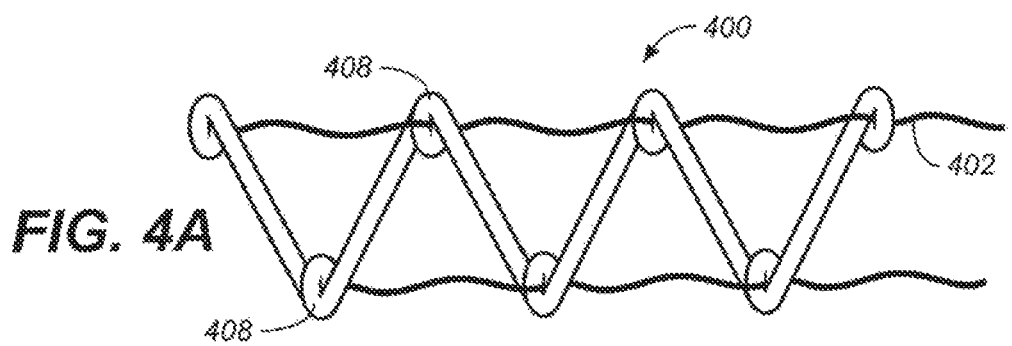
FIGS. 4A and 4B depict one variation of how the devices described herein may be compressed, using a suture of other suitable material that passes through an eyelet of a loop, or other opening of the device.
Figure 4B:
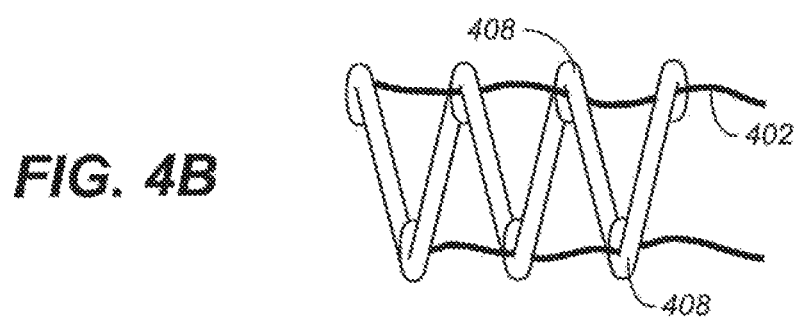
Figure 4C:
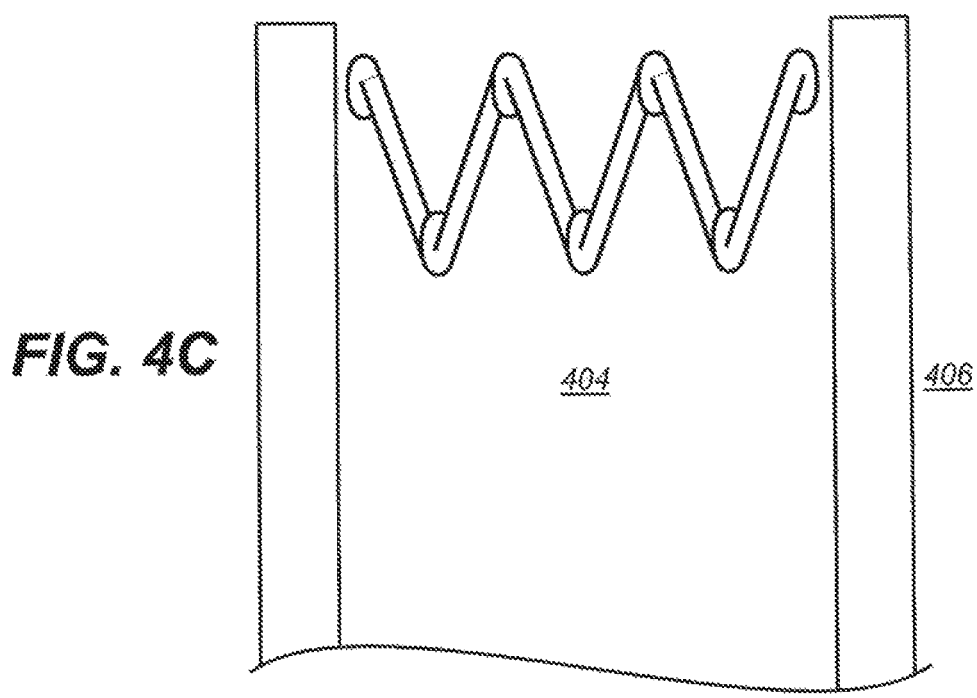
FIG. 4C demonstrates how the device may be loaded into a delivery device.

While additional methods of crimping the devices described here will be discussed in detail below with specific reference to the methods of manufacture, FIGS. 4A-4C illustrate one possible method by which device (400) may be reduced into its compressed configuration using a suture (402), fiber, or other similar material, and then placed in a lumen (404) of a delivery device (406). In variations of a device (400) having multiple loops (408), the suture (402) may be threaded through all or some of the loops, and may be threaded through the loops one or more times while the device (400) is in its expanded configuration. Once the suture (402) is threaded through a desirable number of loops, the ends of the suture (402) may be pulled to reduce device (400) into its compressed configuration, as shown in FIG. 4B. In some variations, the ends of the suture (402) are pulled in the same direction, and in other variations, they are pulled in opposite directions. In still other variations, the ends of the suture may be pulled at different angles. As depicted in FIG. 4C, the suture (402) may then be removed and discarded, and the compressed device (400) may be loaded into the lumen (404) of a delivery device (406) via its distal end (or proximal end as the case may be). The suture may be removed before or after the device is loaded within the lumen, and as described above, the suture (402) may also be left threaded through the loops (408), in the event retrieval or withdrawal of the device is desirable.

Other methods may also be used to reduce the device (400) to its compressed configuration. For example, the device may be manually compressed using one's fingers, or placed within a cylindrical device that is capable of reducing its diameter. The device may even be manufactured in its compressed configuration, and then later be manually or thermally expanded or deformed into its expanded configuration.

In another method, the device may be placed on a tapered mandrel, and slid down the mandrel, reducing the diameter of the device. An outer sheath or funnel may be placed over the tapered mandrel in order to control the outer diameter of the device. The end of the tapered mandrel may then be placed within a delivery device, and the outer sheath/funnel may be removed, thereby leaving the device in its compressed configuration within the delivery device.

In yet another method, the device may be placed in the opening of a funnel. A fiber attached to the device may be withdrawn through the funnel, pulling the device and crimping it as its diameter is reduced. Similarly, a balloon may be placed within the funnel, at least partially expanded, and pulled through the funnel to crimp the device. Such a balloon may provide for uniform crimping due to the friction force between the device and balloon.

In still other methods, a roll crimper is used to reduce the device to its compressed configuration. In these methods, the device is first slid loosely onto the balloon portion of a guide wire. This assembly is placed between the plates of the roll crimper. With an automated roll crimper, the plates come together and apply a specified amount of force. The plates move back and forth a set distance in a direction that is perpendicular to the guide wire. The guide wire rolls back and forth under this motion, and the diameter of the device is reduced. The process can be broken down into more than one step, each with its own level of force, translational distance, and number of cycles.

Still other methods utilize a sliding wedge or iris crimper to reduce the device to its reduced configuration. In the sliding wedge or iris crimper, adjacent pie-piece-shaped sections move inward and twist, much like the leaves in a camera aperture. This crimper can be engineered to have two different types of endpoints. It can stop at a final diameter, or it can apply a fixed force and allow the final diameter to float. The sliding wedge crimper presents a nearly cylindrical inner surface to the device, even as it crimps. This means the crimping loads are distributed over the entire outer surface of the device. Additionally, the self-expanding devices may be crimped using any of the methods or devices described in U.S. Provisional Application Ser. No. 61/085, 795, titled "Methods and Devices for Crimping Self-Expanding Devices," which is hereby incorporated by reference in its entirety.

Any of the delivery devices described above may be used to deploy the self-expanding devices described here, as well as any other suitable implant or implants. Generally, the distal end of a delivery device is introduced into the body. In some variations, the distal end of the delivery device may be introduced into a natural opening in the body, such as an ear canal or a nostril. In other variations, the distal end of the delivery device may be introduced into an artificially-created opening in the body. In some of these variations, the artificially-created opening may be preformed using one or more tools that are separate from the delivery device. In variations where the delivery device has a cannula or sheath configured to puncture tissue or otherwise carries one or more tissue-piercing devices, the delivery device may be used to create the opening.

Once the delivery device has gained access to the body, at least a portion of the delivery device, which may be a portion of one or more cannulas, may then be advanced to a target location. In some variations, this advancement occurs under direct visualization. The direct visualization may be achieved by a device external to the delivery device, such as an endoscope, or may be achieved by one or more visualization devices disposed in one or more lumens of a cannula or by one or more visualization devices attached to the delivery device. In other variations, the advancement occurs under indirect visualization, such as fluoroscopy or ultrasound.

During advancement, it may be desirable to provide an anesthetic or other numbing drug to help minimize pain associated with the procedure. In some variations, the delivery device may spray or eject one or more fluids or gases that comprise one or more drugs. In other variations, a portion of the delivery device, such as a cannula, may release one or more drugs, or may comprise a coating that releases one or more drugs.

Additionally, during advancement of the delivery device it may be necessary to displace, either temporarily or permanently, one or more tissues. In some variations, one or more cannulas or sheathes of the delivery device may comprise a tip, as described above, that may be used to displace one or more tissues. Additionally, one or more dilators or additional implants may be used to either temporarily or permanently dilate one or more tissues, and may be used to maintain an open passageway between the body opening and the target location. In still other variations, one or more dilators separate from the delivery device may be used to either temporarily or permanently dilate or otherwise displace one or more tissues. The one or more dilators may displace tissue before advancement of the delivery device, or may displace tissue simultaneously with advancement of the delivery device. Additionally, the one or more dilators may or may not sequentially dilate the tissue (e.g. by introducing dilators of increasing size, or sequentially increasing the size of the dilator).

Once the delivery device has reached the target location, the tip of a cannula or sheath may be positioned relative to one or more tissues or tissue openings. Once the tip is properly positioned, the delivery device may release or otherwise eject the one or more self-expanding devices or other implants. In some variations, the released device or devices may be repositioned as necessary.

In some variations, the devices are sized and shaped to be delivered within one or more sinus cavities, or one or more locations where a sinus cavity has been removed. Any of the devices and methods described here may also be used to treat one or more locations of the osteomeatal complex as described in U.S. patent application Ser. No. 11/775,157 filed on Jul. 9, 2007, which is hereby incorporated by reference in its entirety. FIG. 6 shows a simplified depiction of the anatomy of the sinuses following a typical sinus surgery. Shown there is maxillary sinus (600) having a surgically-enlarged maxillary sinus opening (602), surgically enlarged ethmoid sinus (604), and nasal cavity (606). It should be understood that while the methods described just below will be in reference to device delivery and deployment to one or more sinus cavities following a typical sinus surgery, any of the devices described herein may also be delivered to one or more sinus cavities prior to a typical sinus surgery.

Deploying one or more of the devices described here to one or more of the sinus cavities may help maintain the patency of the sinus cavities, help prevent obstruction caused by adhesions between healing or inflamed mucosal surfaces, and help deliver an effective localized dose of a drug. When placed in the ethmoid sinus following sinus surgery, a device may help prevent lateralization of the middle turbinate, which could otherwise lead to formation of adhesions that may block the sinus opening. In addition, the devices described here may aid in the natural healing process when they are configured to deliver one or more drugs to one or more sinus cavities after a sinus surgery. In addition, when a device that defines a lumen (having any suitable cross-sectional geometry) in its expanding configuration is used (e.g., the device shown in FIG. 1A), the device may offer the additional benefit of providing better access to the surgical site for post surgical clean-up and follow-up. That is, as opposed to traditional packing materials, a device defining a lumen allows for more natural clearance of mucus and sinus drainage, and allows for easier irrigation and removal of other debris.

FIGS. 7A-7C illustrate a method of delivering a device (704) to an ethmoid sinus (700) using a delivery device (702). With reference now to FIG. 7A, the delivery device (702) is first advanced through nasal cavity (706) (e.g., under endoscopic guidance), and into ethmoid sinus (700). Once the delivery device (702) reaches the desirable location within the ethmoid sinus (700), as shown in FIG. 7B, the device (704) may be deployed. Once the device (704) is fully deployed (i.e., it changes into its expanded configuration), as depicted in FIG. 7C, the delivery device (702) may then be removed from the body. Although depicted in FIGS. 7A-7C as a delivery cannula or other introducer device with a push rod (not shown), the delivery device (702) may be any device suitable to deploy a device (704), as described above.

Figure 8A:
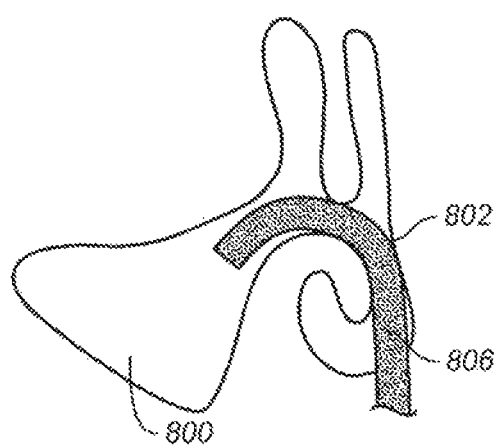
FIGS. 8A-8C depict an illustrative method of delivering a device to a maxillary sinus cavity.
Figure 8B:
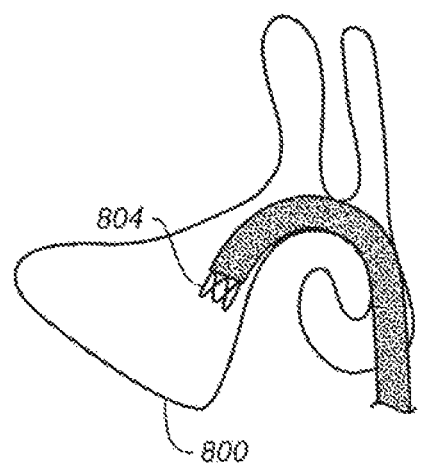
Figure 8C:
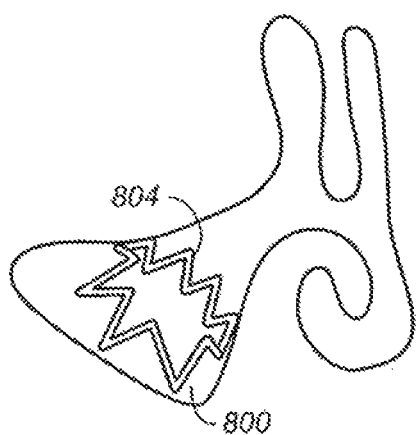

FIGS. 8A-8C illustrate a method of delivering device (804) to a maxillary sinus (800) using a delivery device (802). With reference now to FIG. 8A, the delivery device (802) is first advanced through nasal cavity (806) (e.g., under endoscopic guidance), and into maxillary sinus (800). Once the delivery device (802) reaches the desired location with the maxillary sinus (800), as shown in FIG. 8B, the device (804) may be deployed. Once the device (804) is fully deployed (i.e., it changes into its expanded configuration), as depicted in FIG. 8C, the delivery device (802) may then be removed from the body. Although depicted in FIGS. 8A-8C as a delivery cannula or other introducer device with a push rod (not shown), the delivery device (802) may be any device suitable to deploy a device (804), as described above.

As described above, the devices may be repositioned during or after delivery, if desirable. Similarly, the devices may be removed (either by a suture or other similar such material, by gripping the device with forceps or the like, or via suction or aspiration, etc.).

While shown in FIGS. 7A-7C and 8A-8C as being delivered to the ethmoid and maxillary sinuses, respectively, it should be clear that the devices may be delivered to any of the sinus cavities. For example, the devices may be delivered to a frontal sinus or a sphenoid sinus. Similarly, the devices may be delivered into the nasal passage or the ostium of any sinus cavity. The devices may be deployed anywhere, and may or may not be configured to deliver a drug.

Figure 9A:
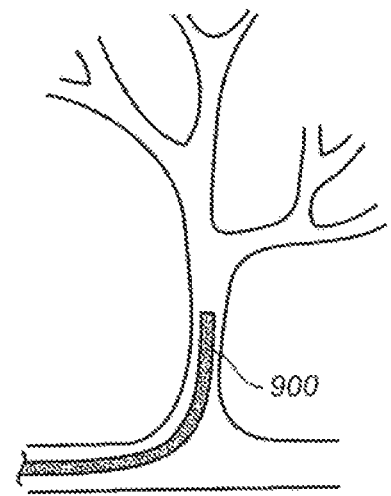
FIGS. 9A-9C depict an illustrative method of delivering a device to the vasculature.
Figure 9B:
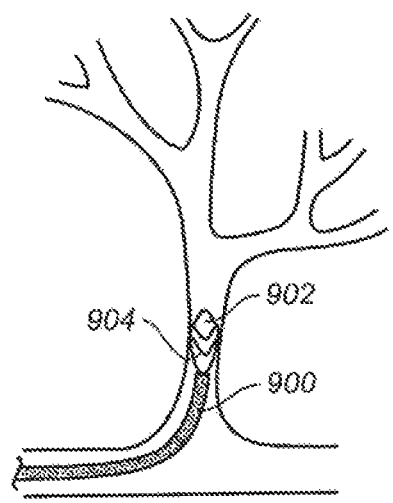
Figure 9C:
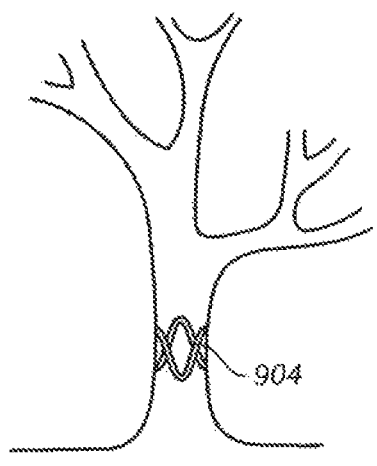

FIGS. 9A-9C depict a method of delivering a device (904) within one or more vessels within the vasculature. As shown in FIG. 9A, delivery device (900) is first introduced into the body (e.g., through the femoral or jugular arteries, or via any other suitable known access route), and then advanced through the vasculature to a target location. In the variation shown in FIG. 9A, the delivery device comprises an expandable balloon (902) having a device (904) disposed thereon. Of course, the delivery device need not be so configured, as any suitable delivery device may be used.

Once delivery device (900) has been advanced positioned at the desired location, the cannula may be withdrawn proximally or the balloon (902) advanced distally, to expose the device (904) to the target location, as shown in FIG. 9B. The balloon may then be expanded, and the device (904) deployed. Once fully expanded, as shown in FIG. 9C, the delivery device (900) may then be removed. The devices may be placed in veins or arteries, at locations of plaque formation (e.g., vulnerable plaque formation), or at locations of potential plaque formation. In addition, the devices may have a configuration that would be particularly desirable or suitable for use at a bifurcated vessel section.

With respect to use within the vasculature, the devices described here may have particular applicability in conjunction with treating thin-capped fibroatheromas (TCFAs), or other types of plaques. TCFAs are a class of plaques that, if ruptured, can cause rapid lumen occlusion and heart attack. The plaques have a number of structural features that make them more difficult to treat than stable lesions. By providing a device capable of releasing tissue-adhesion-promoting molecules to a TCFA, it may be possible to stabilize and strengthen the TFCA's cap, which in turn may allow the TCFA to receive treatment as if it were a stable lesion. Since TFCA's are susceptible to cap rupture, the devices may be made from a material that opens or may be opened in a slow, controlled manner. Additionally, in some variations, it may be desirable to release one or more pro-healing drugs to the TCFA.

Figure 10C:
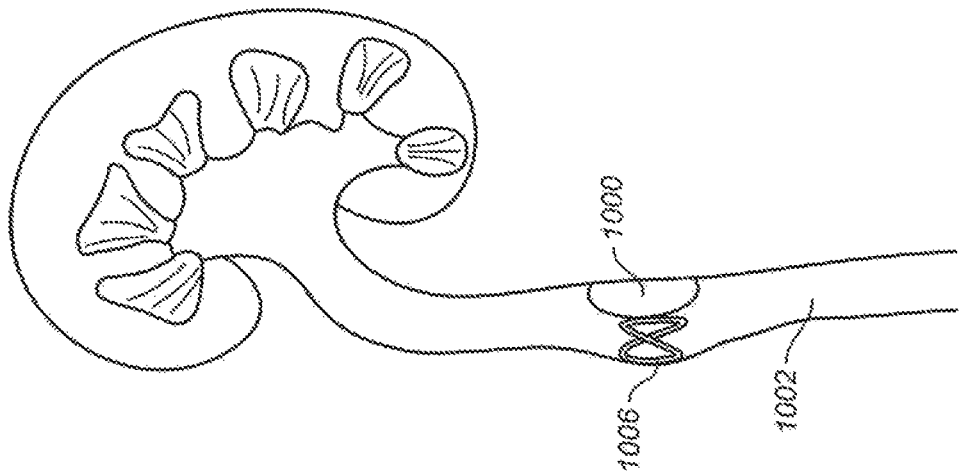
FIGS. 10A-10C depict an illustrative method of delivering a device to shunt urine around a blockage.
Figure 10B:
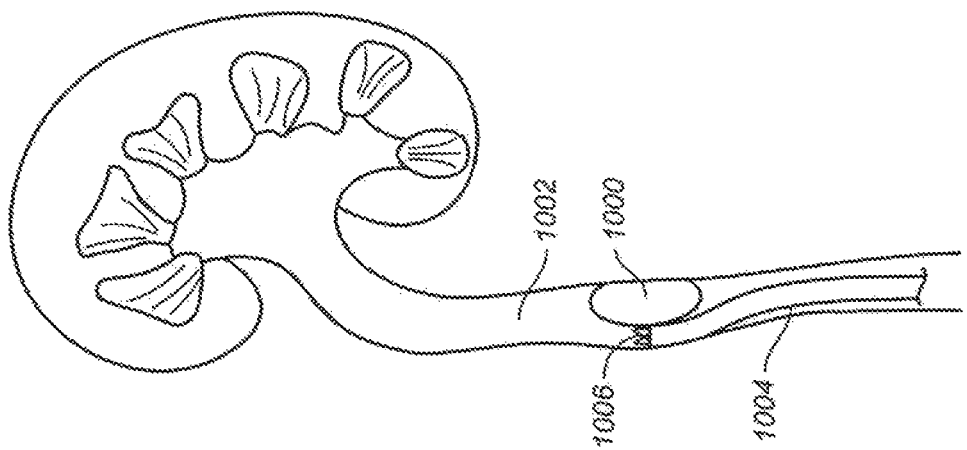
Figure 10A:
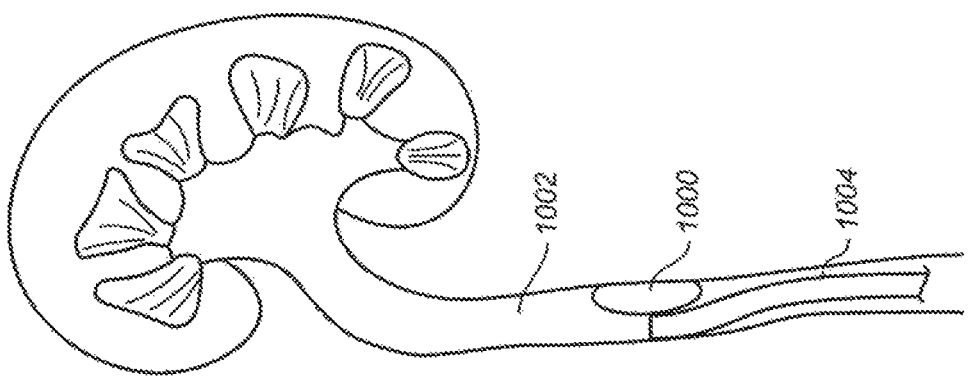

FIGS. 10A-10C illustrate one method of using the devices described here to shunt urine around a blockage (1000) of a ureter (1002). As shown in FIG. 10A, delivery device (1004) is advanced to a location between the wall of ureter (1002) and obstruction (1000). Once delivery device (1004) is positioned at a desirable location, as illustrated in FIG. 10B, device (1006) may then be deployed. When deployed, device (1006) creates a channel in ureter (1002) through which urine can pass, thereby bypassing the blockage (1000) as depicted in FIG. 10C. The delivery device (1004) may then be withdrawn.

The devices described here may also be used to treat urinary incontinence. For example, the devices may be placed in the bladder and/or the urethra to prevent obstruction of the urinary passageway by a growing prostrate or other circumstance. Drugs that may be useful in the treatment of urinary incontinence include, but are not limited to, alpha-blockers, imiprapine, antispasmodics, and 5-alpha reductase inhibitors.

III. Methods of Manufacture

The devices described herein may be made in any suitable manner. In general, the method comprises producing a polymer filament and forming the filament into the device. The method may optionally comprise coating the polymer filament with a drug eluting layer, doping the filament with drug depots, or the like. Additional steps may include heat setting and quenching the device, packaging the device, and sterilizing the device. These steps may be implemented in any appropriate order, and each step or combination of steps may be removed or replaced with other steps as necessary or appropriate.

The polymer filament may be produced by any suitable method. Methods of producing a polymer filament include, but are not limited to, extrusion molding, wet spinning, dry spinning, gel spinning, laser cutting and injection molding. In methods that use injection molding, the fully-formed device may be produced using injection molding. In methods that use extrusion molding, suitable polymers may be extruded using a melt phase process to form a polymer of a certain diameter. In these methods, the polymer will be brought to a temperature above the polymer melting temperature. At this point, the melted polymer or polymers are then pushed or drawn through a die to form the filament. This filament may be further drawn down to a smaller diameter in order to orient the polymer molecules. The drawing ratio may be any suitable ratio, for example 6.

When a drug eluting layer or drug depot is desired, a coating formulation (which may form the layer or depot) may be prepared. This coating formulation may be created by mixing a combination of degradable polymers, release-rate modifiers and drug components. The coating formulation may be configured to have a specific viscosity, depending on what process will be used to coat the filament. Since the drug delivery profile may partly depend on the viscosity, the coating formulation may have a viscosity that is suitable both for coating and for drug delivery.

Once the filament has been created and the coating formulation has been prepared, the filament may then be coated with the coating formulation to create a drug-eluting layer. In some variations, the filament is first plasma cleaned in order to improve adhesion of the coating formulation to the filament. The coating process may be any suitable process, including, but not limited to, spraying, misting, atomizing, dipping, brushing, pouring, dripping, spinning, roller coating, meniscus coating, powder coating and inking procedures. In some variations, the filament is formed into its final configuration prior to coating. In these variations, a coating fixture may be used to hold the device during the coating process. In some of these variations, the coating fixture may hold the formed filament by its apex, to allow for spraying or dipping without depositing the coating formulation on the coating fixture. In device variations that include loops, the loops may be used to secure the device to the coating fixture.

In some variations, a spray coating process is used where the spray coating follows or traces the device pattern. In these variations, the device is rotated and moved backwards and forwards under the spray head to trace the device pattern. Tracing the device patterns in such a manner may result in a transfer efficiency of as much as 20%, where the typical efficiency for device spray coaters is about 5%. In these variations, device loops may be used to provide the proper orientation for the device when placed on the coating fixture. Furthermore, in these variations, the coating fixture may include a spring that provides axial stress, thereby allowing the device to maintain its shape.

For devices that contain multiple drug eluting layers, a multi-coating process may be used to form the different layers. In one variation of a multi-coating process, the device filament may be run through a coating bath or a micro-pump that deposits a first coating on the device filament, which then passes through a heating or ultraviolet element in order to cure the layer. The device filament may then be run through additional depositing and curing elements in order to form additional layers.

The device filament may then be manipulated into a device configuration by any suitable method. In some variations, a formation fixture is used to determine the final shape of the device. In these variations, constant tension may be applied to the device filament as it is wound around the formation fixture into its final configuration. In doing so, the percent strain of the device filament may be controlled. Additionally, by winding the device filament around struts strategically located on the formation fixture, loops may be formed on the device. In other variations, the formation fixture is flat, and the device must eventually be manipulated into its final configuration.

Once the device filament is placed in its final configuration on the formation fixture or otherwise, the ends of the filament may be bonded to create a continuous filament loop. In some variations, this bonding is achieved by a biodegradable polymer glue in an appropriate solvent, and this polymer glue may be the same polymer as the coating polymer. In variations including polymer filaments, the solvent for the polymer glue is generally a non-solvent for the polymer filament. In other variations, the bonding may be achieved by heat welding, laser welding, ultrasonic welding, or RF welding of the device filament ends.

Once the device has been formed, it may be heat set. The device is generally heat set under tension, and any suitable heating parameters may be utilized, for example, heating at 120° C. for 10 minutes. In variations utilizing a polymer filament, the device may be heated at a temperature between the polymer filament glass temperature and its melting temperature. Once the device has been heated, it may then be quenched. Any suitable quenching parameters may be used, for example, cooling at −20° C. for 10 minutes. In variations utilizing a polymer filament, the device may be quenched at a temperature below the glass temperature of the polymer filament.

Once the device has been formed, heated, and quenched, drug depots may be added or filled with a drug. The device may be weighed at multiple times during this process, in order to determine the amount of drug added. Once the device has been completed, it may then be inspected, packaged and sterilized by any suitable processes. In some methods, the device may be packaged with a support to support and maintain the device form during sterilization and/or shipping. Similarly, a suture or filamentous material may be used to prevent the device from changing shape during these steps. Sterilization may utilize any suitable process, including, but not limited to, gamma sterilization and E-beam sterilization.

Figure 11:
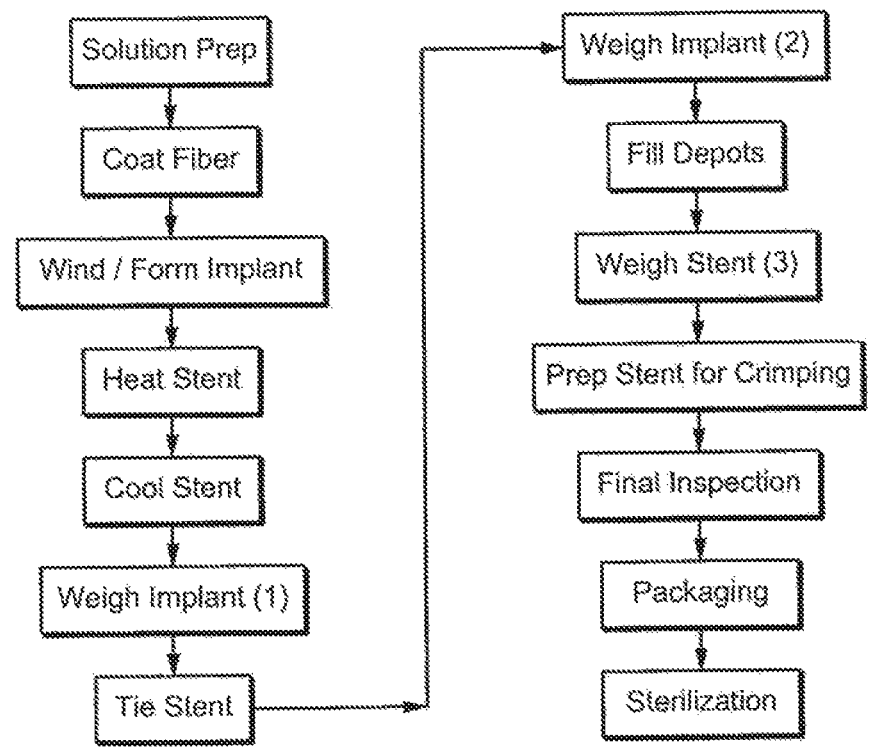
FIG. 11 is a flow chart outlining one variation of manufacturing the devices described herein.

FIG. 11 provides a flow chart illustrating one method of manufacturing the devices described herein in accordance with the techniques described just above. However, the devices may be formed from a number of alternate methods. In some variations, the device is cut from a film, e.g., a rolled cylinder. Alternatively, the device pattern may be cut from the film, and then rolled into a cylinder. In other processes, the device may be formed by bonding together smaller non-intersecting filament segments. In these variations any of the bonding methods mentioned above may be used to join the filament segments.

In still other variations, the device may be formed by compression, injection, or foam molding. In compression molding, solid polymeric materials are added to a mold, then pressure and heat are applied until the polymeric material conforms to the mold. The solid form may require additional processing to obtain the final product in a desired form. In injection molding, solid polymeric materials are added to a heated cylinder, softened and forced into a mold under pressure to create a solid form. The solid form may require additional processing to obtain the final product in a desired form. In foam molding, blowing agents are used to expand and mold solid polymeric materials into a desired form, and the solid polymeric materials can be expanded to a volume ranging from about two to about 50 times their original volume. The polymeric material can be pre-expanded using steam and air and then formed in a mold with additional steam; or mixed with a gas to form a polymer/gas mixture that is forced into a mold of lower pressure. The solid form may require additional processing to obtain the final product in a desired form.

IV. EXAMPLES

Device Preparation

A poly(L-lactide-co-glycolide) polymer filament with a lactide to glycolide ratio of about 10:90 was prepared by extruding the polymer using a melt phase process. The fiber was then drawn down with a drawing ratio of approximately 6, resulting in a diameter of about 0.36 mm. The resulting filament had a tensile strength of approximately 580 MPa, a Young's modulus of approximately 7400 MPa and a strain to failure between 50% and 60%. These values were determined using an Instron tensile test with a strain rate of 25 mm/min at room temperature.

A crown-shaped device, as described above and depicted in FIGS. 1A and B, was formed using the polymer filament, and was coated with a drug eluting layer. The device was further able to be reduced from an expanded configuration diameter of approximately 5 cm to a reduced profile diameter of about 4.5 mm. The expanded device was able to provide support to an area up to about 23.5 cm$^2$. The device was then sterilized using a 28±10% kGy e-beam sterilization dose. The sterilized device had an inherent viscosity of about 1.0 dL/g in HFIP at 25° C., as determined by a size 75 Cannon-Ubbelohde viscometer.

Mechanical Strength Testing

The mechanical strength of one variation of the devices described here as a function of time was tested. A number of crown-shaped devices, as described above, were made with a poly(L-lactide-co-glycolide) device filament with a lactide to glycolide ratio of about 10:90. A drug eluting coating was formed with approximately 6000 molecular weight polyethylene glycol, mometasone furoate, acetone and poly(DL-lactide-co-glycolide) with a lactide to glycolide ratio of about 70:30. The devices were packaged in pouches composed of a Foil/PE laminate, and were sterilized using E-beams with a total dose of 28 kGy±10%. The devices were removed from their packaging and stored with Sepragel (Genzyme Biosurgery, Cambridge, Mass.) and Meropack (MedtronicENT, Inc., Jacksonville, Fla.) in 50 mmol phosphate-buffered saline with a pH within the range of 7.4±0.2, at approximately 37° C. (to simulate body temperature).

Three crown devices underwent compressive strength testing, and all three devices were subjected to creep resistance testing. Testing occurred at an initial time point, at 3 days, 5 days, 7 days, 11 days and at 14 days. For compressive testing, five new device samples were used at each time point, totaling to 30 devices sampled. For creep resistance testing, each sample for each device was tested at every time point, and multiple samples of each device were tested (5 samples each for the crown shaped device and the Meropack device and 4 samples for the Sepragel device).

In compressive strength testing, the force required to compress each sample by 25% of the original nominal diameter of about 50 mm was measured. To collect these measurements, each sample was held between two plates with an initial separation of about 50 mm. The plates were then moved together at a rate of 5 mm/min, and the force required for the plates to reach a final separation of about 37.5 mm was recorded. A device was deemed to have passed the compressive strength test if its strength at 7 days was at least 25% of its initial value.

In the creep resistance testing, the samples of each device were placed into models of ethmoid sinuses following functional endoscopic sinus surgery (FESS), each having a free floating middle turbinate represented by a free-floating, clear acrylic plate. The model dimensions (about 30 mm in length, about 14 mm in height, and about 15 mm in depth) were based on the average dimensions of a post-FESS surgery ethmoid sinus, as provided in Lang J.—Clinical Anatomy of the Head: Neurocranium, orbit, craniocervical regions (Springer, New York 1981). The samples were placed such that they prevented the acrylic plates from contacting the bases of the models. At each time period, the distance between the bottom of the model and acrylic plate for each sample was measured in order to evaluate the ability of the implant to support the free floating middle turbinate. A device was considered to pass the creep resistance test if, at 7 days, the plate height was at least 50% of the initial height (i.e., about 7 mm).

Table 1 shows the compressive strength of the device samples at the various testing points. Specifically, Table 1 shows the mean radial strength for the sample test group at each time period, the standard deviations of those strengths, and the number of fractures that occurred on that day. At 7 days, the devices retained 47.7% of their original strength, and thus all of the devices passed the test. At 14 days, four of the five device samples had fractured, and thus no standard deviation could be calculated for that test group.

TABLE 1

| | Compressive Strength (n = 5) | | |
| --- | --- | --- | --- |
| Time Points | Mean (N) | Standard Deviation | Number of Fractures |
| Initial | 0.01592 | 0.00164 | 0 |
| Day 3 | 0.00812 | 0.00123 | 0 |
| Day 5 | 0.00824 | 0.00089 | 0 |
| Day 7 | 0.00759 | 0.00130 | 0 |
| Day 11 | 0.00511 | 0.00105 | 1 |
| Day 14 | 0.00438 | N/A | 4 |

Table 2 shows the creep resistance values for the various samples. More specifically, Table 2 shows the average plate height and the corresponding standard deviation for each set of devices at each time period. At 14 days, the devices still provided about 14 mm of separation between the free floating plates and the model bases, and thus all of the devices passed the creep resistance test. The Sepragel devices yielded no separation at 3 days. The Meropack devices provided their greatest separations at 3 days, averaging 8.58 mm, but these separations diminished to an average of 1.28 mm at 14 days.

TABLE 2

| | Average Plate Height (mm) | | |
| --- | --- | --- | --- |
| Time Points | Sample Device | Sepragel | Meropack |
| Initial | 14.13 ± 0.08 | 2.08 ± 0.32 | 3.14 ± 0.04 |
| Day 3 | 14.11 ± 0.09 | 0 | 8.58 ± 1.21 |
| Day 5 | 14.10 ± 0.15 | 0 | 8.15 ± 1.10 |
| Day 7 | 14.12 ± 0.10 | 0 | 4.81 ± 2.08 |
| Day 11 | 14.08 ± 0.06 | 0 | 2.29 ± 1.79 |
| Day 14 | 14.05 ± 0.09 | 0 | 1.28 ± 1.71 |

Drug Delivery

Figure 12:
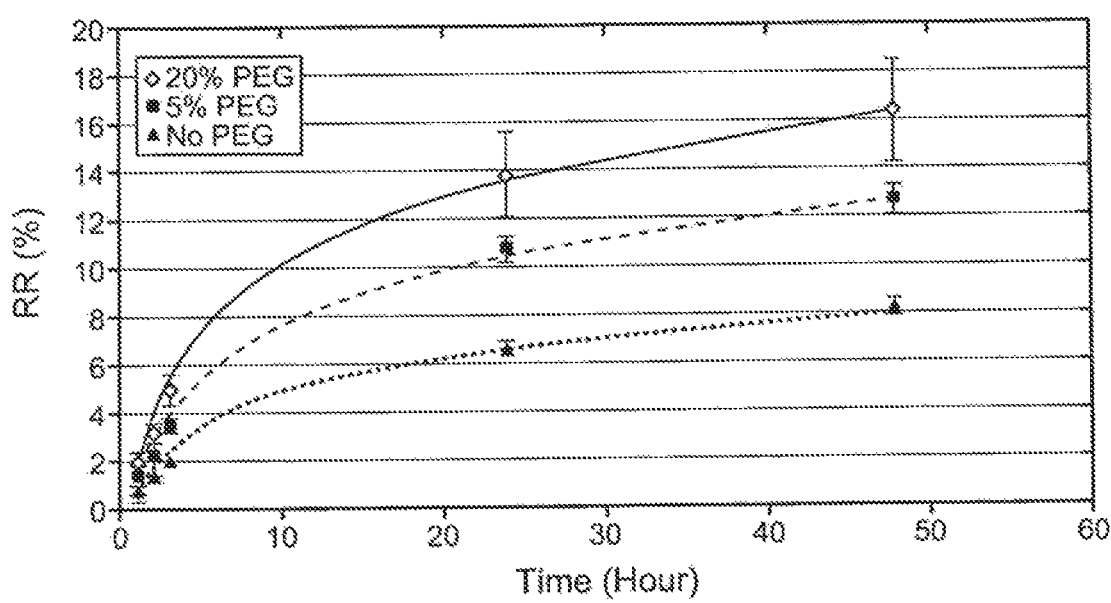
FIG. 12 provides the drug release profiles for three different devices.

Crown shaped devices, as described above, were made having a poly(L-lactide-co-glycolide) filament with a lactide to glycolide ratio of about 10:90. Drug eluting coatings were formed containing mometasone fuorate, acetone, and poly (DL-lactide-co-glycolide) with a lactide to glycolide ratio of 70:30. One coating had no PEG, one coating had 5 weight % PEG 6000, and another coating had 20 weight % PEG 6000. FIG. 12 illustrates how the release of an agent can change with the addition of a release rate modifier, in this case, polyethylene glycol.

Figure 13:
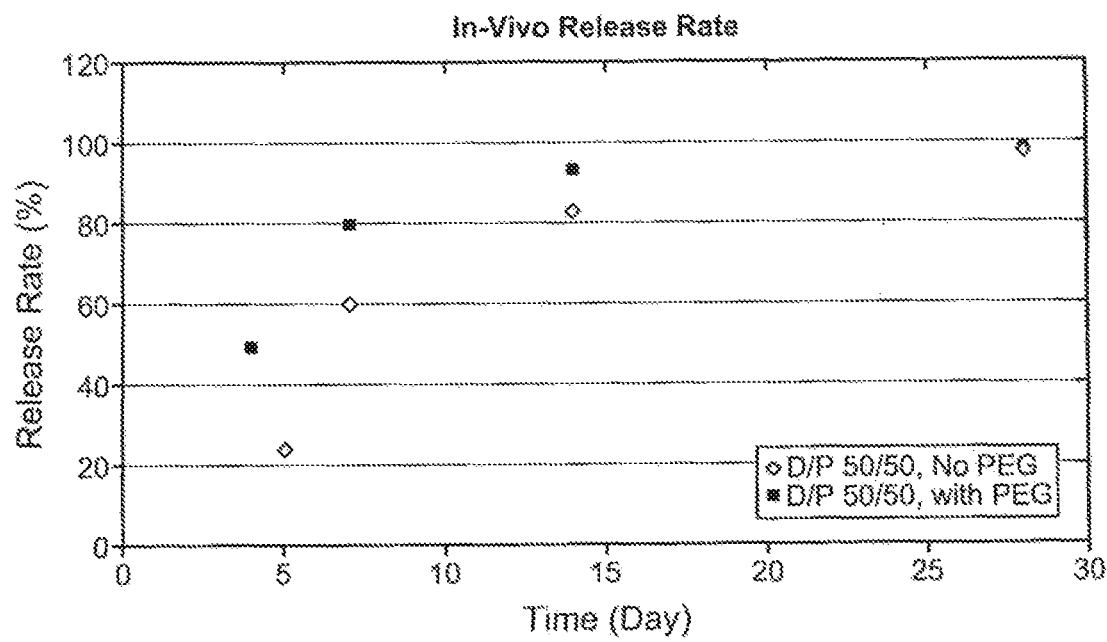
FIG. 13 depicts in vivo release rate data for three exemplary devices described here.

The in vivo release of mometasone furoate was studied using a rabbit model. Crown shaped devices, as described above, were made having a poly(L-lactide-co-glycolide) filament with a lactide to glycolide ratio of about 10:90. Drug eluting coatings were formed containing mometasone fuorate, acetone, and poly(DL-lactide-co-glycolide) with a lactide to glycolide ratio of 50:50. One coating had no PEG, and the second coating contained 20 weight % PEG 6000. The crown shaped devices were implanted into the maxillary sinus of the rabbits. The devices were then explanted at different time points. For each time point, the amount of mometasone furoate remaining on the device was measured using a High Performance Liquid Chromatographic (HPLC) based assay. The release rate of mometasone furoate was then calculated based on the amount remaining on the device. FIG. 13 shows the in vivo release data, and demonstrates how the release rate profile can be adjusted by changing the coating formulation.

Figure 14:
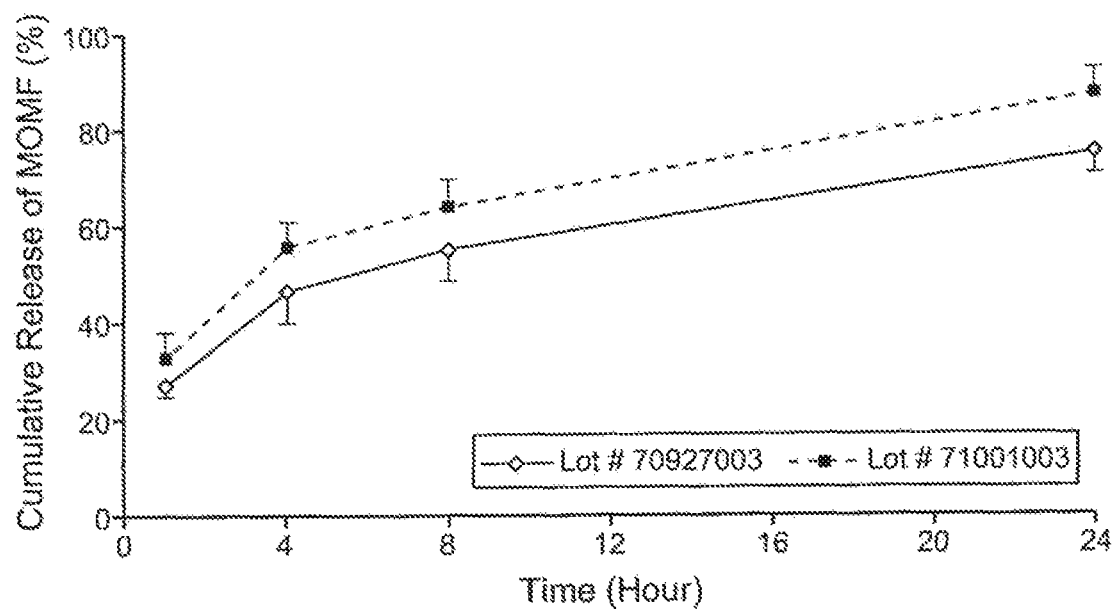
FIG. 14 illustrates the cumulative release of mometasone furoate from two different illustrative devices as described here.

The in vitro release of mometasone furoate was studied using an accelerated HPLC release rate assay. Crown shaped devices, as described above, were made having a poly(L-lactide-co-glycolide) filament with a lactide to glycolide ratio of about 10:90. Drug eluting coatings were formed containing mometasone fuorate, acetone, and poly(DL-lac-tide-co-glycolide) with a lactide to glycolide ratio of 50:50. One coating had no PEG, and the second coating had 20 weight % PEG 6000. FIG. 14 illustrates the cumulative release of mometasone furoate from the two formulations.

We claim:

1. A method of treating one or more sinus conditions in a patient, the method comprising:
dilating a paranasal sinus region with an expandable balloon, wherein an expandable device is detachably coupled around the expandable balloon;
delivering the expandable device to the dilated paranasal sinus region, wherein the expandable device disengages from the expandable balloon, wherein the expandable device is configured to expand from a first compressed configuration to a second expanded configuration for conformation against sinus tissue, and wherein the expandable device is at least partially coated with a drug eluting layer comprising a drug, the drug eluting layer configured to release the drug at a daily dosage of about 500 μg or less per day; and
withdrawing the expandable balloon from the paranasal sinus region after dilation.

2. The method of claim 1, wherein the expandable device comprises one or more biodegradable polymer filaments arranged to form repeating diamond-shaped pattern and wherein a distal end of the expandable device and a proximal end of the expandable device are defined by each of the diamond shapes.

3. The method of claim 1, wherein the expandable device is self-expanding.

4. The method of claim 1, wherein the expandable device has a compressed diameter in the first compressed configuration and an expanded diameter in the second expanded configuration, and wherein the ratio of the expanded diameter to the compressed diameter is from about 2:1 to about 20:1.

5. The method of claim 1, wherein the drug comprises a therapeutic agent comprising one or more selected from the group consisting of: anti-inflammatory agents, anti-allergens, antibiotics, anti-cholinergic agents, antihistamines, anti-infectives, anti-platelet agents, anti-coagulants, anti-thrombic agents, anti-scarring agents, anti-proliferative agents, chemotherapeutic agents, anti-neoplastic agents, decongestants, healing promoting agents, vitamins, hyperosmolar agents, immunomodulators, and immunosuppressive agents.

6. The method of claim 5, wherein the drug is an anti-inflammatory agent that comprises mometasone furoate, fluticasone propionate, or both.

7. The method of claim 1, wherein the drug eluting layer is configured to release the drug over a period of time between about 5 days to about 120 days.

8. The method of claim 1, wherein the drug eluting layer comprises a release rate modifier.

9. The method of claim 1, wherein delivering the expandable device comprises delivering the expandable device to an ethmoid sinus cavity or ostium, a maxillary sinus cavity or ostium, a frontal sinus cavity or ostium, a sphenoid sinus cavity or ostium, or an osteomeatal complex.

10. The method of claim 1, wherein the one or more biodegradable polymer filaments comprise poly-(lactide-co-glycolide).

11. The method of claim 1, wherein the one or more biodegradable polymer filaments comprise paclitaxel.

* * * * *